United States Patent
Forsell

(10) Patent No.: US 10,993,801 B2
(45) Date of Patent: May 4, 2021

(54) ARTIFICIAL VALVE

(71) Applicant: Peter Forsell, Bouveret (CH)

(72) Inventor: Peter Forsell, Bouveret (CH)

( * ) Notice: Subject to any disclaimer, the term of this patent is extended or adjusted under 35 U.S.C. 154(b) by 0 days.

(21) Appl. No.: 15/276,820

(22) Filed: Sep. 27, 2016

(65) Prior Publication Data

US 2017/0112617 A1      Apr. 27, 2017

Related U.S. Application Data

(63) Continuation of application No. 13/123,667, filed as application No. PCT/SE2009/051150 on Oct. 12, 2009, now Pat. No. 9,452,045.

(60) Provisional application No. 61/213,158, filed on May 12, 2009.

(30) Foreign Application Priority Data

Oct. 10, 2008 (SE) .................... 0802146-1

(51) Int. Cl.
*A61F 2/24* (2006.01)
*A61M 1/12* (2006.01)
*A61B 5/00* (2006.01)
*A61B 5/07* (2006.01)

(52) U.S. Cl.
CPC .......... *A61F 2/2403* (2013.01); *A61B 5/6846* (2013.01); *A61F 2/2409* (2013.01); *A61B 5/076* (2013.01); *A61F 2210/009* (2013.01); *A61F 2250/0001* (2013.01)

(58) Field of Classification Search
CPC ........ A61F 2/24; A61F 2/2403; A61F 2/2409; A61F 2002/068; A61F 2/06; A61F 2/07; A61F 2/2418; A61F 2/2421; A61F 2/2469; A61F 2/2442; A61M 1/12; A61M 1/125; A61M 1/122; A61B 17/0057
See application file for complete search history.

(56) References Cited

U.S. PATENT DOCUMENTS

| | | | | |
|---|---|---|---|---|
| 4,527,549 A | * | 7/1985 | Gabbay | A61M 1/1072 600/18 |
| 4,979,955 A | * | 12/1990 | Smith | A61F 2/2406 137/514 |
| 5,951,600 A | * | 9/1999 | Lemelson | A61K 9/0009 623/2.11 |
| 6,730,118 B2 | * | 5/2004 | Spenser | A61F 2/2412 623/1.24 |
| 7,291,168 B2 | * | 11/2007 | Macoviak | A61F 2/2412 623/2.36 |

(Continued)

*Primary Examiner* — Alvin J Stewart

(57) ABSTRACT

The invention discloses an artificial valve (10, 20) for implantation in a mammal aorta or heart as an auxiliary aortic valve in addition to an aortic valve. The artificial valve (10, 20) comprises at least a first (12,17) moving part adapted to be able to move to assume an open and a closed position for opening and closing, respectively, of the blood flow through a blood vessel. The artificial valve (10, 20) also comprises a casing (14, 24), and said at least one first (12, 17) moving part is movably attached to said casing (14, 24). The artificial valve (10, 20) is adapted to let the at least one moving part initiate its movement to the open position at a level of blood pressure on a blood supplying side of the valve which is at least 5 mm Hg higher than the mammal's diastolic aortic blood pressure on the other side of the valve.

21 Claims, 32 Drawing Sheets

(56) References Cited

U.S. PATENT DOCUMENTS

| | | | | |
|---|---|---|---|---|
| 7,527,646 B2* | 5/2009 | Rahdert | A61F 2/2454 | 623/2.36 |
| 7,572,217 B1* | 8/2009 | Koenig | A61M 1/1081 | 600/16 |
| 7,766,814 B2* | 8/2010 | Walsh | A61F 2/06 | 600/16 |
| 8,142,494 B2* | 3/2012 | Rahdert | A61F 2/2454 | 623/2.36 |
| 8,784,483 B2* | 7/2014 | Navia | A61F 2/2445 | 623/2.36 |
| 9,107,992 B2* | 8/2015 | Kushwaha | A61M 1/1036 | |
| 9,402,718 B2* | 8/2016 | Forsell | A61F 2/2403 | |
| 9,452,045 B2* | 9/2016 | Forsell | A61B 5/6846 | |
| 9,474,839 B2* | 10/2016 | Oran | A61M 1/122 | |
| 10,226,329 B2* | 3/2019 | Forsell | A61F 2/2403 | |
| 2002/0103413 A1* | 8/2002 | Bugge | A61M 1/127 | 600/16 |
| 2005/0004668 A1* | 1/2005 | Aklog | A61F 2/2448 | 623/2.36 |
| 2005/0010287 A1* | 1/2005 | Macoviak | A61F 2/2445 | 623/2.36 |
| 2005/0021134 A1* | 1/2005 | Opie | A61F 2/02 | 623/2.2 |
| 2005/0038508 A1* | 2/2005 | Gabbay | A61F 2/2445 | 623/2.36 |
| 2006/0069430 A9* | 3/2006 | Rahdert | A61F 2/2454 | 623/2.36 |
| 2006/0178552 A1* | 8/2006 | Gross | A61F 2/24 | 600/16 |
| 2007/0225802 A1* | 9/2007 | Forsell | A61F 2/2421 | 623/2.34 |
| 2008/0147181 A1* | 6/2008 | Ghione | A61F 2/2436 | 623/2.11 |
| 2008/0243064 A1* | 10/2008 | Stahler | A61B 34/71 | 604/95.01 |
| 2011/0196476 A1* | 8/2011 | Forsell | A61F 2/2421 | 623/1.24 |
| 2011/0196481 A1* | 8/2011 | Forsell | A61F 2/2403 | 623/2.17 |
| 2011/0196482 A1* | 8/2011 | Forsell | A61F 2/2427 | 623/2.17 |
| 2011/0201870 A1* | 8/2011 | Forsell | A61F 2/01 | 600/16 |
| 2011/0202129 A1* | 8/2011 | Fofsell | A61B 5/6846 | 623/2.17 |
| 2012/0245678 A1* | 9/2012 | Solem | A61M 1/127 | 623/2.36 |
| 2013/0138205 A1* | 5/2013 | Kushwaha | A61M 1/1087 | 623/1.26 |
| 2013/0281762 A1* | 10/2013 | Kushwaha | A61M 1/125 | 600/17 |
| 2015/0174308 A1* | 6/2015 | Oran | A61M 1/122 | 623/3.13 |
| 2016/0089482 A1* | 3/2016 | Siegenthaler | A61F 2/24 | 600/16 |
| 2016/0101230 A1* | 4/2016 | Ochsner | A61M 1/3666 | 600/17 |
| 2016/0121034 A1* | 5/2016 | Foster | A61M 1/1013 | 600/16 |
| 2017/0112617 A1* | 4/2017 | Forsell | A61B 5/6846 | |
| 2017/0216507 A1* | 8/2017 | Kushwaha | A61M 1/127 | |
| 2018/0193543 A1* | 7/2018 | Sun | A61M 1/122 | |
| 2019/0351120 A1* | 11/2019 | Kushwaha | A61M 1/1017 | |

* cited by examiner

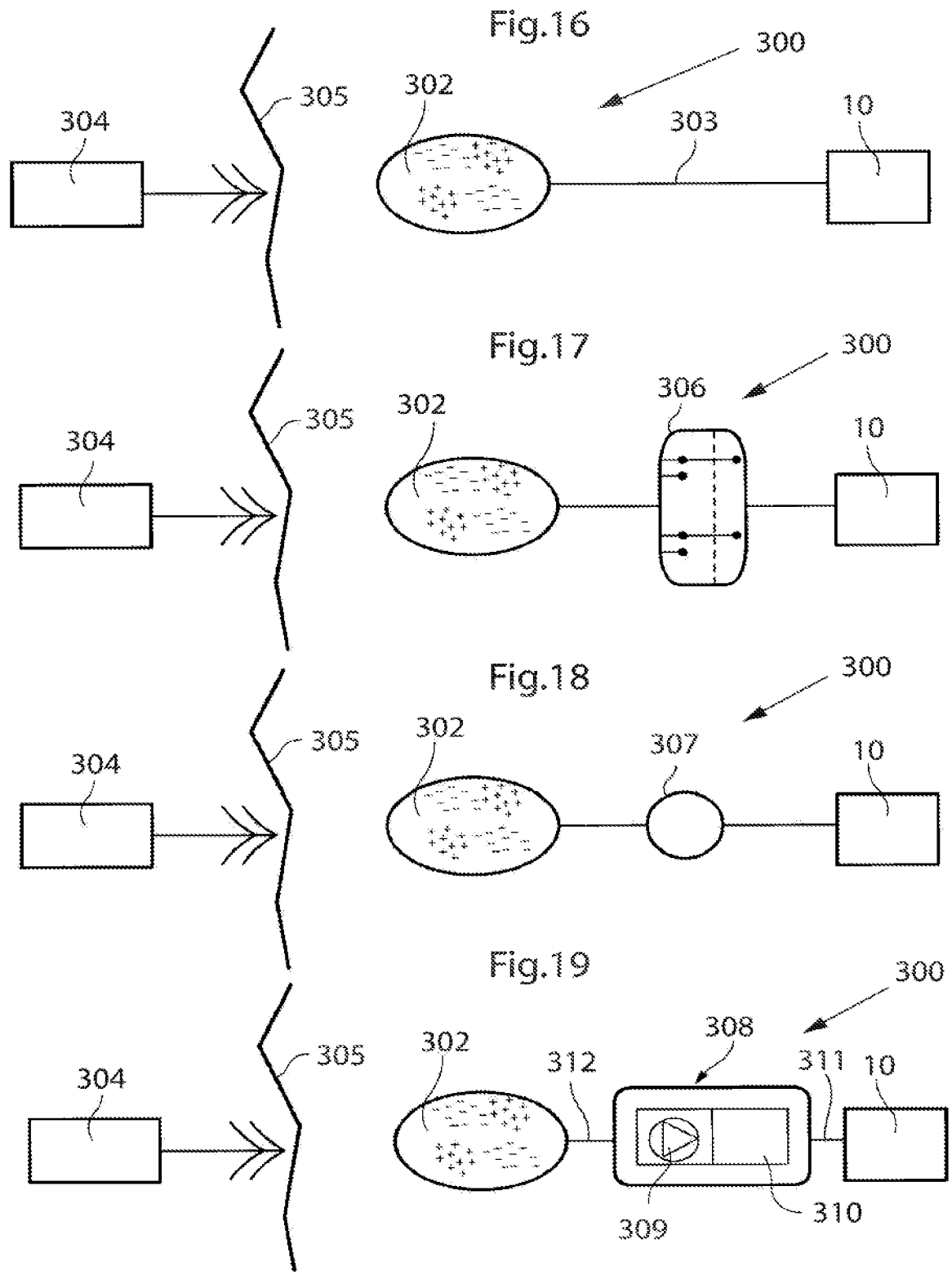

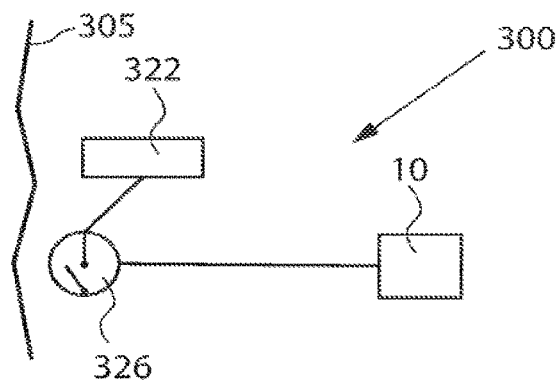
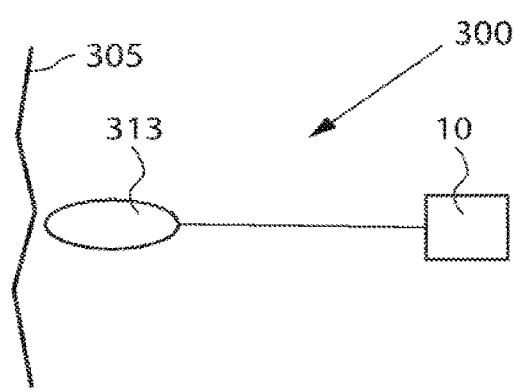
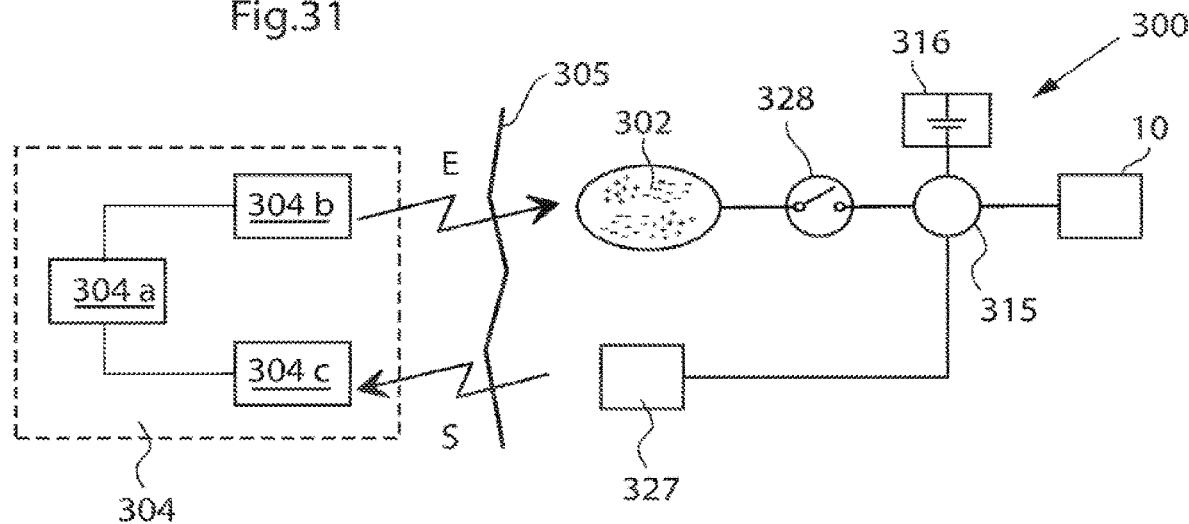

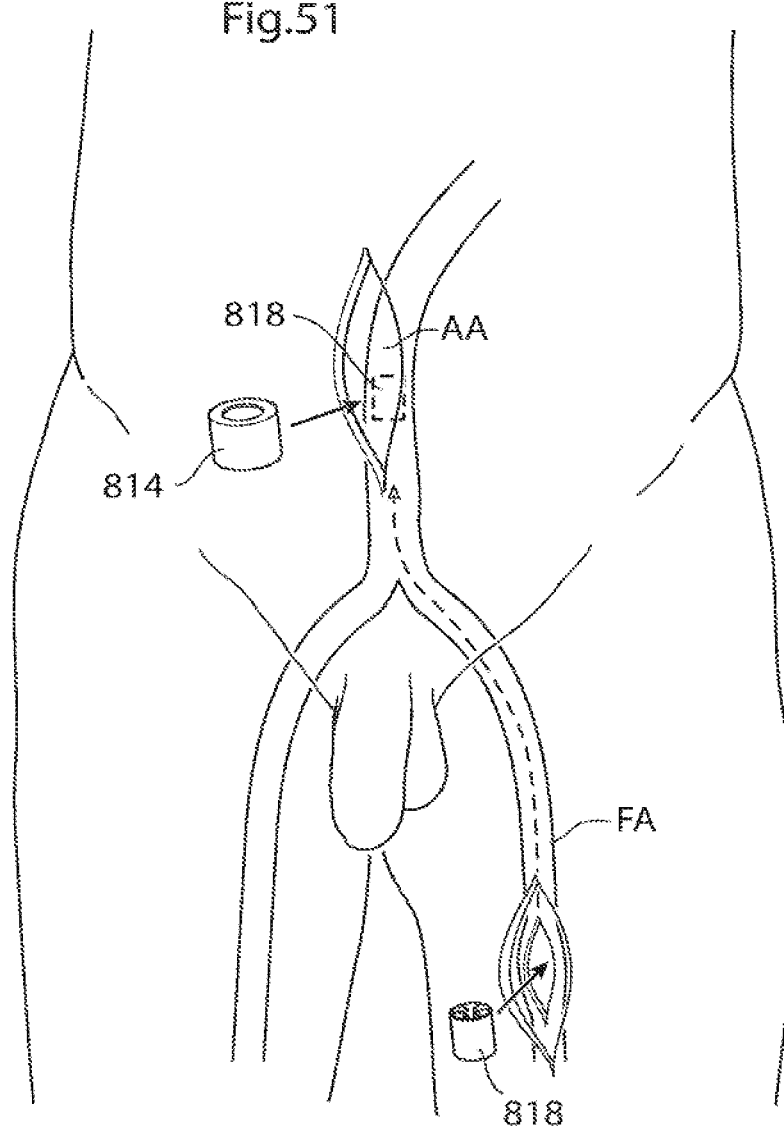

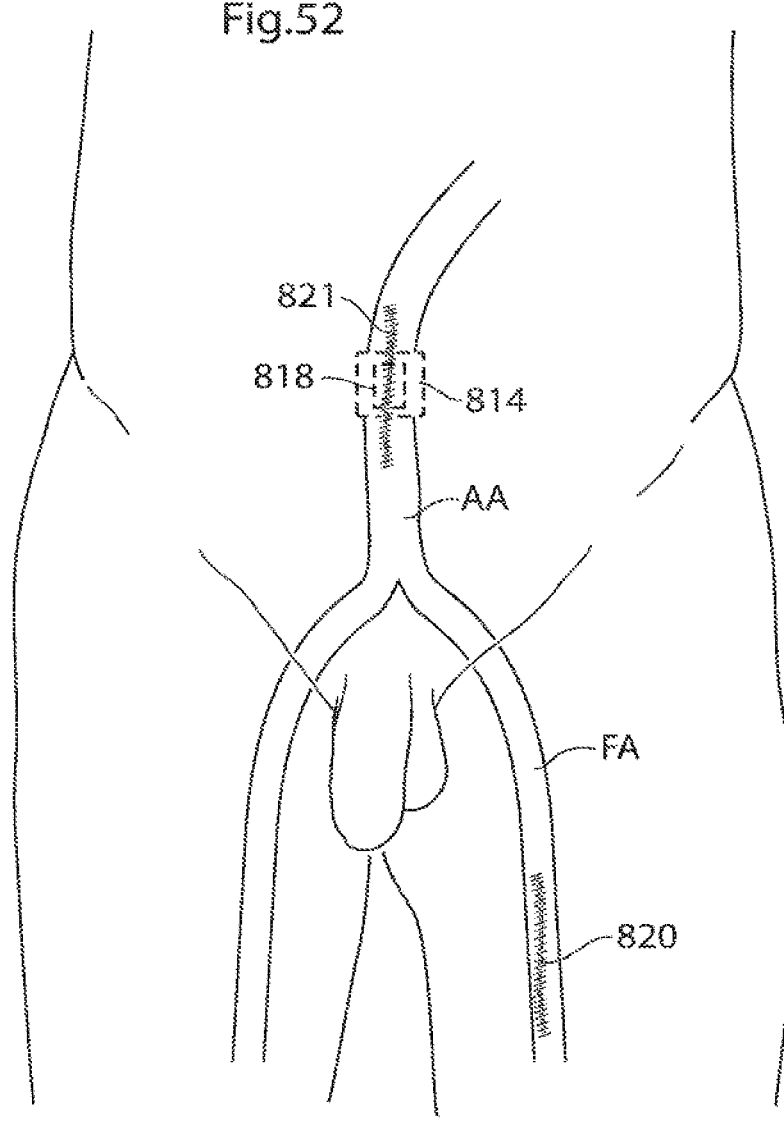

ARTIFICIAL VALVE

This application is a continuation of U.S. application Ser. No. 13/123,667, filed 11 Apr. 2011, which is the U.S. national phase of International Application No. PCT/SE20091051150, filed 12 Oct. 2009, which designated the U.S. and claims priority to SE 0802146-1 filed 10 Oct. 2008, and which claims the benefit of Ser. No. 61/213,158 filed 12 May 2009, the entire contents of each of which are hereby incorporated by reference.

TECHNICAL FIELD

The present invention discloses an artificial valve for implantation in a mammal blood vessel and a method for implanting such a valve into a mammal blood vessel.

BACKGROUND

Artificial valves for implantation into mammal blood vessels are used in order to replace existing valves in the circulatory system of a mammal. When inserted in the circulatory system of a mammal, such valves are used to regulate the flow of blood in the mammal by means of closing or opening the blood flow in the vessel, which is accomplished by means of letting moving parts in the valve come together to assume a closed position or to move apart to assume an open position.

SUMMARY

It is an object of the present invention to provide an artificial valve for implantation into a mammal blood vessel which overcomes drawbacks of known such artificial valves.

This object is obtained by means of an artificial valve for implantation in a mammal aorta or heart as an auxiliary aortic valve in addition to an aortic valve. The artificial valve of the invention comprises at least a first moving part which is adapted to be able to move to assume an open and a closed position for opening and closing, respectively, of the blood flow through a blood vessel, and the artificial valve also comprises a casing. In the artificial valve, the at least one first moving part is movably attached to said casing, and the artificial valve is adapted to let the at least one moving part initiate its movement to the open position at a level of blood pressure on a blood supplying side of the valve which is at least 5 mm Hg higher than the mammal's diastolic aortic blood pressure on the other side of the valve.

In one embodiment, the artificial valve is adapted to let the at least one moving part initiate its movement to said open position at a level of blood pressure on a blood supplying side of the valve which is at least 10 mm Hg higher than the mammal's diastolic aortic blood pressure on the other side of the valve.

In one embodiment, the artificial valve is adapted to let the at least one moving part initiate the movement to the closed position at a point in the mammal's heart cycle which is delayed compared to a normal aortic valve by at least ⅓ of the mammal's heart's diastolic phase.

In one embodiment, the artificial valve comprises a passive resistance mechanism by means of which a barrier force is created which corresponds to said level of blood pressure, with the at least one moving part being adapted to be opened by the blood flow at said level of blood pressure, the artificial valve being adapted to let said at least one first moving part move freely after the barrier force has been reached.

In one embodiment, the passive resistance mechanism of the artificial valve is arranged to offer resistance until said predetermined level of the barrier force is reached.

In one embodiment, the passive resistance mechanism of the artificial valve is arranged to only offer resistance in the opening movement of said at least one first moving part.

In one embodiment, the comprises at least a first and a second moving part which are adapted to assume an open and a closed position for opening and closing, respectively, of the blood flow through the vessel. The valve of the invention also comprises a casing, and the moving parts of the inventive valve are movably attached to the casing.

In one embodiment of the valve of the invention, the moving parts come together to form a cupola in the closed position of the valve.

By means of this cupola shape, the valve will exhibit a higher degree of strength in the closed position than known valves.

Suitably, this embodiment of the inventive valve also comprises a third moving part, which is adapted to assume an open and a closed position for opening and closing, together with said first and second parts respectively, the blood flow through the blood vessel, and to come together with the first and second parts to form a cupola in the closed position of the valve.

In one embodiment, the valve of the invention comprises two or more additional moving parts, so that there are four or more moving parts altogether, which are adapted to together assume an open and a closed position for opening and closing the blood flow through the blood vessel, and to come together to form a cupola in the closed position of the valve.

In one embodiment of the inventive valve, each of the moving parts is movably hinged about respective first and second hinges in the casing, and each of said moving parts can move about these hinges to assume a closed and an open position as well as positions in between said open and closed positions, with the first and second hinges of at least one of the moving parts being positioned at or adjacent to a meeting point of two of said parts.

Also in one embodiment, the first and second hinges of at least one of said moving parts are placed at substantially opposite distal ends of said moving part along the casing.

In one embodiment, the moving parts of the valve are adapted to be opened by the blood flow, as an alternative or complement to which the moving parts can be adapted to be closed to the cupola position by the blood flow.

Also, in one embodiment, the moving parts of the valve are adapted to be closed to the cupola position by blood pressure of a certain level.

In one embodiment, the valve comprises a resistance mechanism by means of which a barrier force of a predetermined level is needed to initiate the opening movement of the moving parts, so that the moving parts are given an initial moving resistance before the valve opens to allow blood to flow through the valve. Suitably but not necessarily, the barrier force is equal to that caused by a blood pressure of 10 mm Hg or more.

In one embodiment, the valve additionally comprises an operating mechanism which is adapted to power the moving parts in their movements to the closed and/or open position, so that the closing of the valve is active, and the powering is done at least in part by means of a power source which is external to the blood vessel, In one embodiment, the valve also comprises a receiving device which will receive a closing and/or an opening signal and will supply this signal to the operating mechanism which in turn will cause the moving parts to close and/or open upon its reception of said signal from the receiving device.

These and other embodiments will be described in more detail below.

BRIEF DESCRIPTION OF THE DRAWINGS

The invention will be described in more detail in the following with reference to the appended drawings, in which

FIGS. 16-30 schematically show various embodiments of the system for wirelessly powering the apparatus shown in FIG. 15.

FIG. 31 is a schematic block diagram illustrating an arrangement for supplying an accurate amount of energy used for the operation of the apparatus shown in FIG. 15.

FIGS. 49-52 illustrate an operation method of the invention

DETAILED DESCRIPTION

The invention will be described in the following with reference to a human blood vessel, and may also be described below as being placed in a human heart. It should however be pointed out that these are merely examples given in order to facilitate the reader's understanding of the invention; the artificial valve of the invention can be used more or less in any point in the circulatory system of any mammal.

In addition, the artificial valve of the invention can be used in order to replace a biological valve, as an alternative to which it can be used in order to supplement a biological valve, or to create a "valve function" in a position where the body is normally not equipped with a valve function.

Figure 1A:
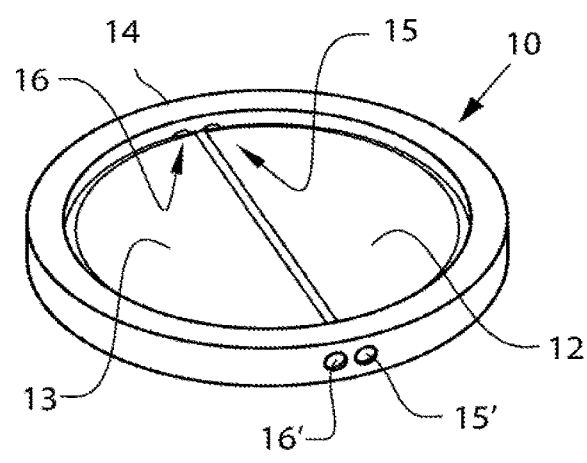
FIGS. 1a-1d show side views of two versions of a first embodiment of the invention.

FIG. 1a shows a side view of a first embodiment 10 of an artificial valve of the present invention.

As seen in FIG. 1a, the valve 10 of the first embodiment comprises a first 12 and a second 13 moving part, as well as a casing 14. In the embodiment shown in FIG. 1a, the casing has a circular or ring-formed shape, in order to enable it to be implanted against the inner wall of a blood vessel.

Figure 1B:
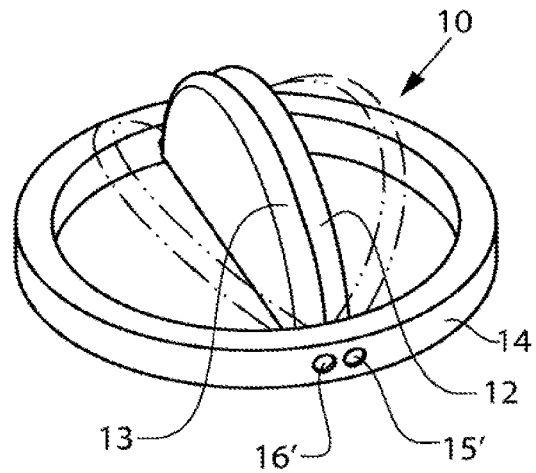

As is also shown in FIGS. 1a and 1b, the two moving parts 12 and 13 are movably attached to the casing 14 and are adapted to assume a closed (FIG. 1a) and an open (FIG. 1b) position, so that the blood flow through a blood vessel can be closed and opened, respectively.

As indicated in FIGS. 1a and 1b, both of the moving parts 12 and 13 are movably hinged about respective first 15, 15' and second 16, 16' hinges in the valve casing 14. The moving parts are adapted to move about these hinges to assume the closed and open positions mentioned above, as well as positions in between the open and closed positions. In one embodiment, as shown in FIGS. 1a and 1b, the first 15, 15' and second 16, 16' hinges of at least one of the moving parts are positioned at or adjacent to a meeting point of the two moving parts 12, 13.

As also shown in FIGS. 1a and 1 b, the positioning of the hinges 15, 15'; 16, 16' at meeting points of the parts 12 and 13 will cause the first and second hinges of at least one of said moving parts to be placed at substantially opposite distal ends of said moving part along the casing. This positioning of the hinges in the valve of the invention is advantageous as compared to known artificial valves in which the hinges are placed at a position essentially in the middle of the moving part, i.e. essentially at a centre position between the two distal edges of the moving part. One advantage of the positioning of the hinges of the present invention is that this positioning has been found to facilitate a smoother movement than conventionally placed hinges.

Figure 1C:
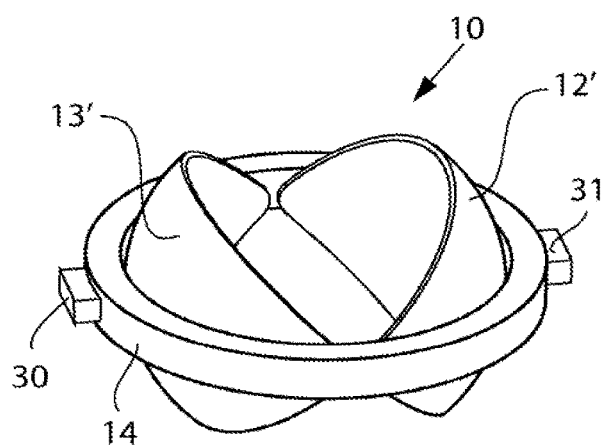
Figure 1D:
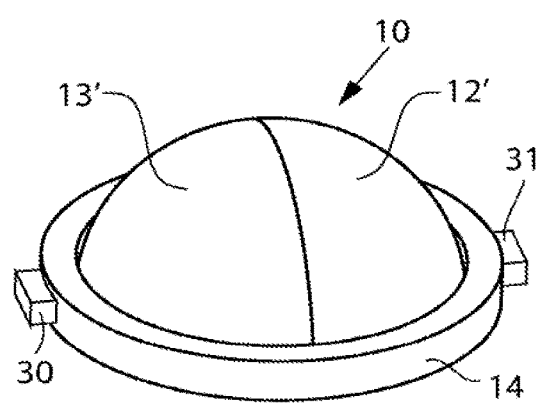

In the embodiments of FIGS. 1a and 1b, the moving parts 12 and 13 are shown as two essentially equal halves of a flat disc. In another embodiment, shown in FIGS. 1c and 1d, two moving parts 12' and 13' are instead shaped so that they come together in the closed position to form a cupola. In FIGS. 1c and 1d, each of the two parts 12', 13' of the valve 10 constitute half a cupola. The division between the two parts of the cupola is suitably such that each part 12', 13' comprises half a cupola, although other divisions of the cupola into the two parts 12' and 13' can also be envisioned within the scope of the present invention.

The cupola shape of the valve 10 in its closed position is advantageous as compared to conventional artificial valves which are flat, due to the fact that the cupola shape allows for a larger opening in the vessel, and will cause less turbulence of the blood flow in its open position.

As can be seen in FIGS. 1a-1d, at least the inside of the casing should be slanted, for example as a continuation of the cupola form of the moving parts in their closed position, in order to allow the moving parts to carry out their movements.

FIGS. 2a-2e show side views of another embodiment 20 of the valve of the invention: in the embodiment 20, the valve comprises a casing 24 which is similar to the casing 14 of FIGS. 1a-1d, and also comprises first and second moving parts 17 and 18, as well as a third moving part 19. The three moving parts are adapted to assume an open and a closed position for opening and closing, respectively, the blood flow through the blood vessel, and to come together with the first and second parts to form a cupola in the closed position of the valve.

The first, second and third moving parts 17, 18, 19 are hinged about respective hinges 21, 21'; 22, 22'; 23, 23', which in function and position are similar to the hinges of the first and second parts of the embodiment 10 of FIGS. 1a-1d.

Figure 2A:
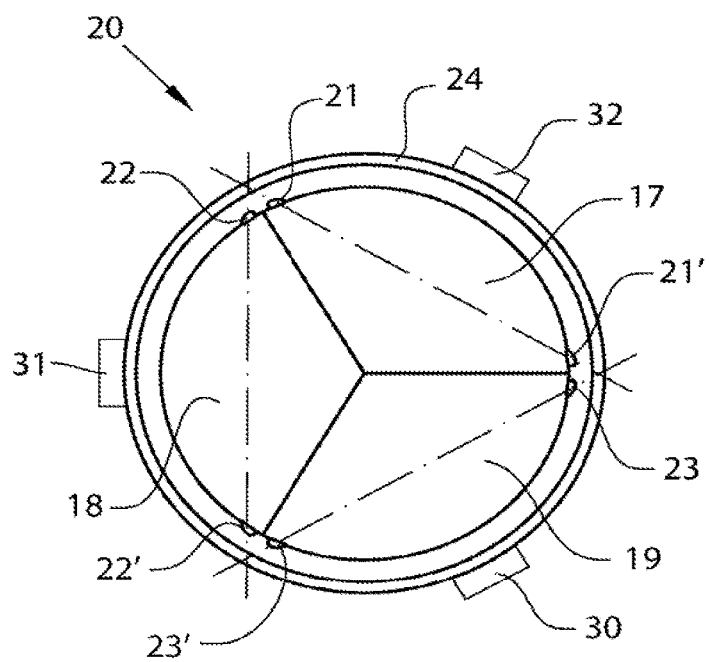
FIGS. 2a-2e show different views of a second embodiment of the invention.
Figure 2B:
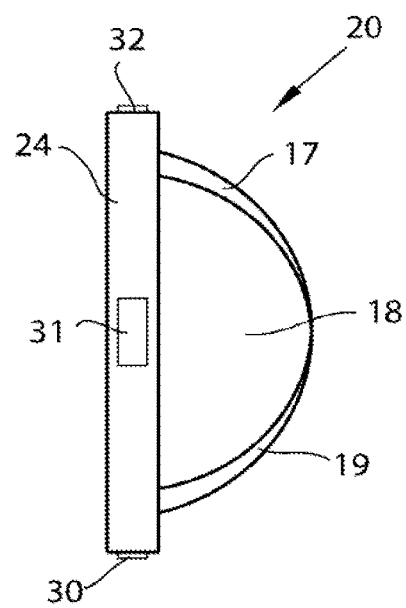
Figure 2C:
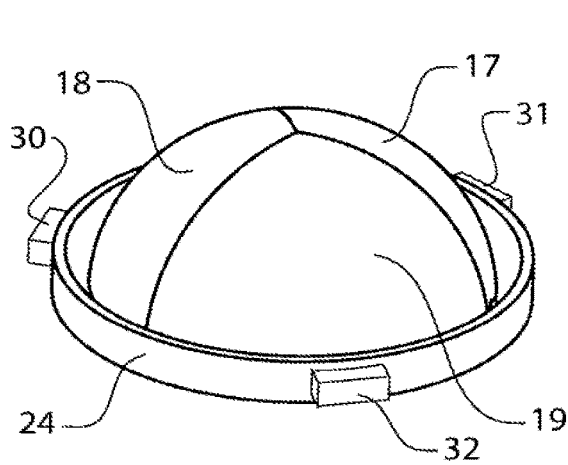
Figure 2D:
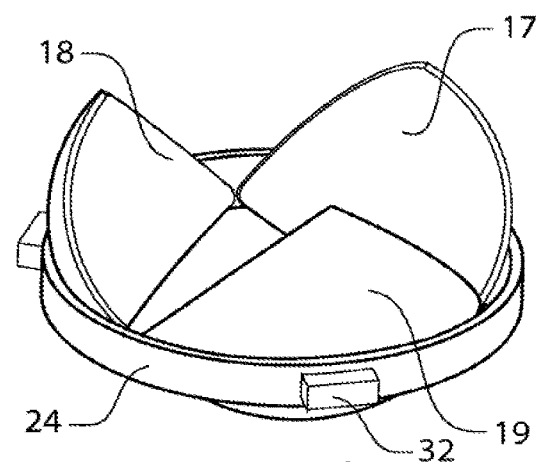
Figure 2E:

FIG. 2a shows the valve 20 closed in a plan view, FIG. 2b shows the valve 20 closed in a "profile" view, and FIG. 2c shows the valve 20 closed in a side view. FIG. 2d shows the valve 20 open in a side view, and FIG. 2e shows one of the moving parts 17 with its hinges 21, 21'

In the following, the valve of the invention will be described mainly with reference to the embodiment 20, which is done to facilitate the reader's understanding, and should not be seen as excluding the other embodiments shown in, for example, FIGS. 1a-1d.

Figure 3A:
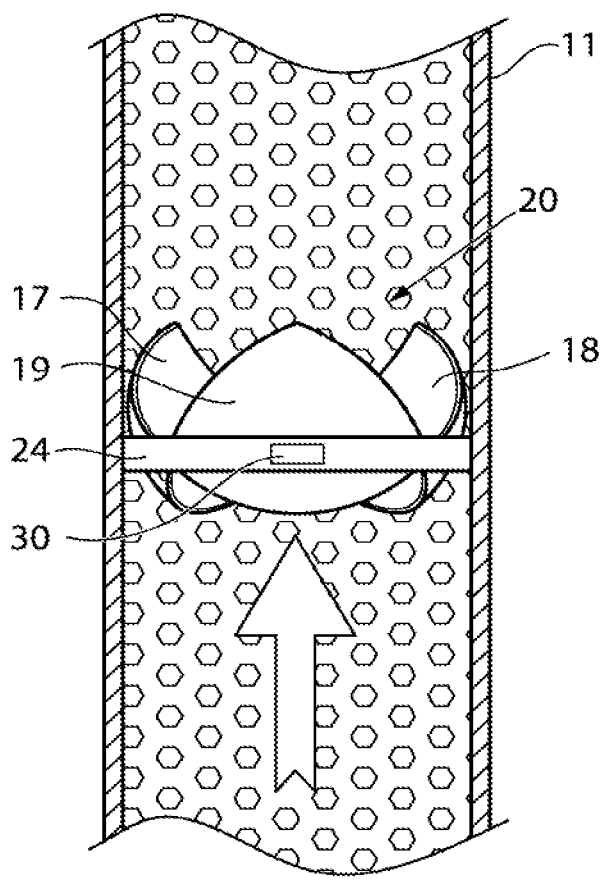
FIGS. 3a and 3b show cross sections of a blood vessel with an implant of the invention.
Figure 3B:
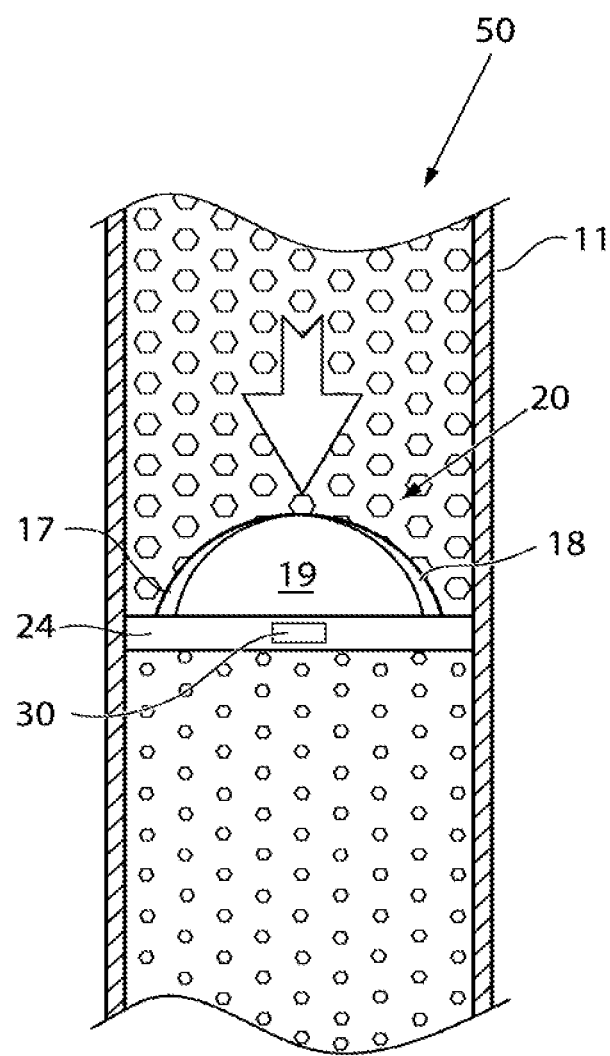

As mentioned previously, and as is shown in FIGS. 3a and 3b, the valve 20 is intended to be fitted into a mammal blood vessel 11 in such a way that the blood in the systolic phase will flow against the inside of the cupola, as indicated by means of an arrow in FIG. 3a, and in the diastolic phase, as shown in FIG. 3b, the blood will flow backwards against the outside of the cupola parts.

Thus, in one embodiment of the present invention, in the valve 20, the moving parts 17, 18 and 19 are adapted to be opened by the blood flow, and in one embodiment, the moving parts 17, 18 and 19 are adapted to be closed to the cupola position by the blood flow, since the blood flow in the systolic phase will cause a pressure to be brought against the moving parts 17, 18, 19 in their closed position, which will cause the moving parts to move about their hinges to assume their open position, and in the diastolic phase, the blood will begin to flow in the opposite direction, which will cause the moving parts to move about their hinges to assume their closed "cupola position".

In one embodiment, the moving parts 17, 18 and 19 are adapted to be opened and/or closed by blood pressure of a certain pre-defined level which differs from the level at which a valve normally opens and/or closes. The term "blood pressure" should here be seen as a difference in pressure between the "two sides" of the valve 20: in the closed position, the difference between the pressure on either side of the cupola, and in the open position on either side of the casing 14. This will be explained in the following.

These alternative embodiments, i.e. those in which the valve 20 is opened and/or closed by the flow or pressure of blood at a level which is higher than that which opens/closes a traditional valve, may be advantageous to, for example, patients with reduced circulation and oxygen supply in the coronary arteries, as explained in the following: in the systolic phase, in the "normal" function of a mammal, blood flows from the heart through the valve, which opens due to the increased blood pressure in the systolic phase.

However, if the inventive valve 20 is placed in the aorta between the exit to the coronary arteries and the exit to the carotid arteries, as opposed to a natural valve and known artificial valves, which are placed before the coronary arteries, the embodiment of the present invention in which the valve is made to open at a blood pressure which differs from that at which a natural valve opens, will be advantageous, due to the fact that in this embodiment, the valve can then be made to remain closed slightly longer than a valve with the "normal" function, i.e. a valve which opens more or less instantly as the blood pressure mounts. The difference in the opening pressure of the inventive valve as compared to a natural valve is thus in this embodiment that the inventive valve opens at a slightly higher pressure than the normal valve.

Since the inventive valve in this embodiment remains closed slightly longer than a "normal" valve, the blood pressure on the "heart side" of the valve will build up to a level which is higher than the blood pressure which causes a normal valve to open, which in turn will cause an increased amount of blood to flow into the coronary arteries.

Figure 4:
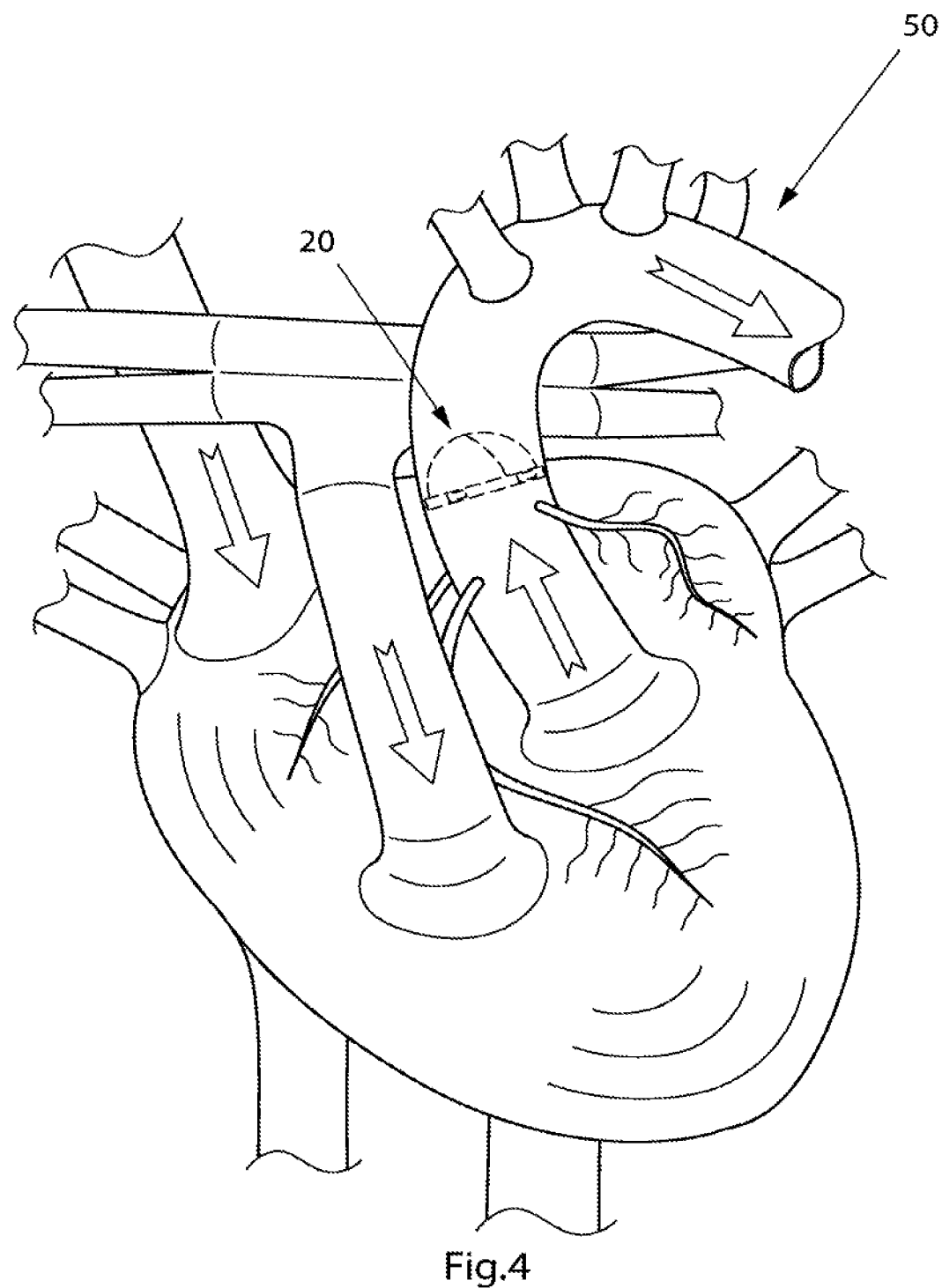
FIG. 4 shows a mammal heart with an implant of the invention.

FIG. 4 schematically shows a valve 20 inserted in the position described above in a mammal heart, i.e. in the aorta between the exit to the coronary arteries and the exit to the carotid arteries.

In this embodiment, the valve 20 is thus caused to remain closed slightly longer than normal, which is achieved by means of letting the valve comprise a resistance mechanism by means of which a "barrier force" of a predetermined level is needed to initiate the opening movement of the moving parts, so that the moving parts are given an initial moving resistance before the valve opens to allow blood to flow through the valve.

It can be pointed out here that the term "initial moving resistance" is used to signify that once the blood pressure or the blood flow reaches a desired value, the opening of the valve by the blood flow/pressure then takes place with virtually no resistance from the resistance mechanism of the valve 20.

The barrier force will here correspond to a difference in blood pressure between the two sides of the closed cupola valve 20. The exact values of the barrier force can be varied within the scope of the present invention, but a minimum suitable value has been found to be equal to or greater than that caused by a blood pressure (difference) of 10 mm Hg, or in the interval of 10-30 mm Hg.

Turning now to the resistance mechanism which causes the moving parts 17, 18, 19 to offer the barrier force against opening, this mechanism can be designed in a number of ways, but will suitably comprise a spring mechanism. Suitably, the spring mechanism is adapted to act on the hinges of the moving parts 17, 18, 19, so that the spring mechanism may in fact be a spring which is integrated into the hinges.

In another embodiment, the resistance mechanism comprises one or more springs which act on the moving parts to cause the desired barrier force effect.

As an alternative, the resistance mechanism can comprise a "step mechanism" in order to create a "barrier force" to be overcome by the opening movement of the moving parts, and which will thereafter not substantially brake the moving parts in their opening movement.

Figure 11A:
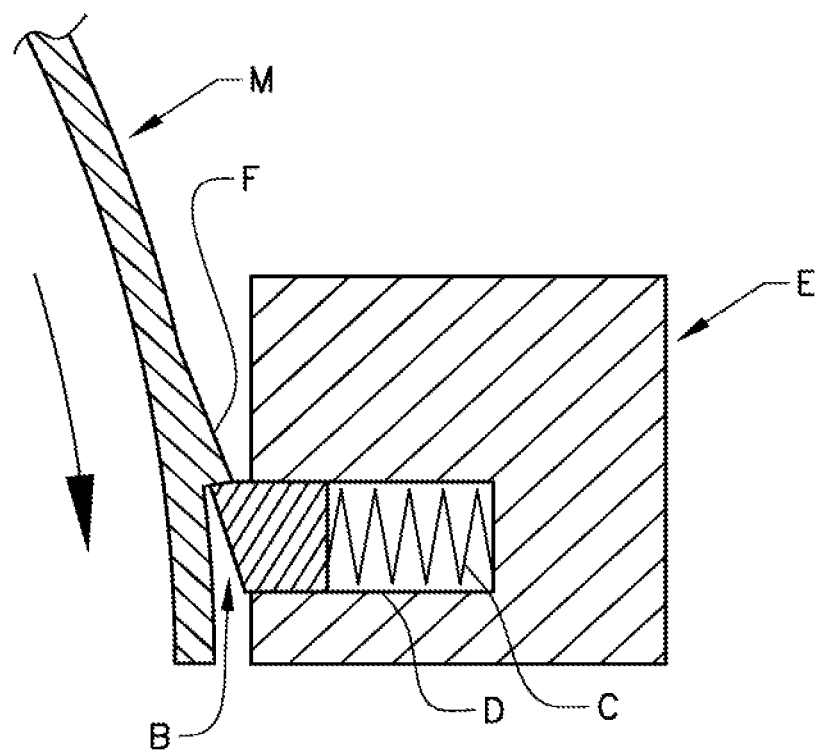
FIGS. 11a and 11b show a barrier force mechanism of the invention.
Figure 11B:
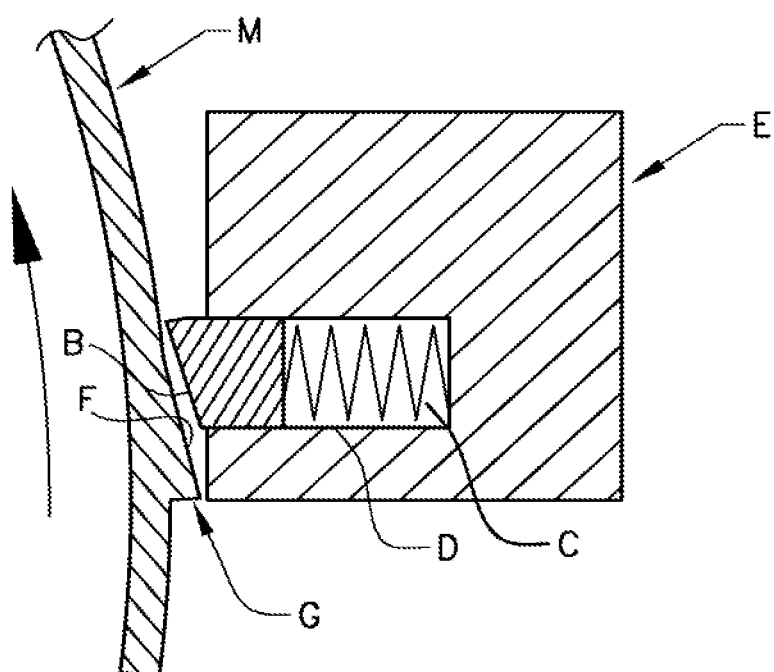

An example of how such a barrier force can be obtained is shown schematically in FIGS. 11a and 11b: one of the moving parts, shown generically as A, comprises a protruding edge F which creates a "step" G on the side of the protruding part which is closest to the casing E.

The casing, in turn, comprises a movable protruding part B, which is lodged in a groove D in the casing, and is attached to the casing by means of a spring C.

Thus, when the moving part A performs its opening movement, shown by the arrow in FIG. 11a, it will be delayed in that movement by the contact between the edge G and the movable part/spring mechanism of the casing. Once the step/edge G has cleared the movable part B, however, the braking effect will cease.

As can be understood, the opening resistance caused by the mechanism of FIGS. 11a and 11b, can be dimensioned to correspond to a certain level of blood pressure or blood flow.

When the moving part A is to carry out an opening movement, FIG. 11b, the outside of the step F will come into contact with the moving part, and will not be "caught" by the movable part B to the same extent as in the opening movement.

Thus, the desired level of resistance force, for example corresponding to 5 or 10 mmHg blood pressure, can be created by means of the passive resistance mechanism described above and shown in the drawings. By means of the barrier force created, which corresponds to a level of blood pressure, the at least one moving part will be opened by the blood flow at said level of blood pressure, and the artificial valve is adapted to let the at least one first moving part move freely after the barrier force has been reached. Thus, in such an embodiment, the passive resistance mechanism is arranged to offer resistance until said predetermined level of the barrier force is reached, or alternatively, the passive resistance mechanism is arranged to only offer resistance in the opening movement of said at least one first moving part.

In the embodiments of the valve which have been described above, the opening and closing of the valve 20 has been passive, i.e. caused without the aid of any external signals and without any external power feed. In other embodiments, which will be described below, the movements of the moving parts 17, 18, 19 for the opening and closing of the valve 20 may involve external signals and powered mechanisms, i.e. uses the supply of power.

Figure 5:
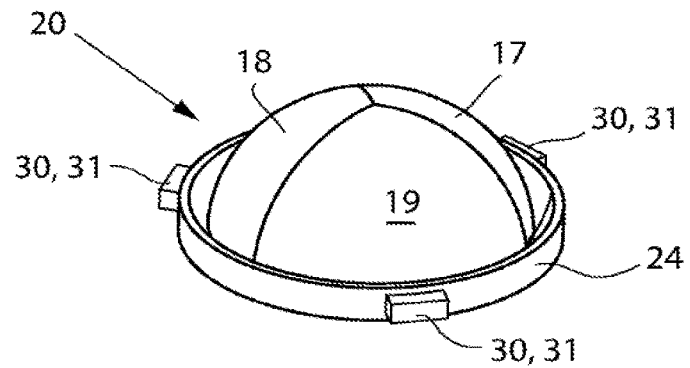
FIGS. 5-10 shows side views of different versions of the third embodiment of the invention.

FIG. 5 shows this in a schematic manner: the artificial valve 20 of the invention is here shown as comprising an operating mechanism 31, which is adapted to power the moving parts 17, 18, 19 in their movements to the closed and/or open position, so that the closing and/or opening of the valve is active. This powering is carried out at least in part by means of a power source external to said blood vessel, said power source not being shown in FIG. 5. As shown in FIG. 5, the operating mechanism can suitably be divided into parts, with one part for each of the moving parts 17, 18, 19.

The valve 20 may also comprise a receiving device 30 in order to receive a closing and/or an opening signal, which will also supply this signal to the operating mechanism 31 so that the operating mechanism will cause the moving parts of the valve to close and/or to open when the operating mechanism 31 receives the signal from the receiving device 30.

In one embodiment, as shown in FIG. 5, the operating mechanism 31 and the receiving device 30 are integrated into one physical unit, while in other embodiments the operating mechanism and the receiving device are separate physical units.

It should be understood that the alternatives of active and passive opening and closing of the valve 20 may be combined with each other as desired. Thus, for example, the following combinations are possible in the valve 20 of the present invention:
1. Active closing, active opening.
2. Active closing, passive opening.
3. Passive closing, passive opening.
4. Passive closing, active opening.

Figure 6A:
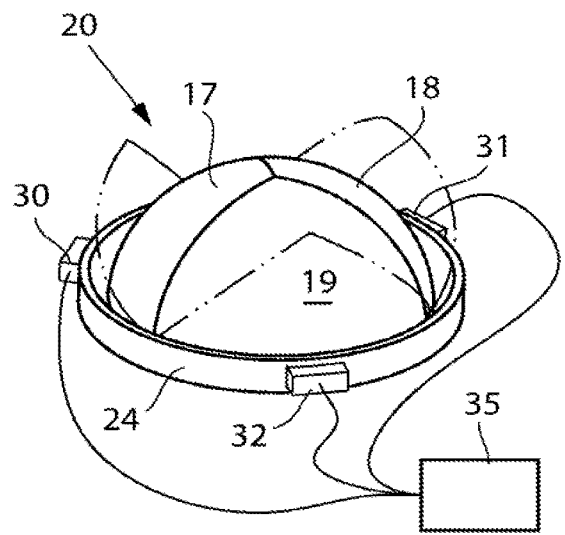
Figure 6B:
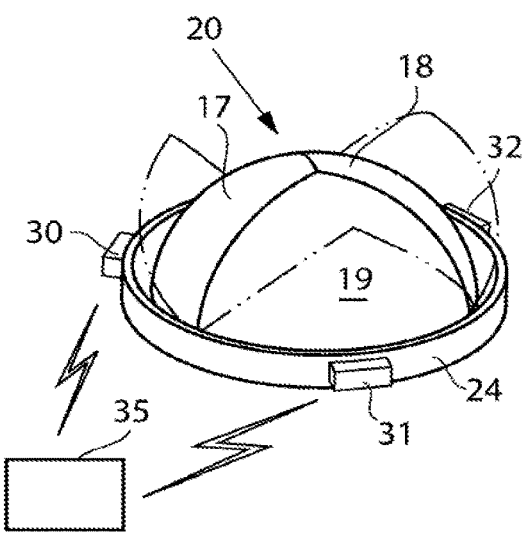

The exact design of the receiving device 30 may vary, but in a preferred embodiment, the receiving device is adapted to receive the opening and/or closing signal as an electrical signal. The signal may be received via cabling which is connected to the receiving device, or it may be received wirelessly, i.e. as radio signals, so that the receiving device 30 comprises a wireless receiver. These embodiments are shown in FIGS. 6a and 6b, with FIG. 6a showing the signal being received via cables, and with FIG. 6b showing the signals being received wirelessly by the receiving device 30.

In both of the embodiments of the receiving device mentioned above, i.e. the cable receiver or the wireless receiver, the receiving device will also comprise "interpretation" means for the received signal, so that the received signal may serve as the basis for a decision by the receiving device to open or close the valve, or to keep it open or closed. Suitably this is achieved by means of comparing the received signal to one or more threshold levels to see if the valve should open or close, or remain open or closed. In the case of a wireless signal, the receiving device may also suitably comprise a demodulator for demodulating a received wireless signal.

Turning now to more details of the operating mechanism 31 by means of which the moving parts 17, 18 and 19 of the valve are made to perform the opening and/or closing movements, this operating mechanism 31 can be designed in a large number of ways within the scope of the present invention, as will be obvious to those skilled in the field.

Figure 7:
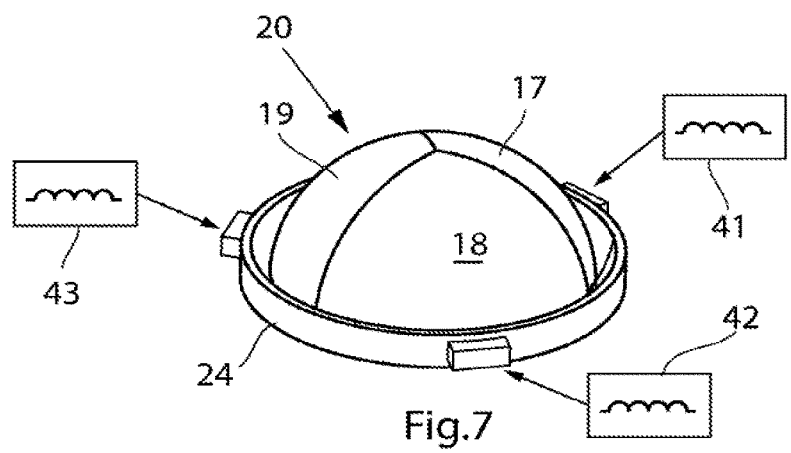

However, as shown in FIG. 7, in one embodiment, the operating mechanism 31 may comprise one or more magnets (not shown) on each moving part, each of which interacts with a coil 41, 42, 43, in order to create a motion of the moving parts 17, 18, 19. As indicated in FIG. 7, each of the coils 41, 42, 43, is preferably arranged on the casing 14 at a central position for each moving part 17, 18 and 19, with each of the interacting magnets being arranged at a position on a moving part which is immediately adjacent to the position of a coil.

In this embodiment, the motion of the moving parts 17, 18 and 19 can be caused by passing an AC current through the coils 41, 42, 43.

Figure 8:
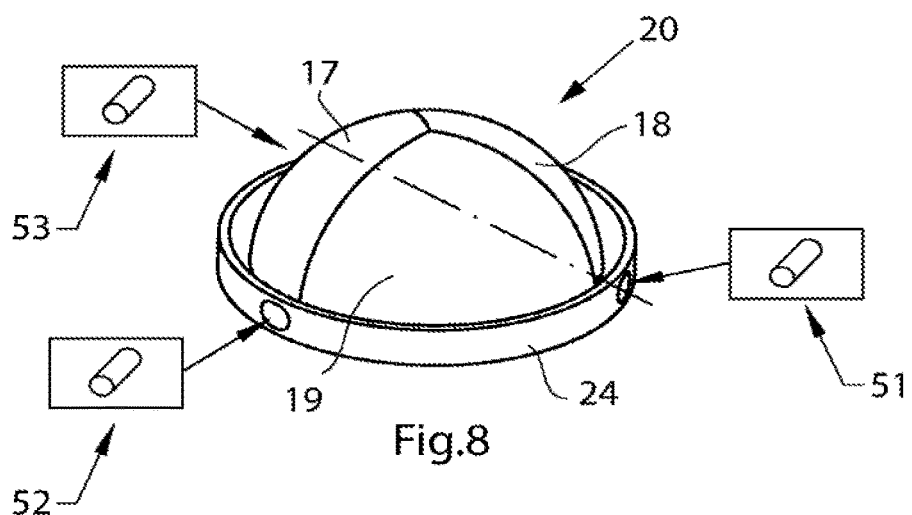

In another embodiment, the operating mechanism 31 comprises a mechanical element which is involved in the opening and/or closing of the valve 20. A suitable example of such a mechanical element is shown in FIG. 8, and comprises one or more rotatable shafts 51, 52, 53, which may, for example, be arranged to interact with the hinges of the moving parts 17, 18, 19 to cause the moving part to open and/or to close.

Suitably, the rotatable shaft is attached to an engine (not shown) which rotates the shaft 51, with the rotation of the shaft being controlled by the signals received by the receiving device.

Figure 14:
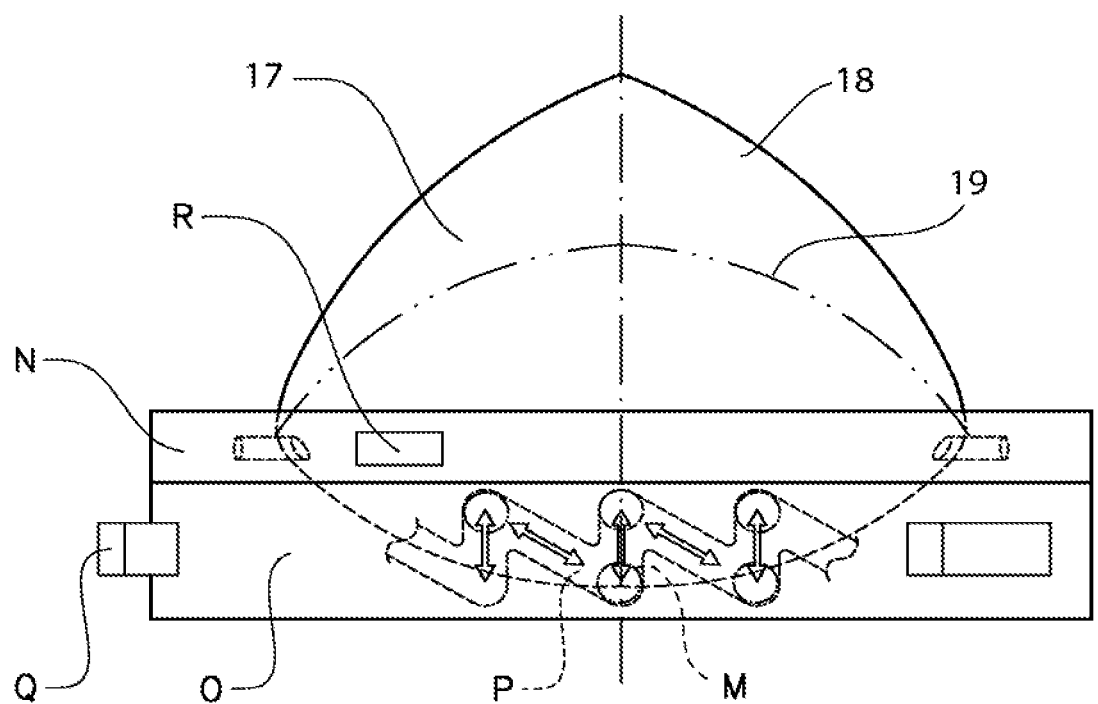

Other embodiments of how the opening and or closing movement of the moving parts may be obtained are shown in FIGS. 12-14 below, and are based on the casing having a first H and second H' casing part, with the first part being displaceable in relation to the second part in order to cause the opening and/or closing movement. Suitably, the first H and second H' casing parts each comprise a ring, with the two rings being concentric to each other, and with one of the first or second rings being adapted to move in relation to the other part in order to cause the closing and/or opening movement.

Figure 12A:
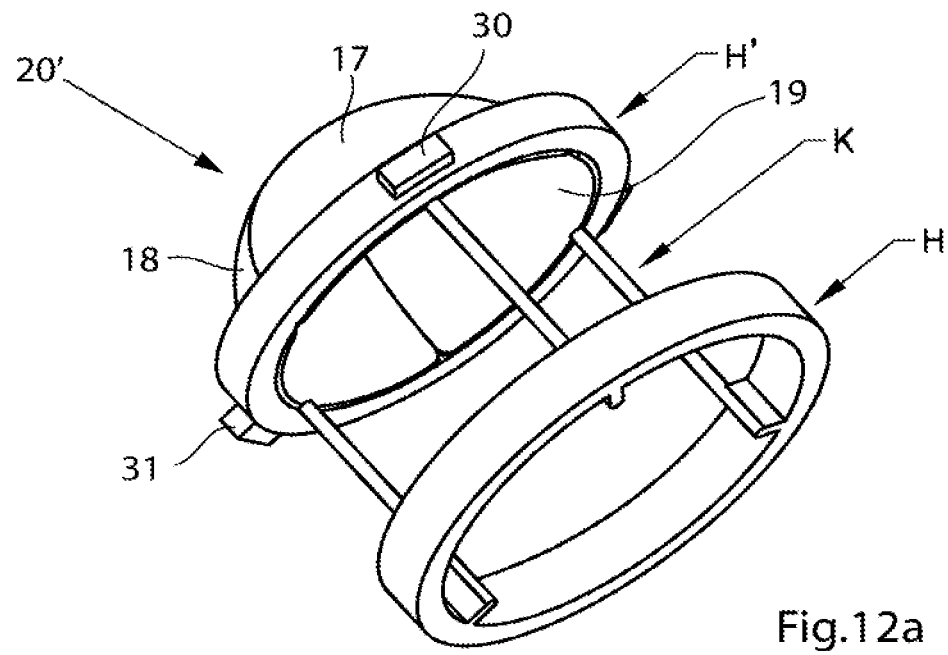
FIGS. 12a-14 show powered movements.
Figure 12B:
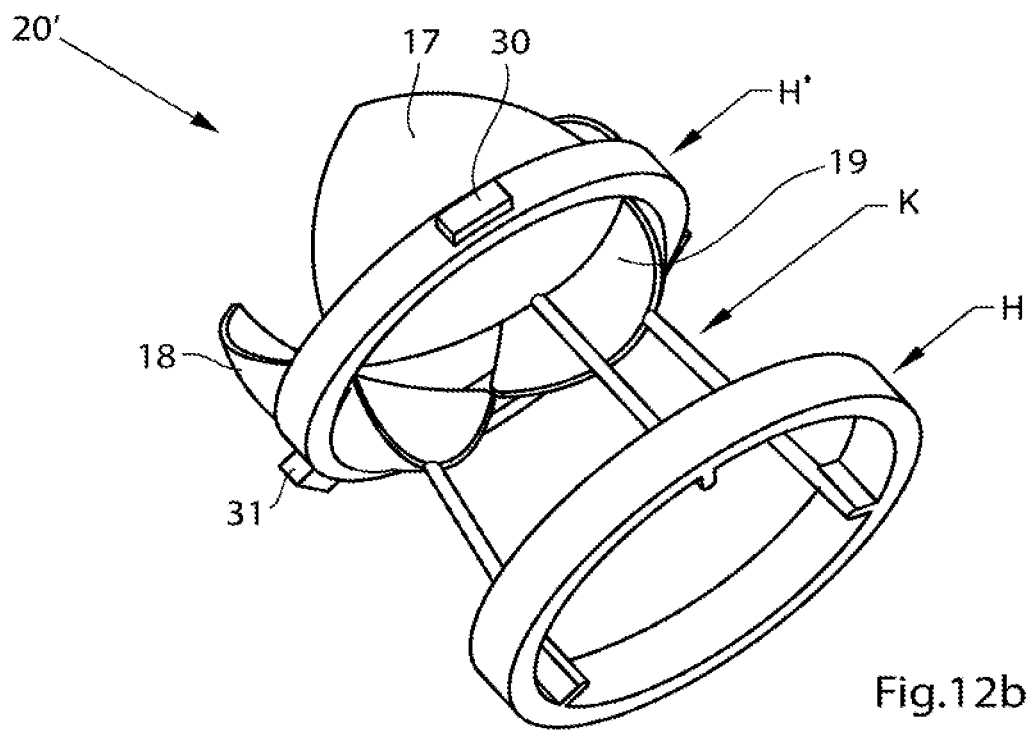
Figure 13A:
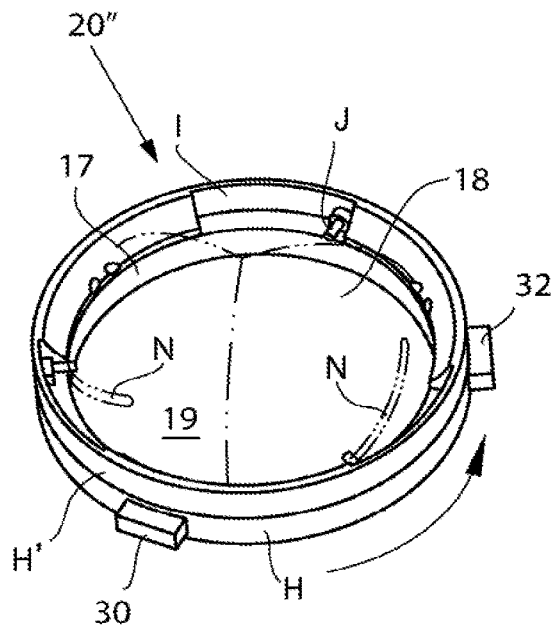
Figure 13B:
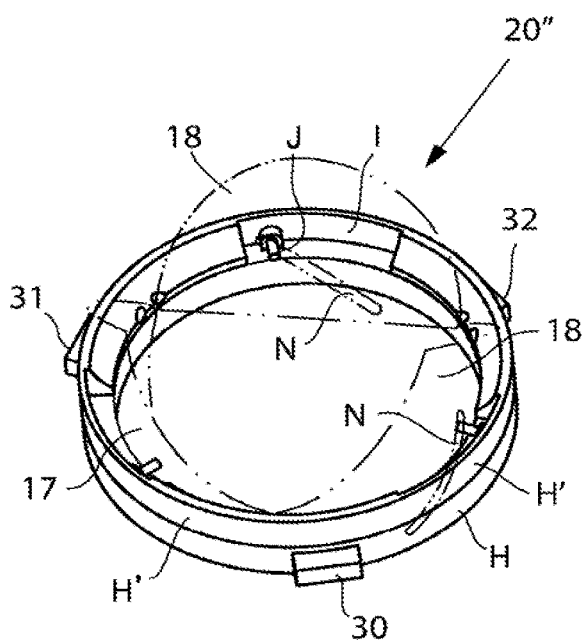
Figure 13C:
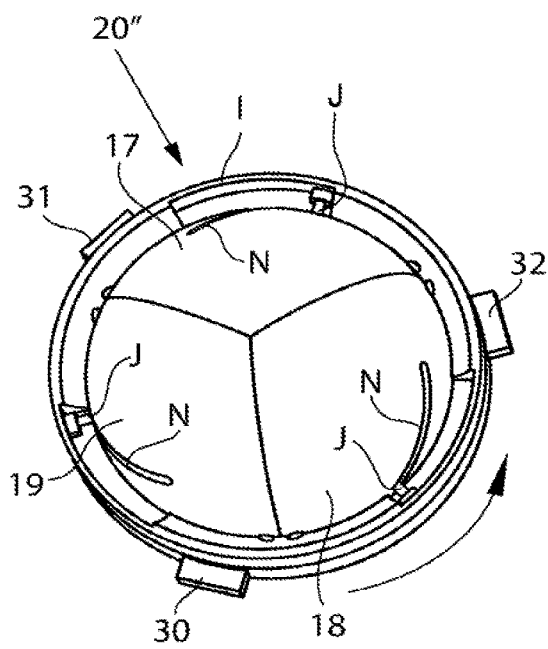
Figure 13D:
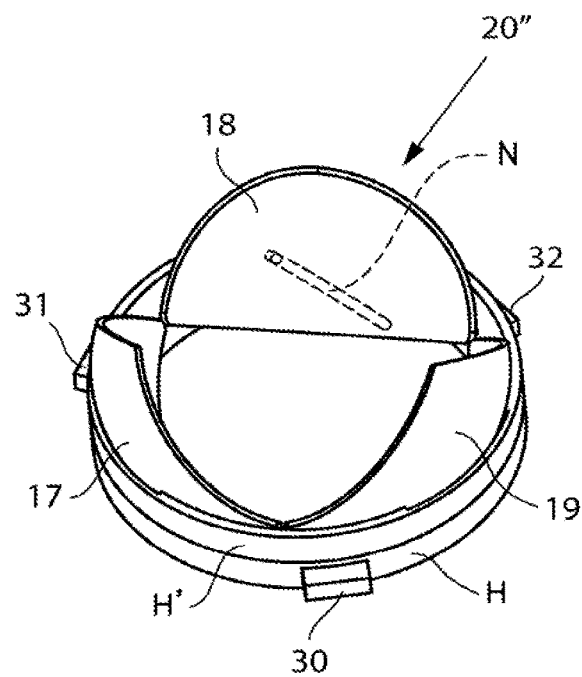

As can be seen in FIGS. 12a and 12b, the two parts H' and H of the casing each constitute rings and can be made to move away from each other or towards each other, i.e. essentially in the direction of the "axis" of a blood vessel. Suitably, only one of the casing parts should be made to move.

In the embodiment of FIGS. 12a and 12b, the ring H, which is the most distant from the moving parts of the cupola, has one end of each of three mechanical elements K, for example three pins, attached to it, with the other ends of the pins being attached to one each of the moving parts of the cupola.

As the distance between the two parts of the casing, H and H', is made to increase or decrease, by means of, for example, magnets and coils, the pins will cause the cupola parts to move about their hinges and open, FIG. 12b, or close, FIG. 12a.

FIGS. 13*a*-13*d* show another embodiment in which the casing parts are also concentric rings H', H. However, in this embodiment, the opening and/or closing movement of the cupola parts is obtained by letting the rings rotate in relation to each other, suitably with only one of the rings rotating.

As can be seen in FIGS. 13*a*-13*d*, the ring H which can be made to rotate, for example by means of interaction between springs on one ring and coils on the other, comprises three pins, J, which can move in corresponding openings I of the other ring H'.

As can also be seen in FIGS. 13*a*-13*d*, the cupola parts comprise a groove N (not a through-going groove though) in which the pin J can run. The groove N is slanted in the cupola part, so that rotation of the ring H with the pins J will cause the cupola parts to open or close, depending on the direction of rotation of the ring H.

FIG. 14 shows another embodiment of how the cupola parts may be made to open and/or close actively as well as passively; in this embodiment as well, the casing comprises an upper N and a lower O ring shaped part, which are essentially concentric.

One of the ring shaped parts, O, comprises a groove P, which consists of vertical and slanted parts, in an alternating fashion. A pin M from each cupola part runs in this groove. If the blood pressure increases, the cupola part will open, since the pin will move in a vertical (i.e. essentially parallel with the extension of a blood vessel) part of the groove, and can also be closed when the blood begins to flow in the reverse direction, i.e. during the diastolic phase of the heart.

However, if the ring O with the groove P in it is made to rotate, the pin will be forced to move in or by a slanted part of the groove, which will also cause the cupola part to perform a closing or opening movement, depending on the direction of rotation of the ring. A mechanism for making the ring O rotate is indicated as Q in FIG. 14.

Before the signals which are received by the receiving device 30 are described in more detail, an advantage of a valve 20 of the invention with an active closing mechanism will be described:

One advantage of the embodiments of the valve 20 which employ active closing is as follows: known valves, either natural valves or artificial valves of known designs, will close due to the reverse flow of the blood. In other words, when the systolic phase of the mammal's heart ceases, the blood in the vessel will begin to "flow backwards", i.e. in the direction which is opposite to the direction of the flow during the systolic phase, which will cause a known valve, natural or artificial to close. However, before the known valve closes in this manner, a certain amount of blood will have passed through the valve in the "back" direction, which will reduce the efficiency of the systolic phase of the heart.

For patients with, for example, a reduced heart function, this reduction in efficiency may be critical. However, a valve 20 of the invention which has an active closing mechanism may be adapted to close more or less as soon as the systolic phase of the heart ceases and the diastolic phase begins, which will thus increase the efficiency of the heart.

If the application of the valve 20 is to help increase the heart's efficiency in this way, the signals received by the receiving device 30 will be signals relating to the heart's various phases, and/or to the blood flow or pressure in the vessel, since the signals to the receiving device which initiate the active closing may be caused by a sensor which senses that the blood has begun to flow in the "back direction", or that the blood pressure reaches a value which indicates a transition between systolic and diastolic heart phase.

It will also be seen that active closing of the valve 20 has a built-in auxiliary mechanism: if the active closing mechanism for some reason malfunctions, the moving parts 17, 18, 19 of the valve 20 will close in the same way as a natural valve or known artificial valve, i.e. by blood flow in the "back direction".

Turning now to the signals which the receiving device 30 of the valve 20 is adapted to receive, these signals will thus be received from a source such as a sensor or some other device which is external to the valve 20, said source however being connected to the receiving device, for example by means of cabling or wirelessly, as described above.

The signals which the receiving device 30 is adapted to receive from this external source may be based upon a variety of parameters, some examples of which will be given below. It should be understood that these signals may also be combined, so that the receiving device receives input from more than one source or from more than one measurement:

In one embodiment, the receiving device 30 of the valve 20 is adapted to receive input signals which are the result of the blood pressure or blood flow at a defined point in the circulatory system of the user of the valve reaching a predetermined threshold. For example, as described above, this signal may indicate that the difference in blood pressure on the two sides of the closed cupola valve exceeds a certain defined threshold value, which thus signals that the cupola parts should be opened.

In one embodiment, the receiving device 30 of the valve 20 is adapted to receive inputs signals as the result of a parameter which is related to the contraction of a muscle at a defined point in the user of the valve reaching a predetermined threshold. For example, this may be a measurement of the heart's phases, so that the valve 20 is made to open and/or to close at predefined points in the systolic and diastolic phases of the heart.

In general, with regard to the valve operating in conjunction with the heart in a predefined manner, the input signals to the receiving device 30 may be received as the result of one or more predefined body generated parameters which is/are related to the contraction of a heart muscle reaching a predetermined threshold. Examples of such parameters are those mentioned, such as blood pressure, heart contractions (for example movement or bending or volume) or heart electrical body generated signals.

In one embodiment, the artificial valve 20 is adapted to cooperate with another device used by the mammal in question. Thus, in such an embodiment, the receiving device 30 is adapted to receive said input signals as the result of a device generated signal, suitably related to the contraction of the heart. An example of such a device may be a so called pacemaker, and in this case, the input signals would be signals which indicate that the mammal's heart has reached a certain phase at which the artificial valve 20 should open or close. Such a device is shown as 35 in FIGS. 6*a* and 6*b*

As described above, the valve 20 may thus be designed to cooperate with an external device such as a sensor or a device used by the user, such as a pacemaker. However, in alternative embodiments, as a complement or replacement to external sensors and devices, the valve 20 will in itself comprise a sensor for sensing one or more parameters, such as a physical parameter of the mammal or a functional parameter of another device, such as, for example, the parameters enumerated above; such a sensor will then also generate input signals to the receiving device of the valve.

Figure 9:
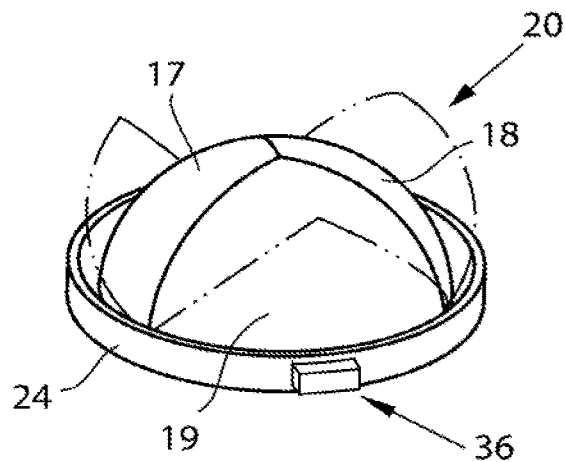

An embodiment of a valve 20 with a built in sensor is shown in FIG. 9, with the sensor being shown as 36.

Figure 10:
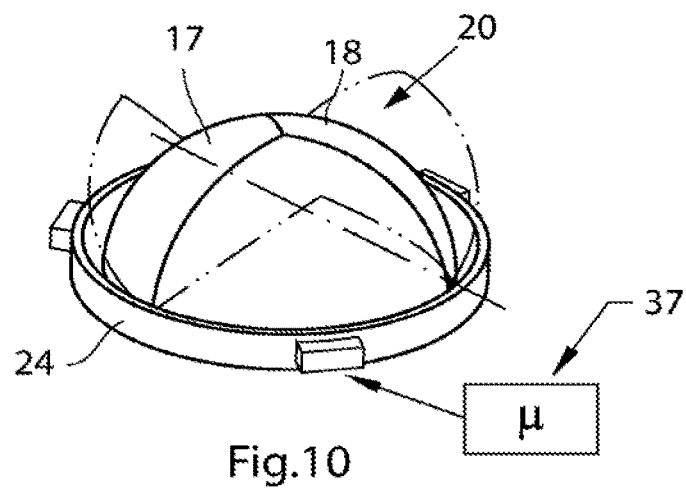

In one embodiment, as shown in FIG. 10, the valve 20 also comprises a control device 37 which will control the operating mechanism 31 in order to control the opening and closing of the valve, i.e. the movement of the moving parts 17, 18 and 19 of the valve 20'. In this embodiment, the control device 37 receives the input signals instead of or via the receiving device 30, processes the signals, and controls the operation of the valve accordingly.

As indicated in FIG. 10, such a control device 37 suitably comprises a processor of some kind, for example a microprocessor, as well as a memory for storing executable code, and possibly also for storing parameters which are relevant to the operation of the valve 20, e.g. threshold parameters such as those mentioned above, etc.

Suitably, the control device 37 controls the operating mechanism 31, using input parameters which are received via a receiving device 30 and/or sensed by an internal sensor, shown as 36 in FIG. 9.

In the embodiments with a sensor and a control mechanism, the sensor is thus adapted to sense a physical parameter of the mammal or a functional parameter of a device such as a pacemaker, and the control device controls the operating mechanism using parameters sensed by the sensor.

As mentioned previously, the operating mechanism of the valve 20 will in one embodiment comprise at least one magnet and at least one coil which interact with each other in order to cause an opening and/or closing movement of at least one of the moving parts 17, 18 and 19 of the valve 20.

In an alternative embodiment, as a complement or alternative to the spring/coil mechanism, the operating mechanism is attached to the casing and comprises at least two parts, with a first part being adapted to move in relation to a second part to cause an opening or closing movement of said moving parts. Suitably, the first part is then the rotating shaft mentioned previously, which is adapted to rotate perpendicularly along the periphery of the blood vessel in which the valve may be implanted.

Regarding the choice of material for the parts of the valve 20, the moving parts 17, 18 and 19 are suitably made of titanium, but any suitable material could be used; and the casing may preferably be manufactured in a ceramic material, but for example stainless steel or plastic materials can also be used. The hinges may be manufactured in titanium, stainless steel, plastic material or ceramics or any combination thereof.

In one embodiment, the moving parts of the valve are at least partially given a structured surface, i.e. a surface which has a pattern or a texture on it, since this has been found to facilitate the growth of mammal material upon a surface.

In one embodiment, the moving parts of the valve are at least partially covered by mammal valve material, such as that taken from a cow, a pig or a human being.

As shown in the drawings, the moving parts of the cupola, which can be two or more, are all essentially equally shaped, so that they represent essentially equal parts of the cupola. This is one embodiment, but embodiments in which the cupola is formed by unequally shaped parts are also within the scope of the present invention, as well as embodiments which use more than three moving parts to form a cupola.

Figure 43A:
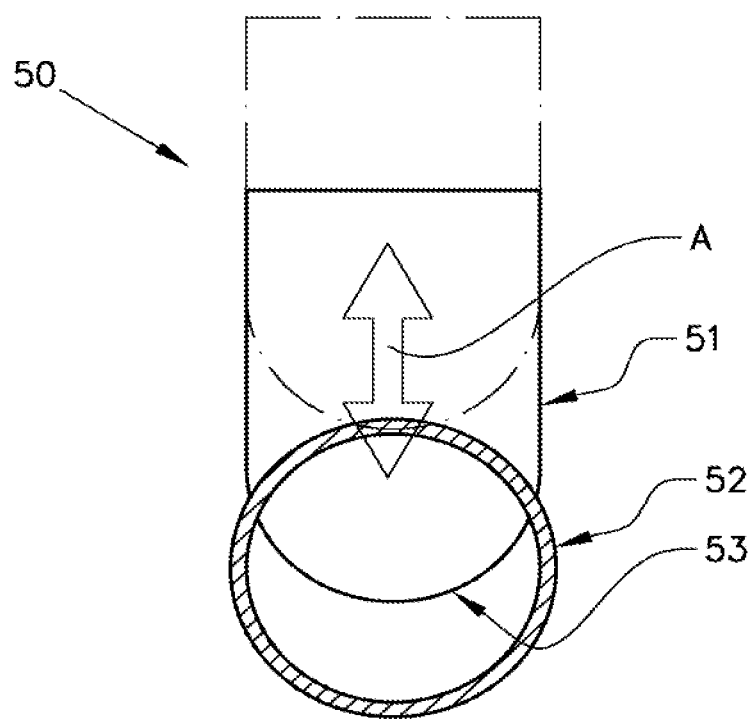
FIGS. 43a-48d show another embodiment of the invention.

FIGS. 43-48 show another embodiment, shown in a plan view in FIG. 43a, together with a blood vessel 52; the closing mechanism of the valve comprises an elongated and essentially flat plate 51 which is adapted to, when the valve 50 is arranged in or adjacent to an opening in the blood vessel 52, move into this opening in a direction which is essentially perpendicular to the blood vessel in order to limit or close the blood flow through said vessel. The direction of movement of the plate 51 is indicated by means of an arrow "A" in FIG. 43a.

As can be seen in FIG. 43a, in one embodiment, the flat plate 51 is given a curved or semicircular shape at the end 53 of the plate 51 which will be the first to enter an opening in the blood vessel 52 during a closing movement, and by means of the curved shape of the end 53, the plate 51 is then adapted to fit against a distal inner wall of the blood vessel 52 in order to close or limit the passage of blood in said blood vessel.

Figure 43B:
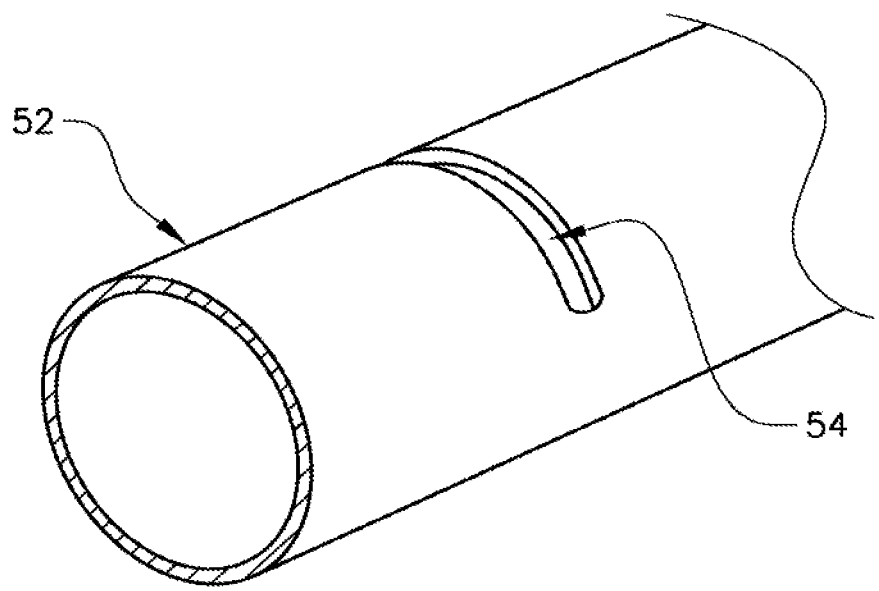

The blood vessel 52 is shown in a perspective view in FIG. 43b, together with an opening 54 which is made in the blood vessel in order to admit the plate 51.

Figure 44:
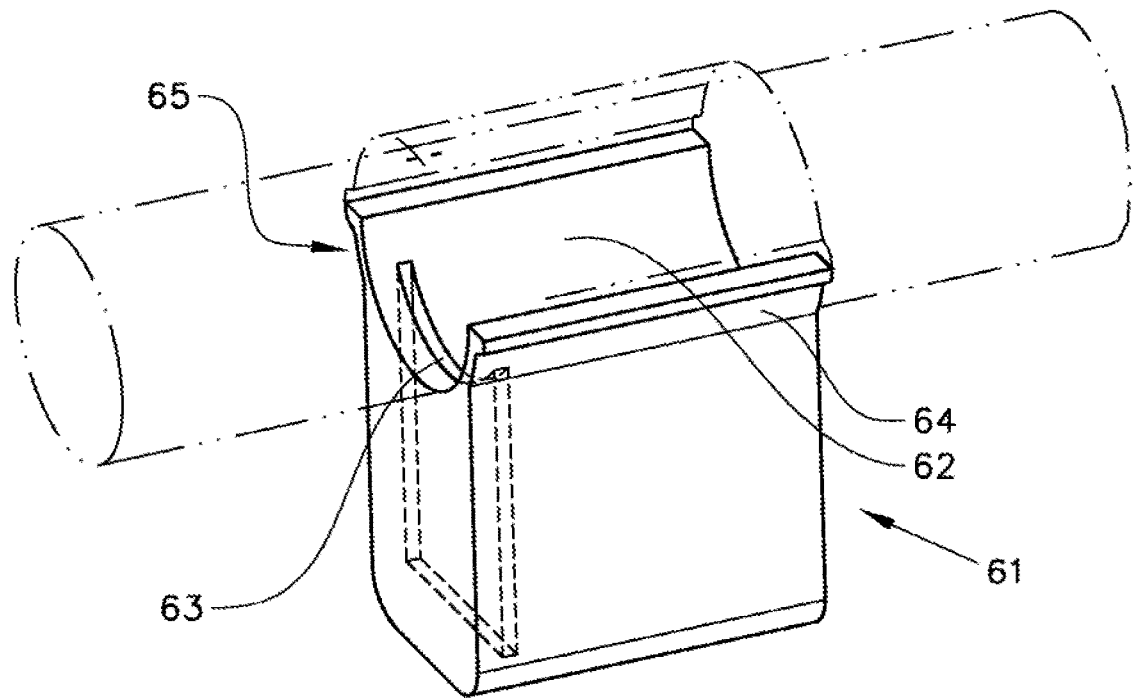

The flat plate 51 is arranged in or adjacent to a casing 61, which is shown in a perspective view in FIG. 44. As can be seen in FIG. 44, in one embodiment, an outer wall 62 of the casing 61 is concavely curved so that it will essentially coincide with the outer shape of a blood vessel against which the casing 61 will be arranged. The curved outer wall 62 also comprises an opening 63 for the plate 51, through which opening the plate can move in its movements. In this embodiment, the tolerance between the dimensions of the opening and the plate should be such that the movements of the plate 51 are enabled, but also such that leakage of blood between the plate 51 and the opening 63 is essentially eliminated.

In one embodiment, also shown in FIG. 44, in order to make it possible to attach the valve 50 securely to a blood vessel, the casing 61 also comprises at least a first curved protruding part 64 for surrounding at least part of the circumference of a blood vessel. In another embodiment, the casing 61 also comprises a second curved protruding part 65 for surrounding at least part of the circumference of a blood vessel, so that the two parts 64, 65 may be arranged on opposite sides of a blood vessel to which the valve 50 is to be attached.

Figure 45:
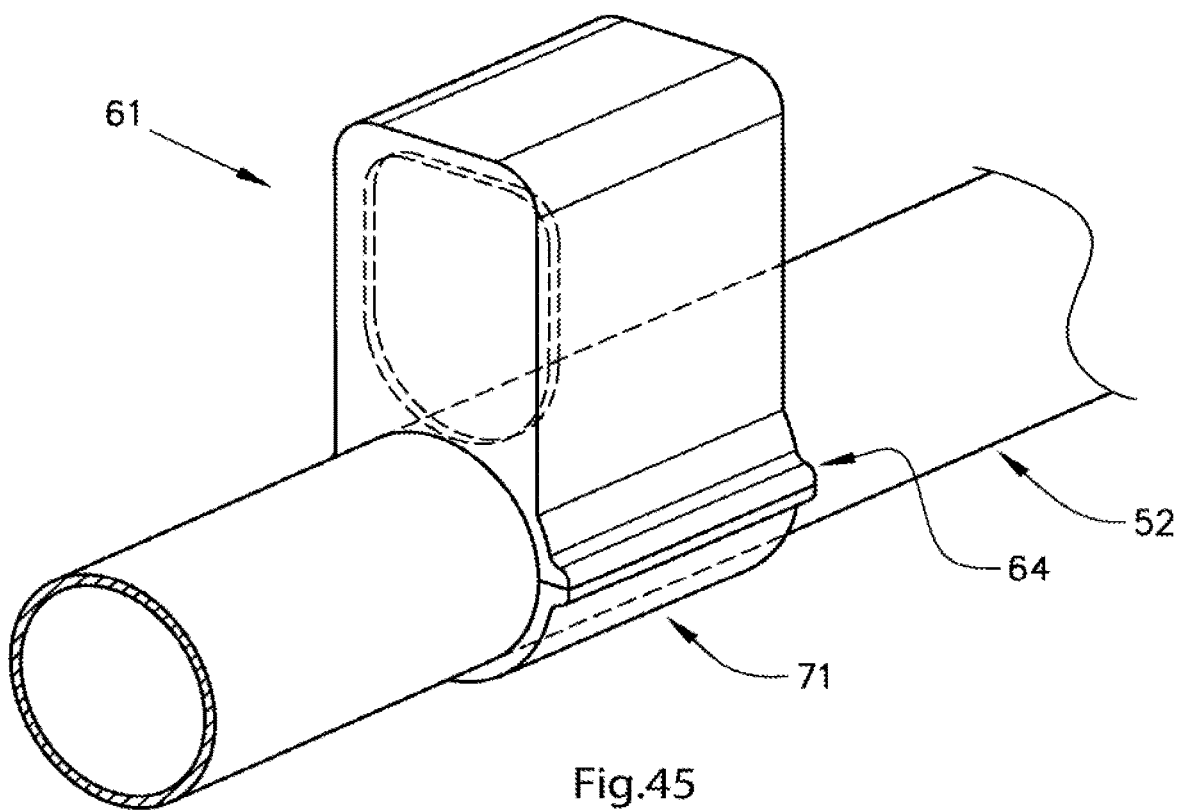

In some patients or in some positions in a patient's body, it may be possible to attach the valve 50 to a blood vessel 52 by means of letting the casing 61 of the valve surround the blood vessel entirely, which is shown in FIG. 45. For such applications, the valve can be made to also comprise a detachable part 71 for attachment to the casing 61 or to one or more of the protruding parts 64, 65. The valve may then be made to completely surround a blood vessel by means of at least one protruding part and said detachable part and/or by means of a curved outer wall of the valve, as shown in FIG. 45.

In the embodiments with the flat plate 51, the plate will thus in its closing movements move into (and out from, in an opening movement) a position in a blood vessel. In one embodiment, show in a side view in FIGS. 46a and 46b, in order to guide the plate 51 in these movements, the casing 61 of the valve also comprises a protruding guide 81 for guiding the movements of the plate 51 in the blood vessel 52.

The guide 81 is thus intended for being arranged inside the blood vessel 81, and is for that reason essentially shaped to coincide with the outer form of the plate, with a certain tolerance to enable the plate to move in the guide. The guide 81 can be seen as an outer rail for the plate 51, and can comprise grooves for the plate 51 to move in.

Figure 46A:
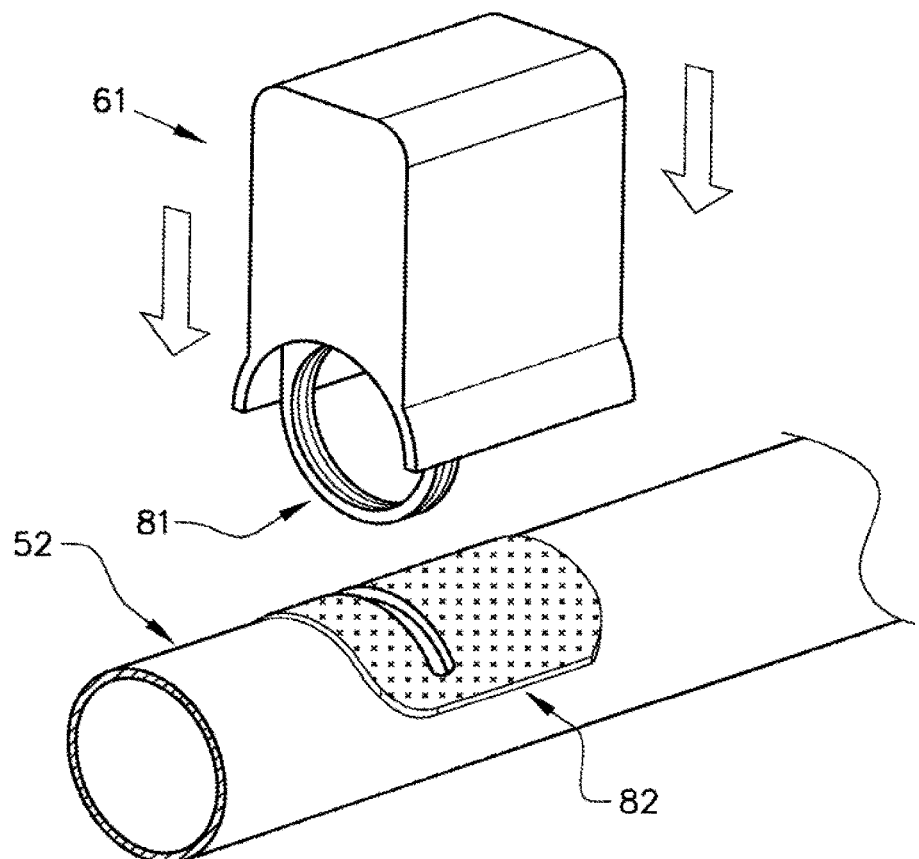
Figure 46B:
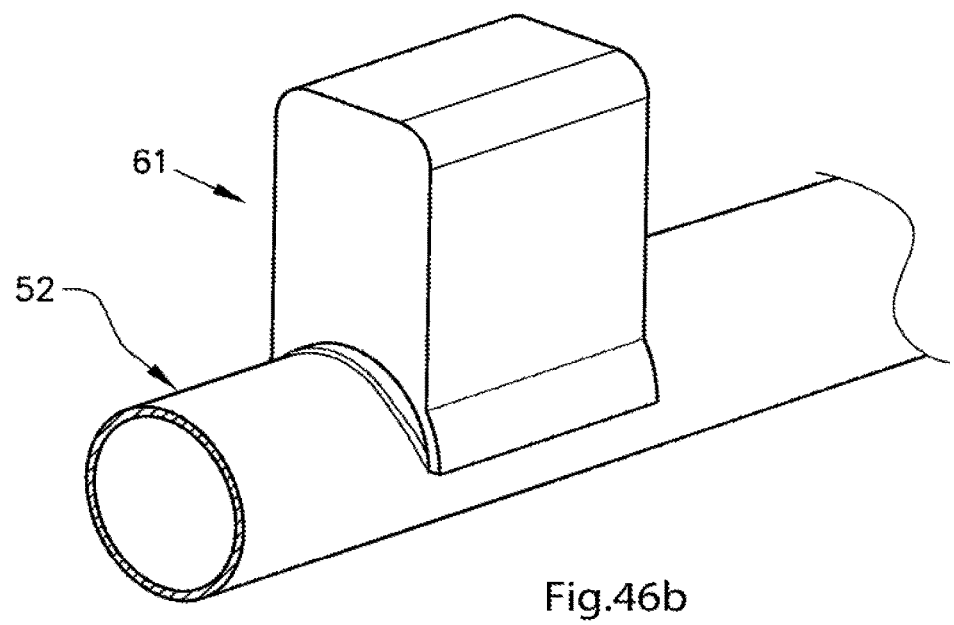

FIG. 46a also shows a vascular graft 82, by means of which the valve may be attached to the blood vessel 52.

Figure 47:
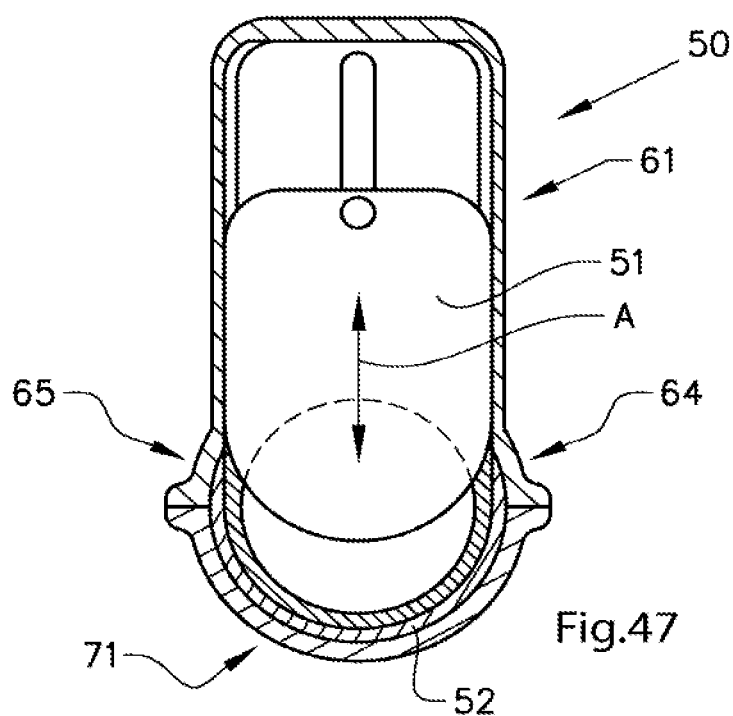

FIG. 47 shows a cross sectional view of a blood vessel 52, adjacent to which a valve 50 of the "flat plate" embodiment has been arranged, with protruding parts 64, 65, to which the detachable part 71 has been attached, so that the casing entirely surrounds the blood vessel 52. The flat plate 51 is also shown in FIG. 9, with its direction of movement being indicated by the arrow "A". As will be realized particularly well from FIG. 47, at least a portion of the moving part 51, i.e. a portion of the "flat plate", will in a non-closed position assume a position external to the blood vessel 52.

In some embodiments, the valve 50 will also preferably comprising a biasing mechanism for biasing the plate to an open position, so that the powered movement has to overcome a biasing force in order to perform the closing movement of the plate 51. Suitably, such a biasing mechanism comprises a spring mechanism. This is shown in FIG. 10, which shows an open side view of the valve 50 arranged adjacent to a blood vessel 52, and shows a possible spring mechanism 82 arranged in the casing 61.

Figure 48A:
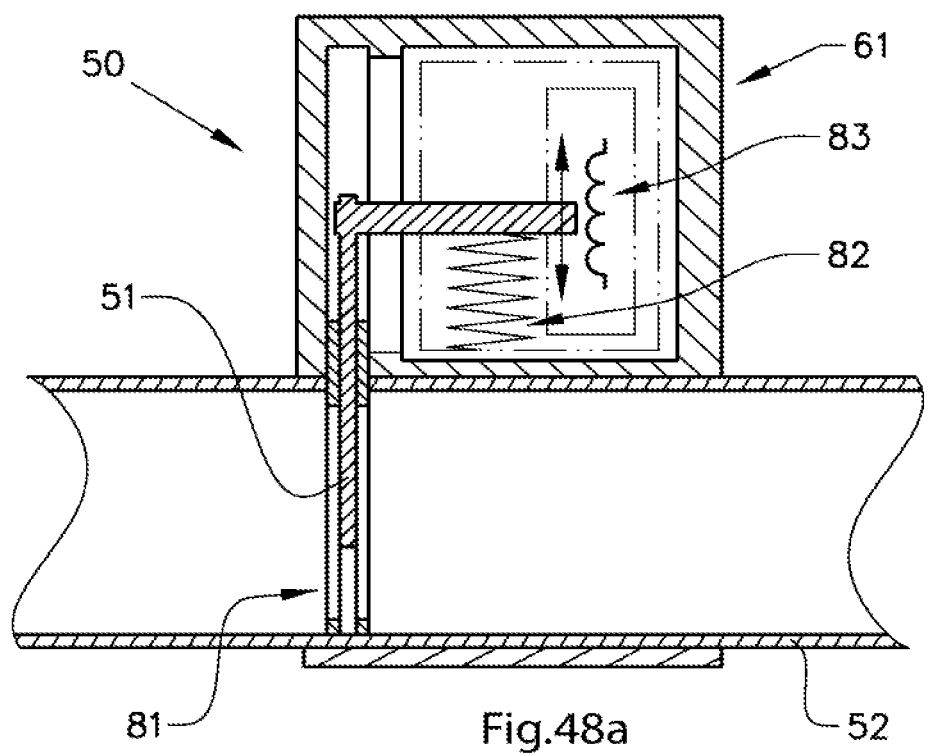

As can be seen in FIG. 48a, the spring mechanism cooperates with an abutment on the plate 51, in order to bias the plate 51 to an open position in the casing 61.

A suitable thickness for the plate 51 is 1 mm, although other thicknesses are also well within the scope of the present invention.

Figure 48B:
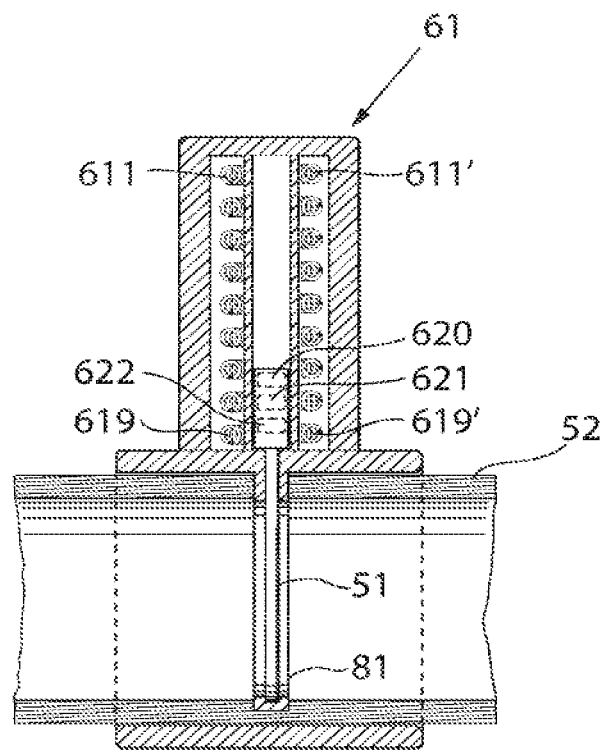
Figure 48C:
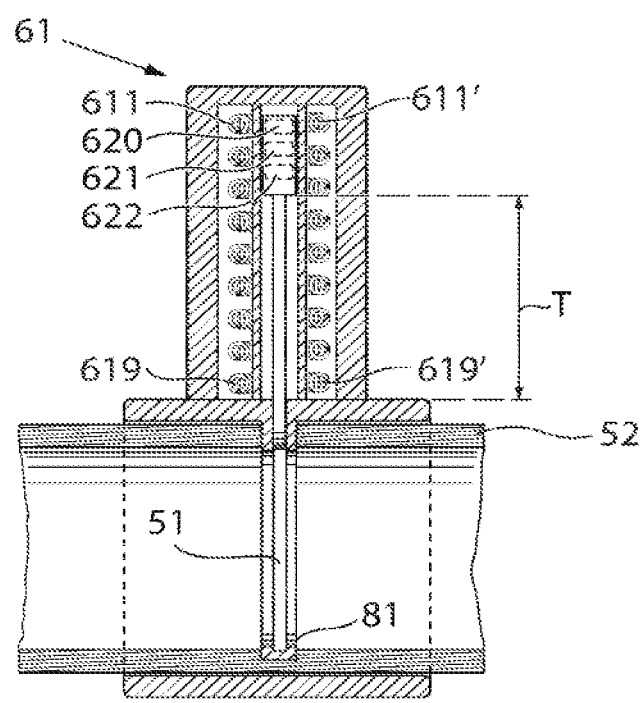
Figure 48D:
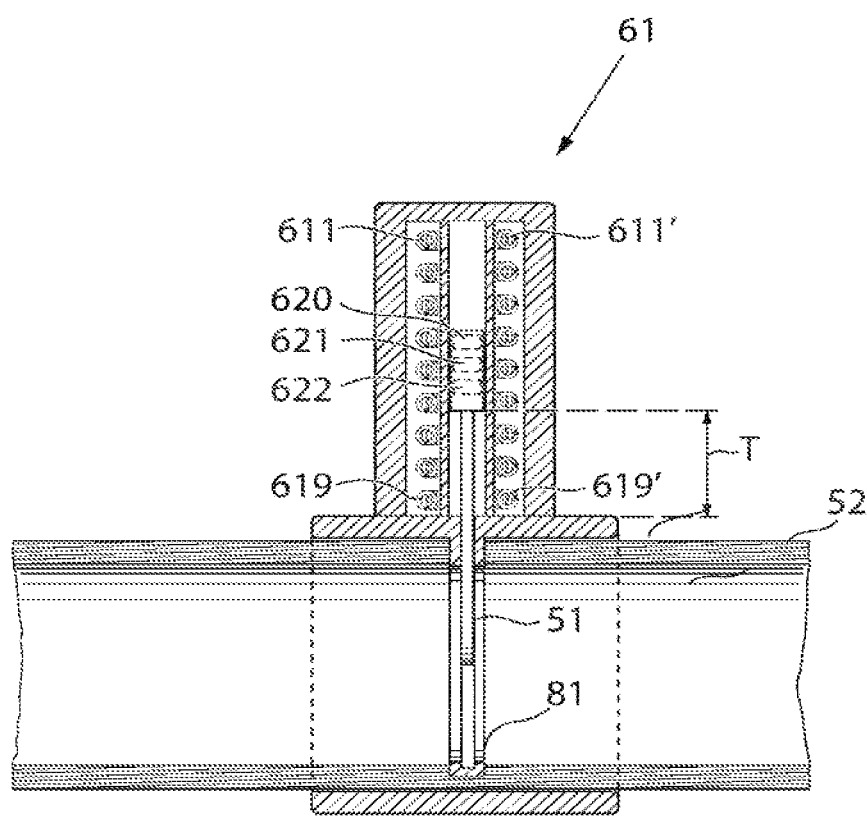
Figure 49:
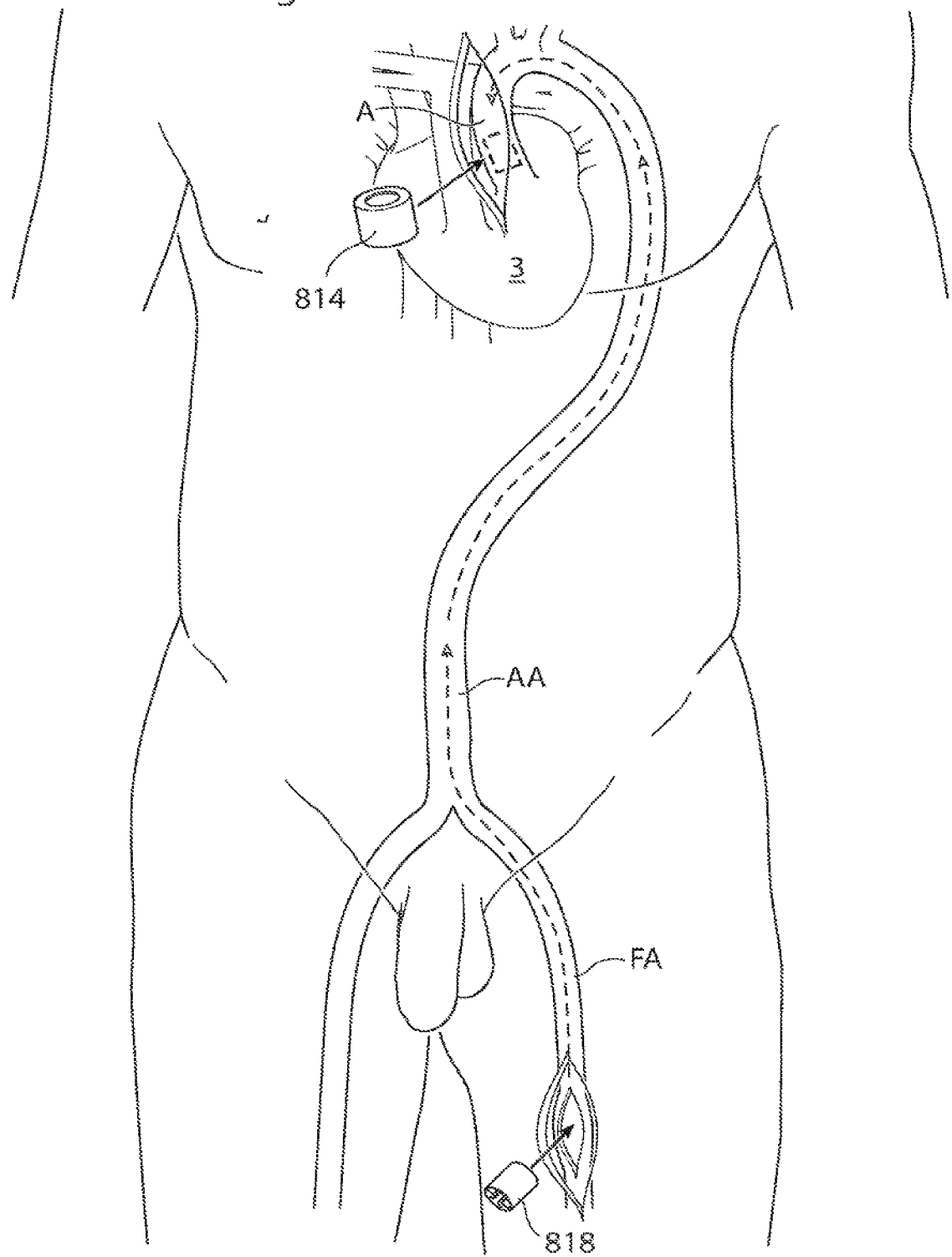
Figure 50:
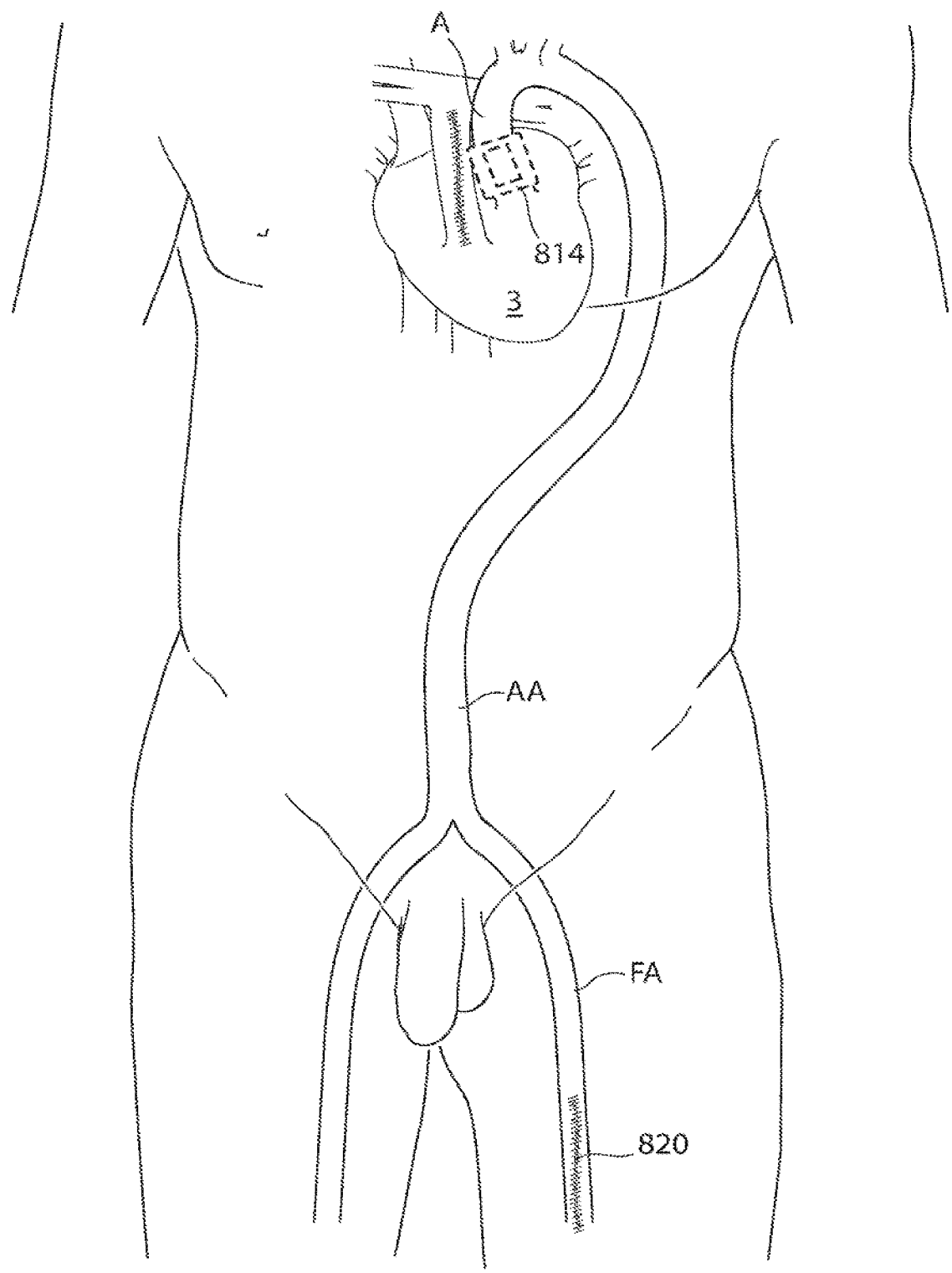

FIGS. 48b-48d show how the movements of the moving part 51 may be powered according to the invention, i.e. from an energy device external to the blood vessel. As shown, the casing 61, or to be more exact, the part or parts of the casing 61 which is arranged to house the moving part 51 outside of the blood vessel 52 is equipped with one or more coils 611-619, 611'-619', which are arranged to be energized by alternating current, AC, so as to interact with one or more magnets 620-622 magnets arranged on the moving part 51. The coils will thus in their interaction with the magnets cause the movement of the moving part 51.

The arrangement for running AC through the coils is not shown in the drawings nor described here, since such an arrangement lies within the scope of what a man skilled in the field has knowledge of.

As mentioned, the following embodiment can, in a non-exclusive manner, be envisioned for a closing mechanism which comprises one or more interacting magnets and coils:
  the closing mechanism comprises at least two magnets, said closing mechanism being adapted to receive said additional pulses to affect a different magnet or a different group of magnets than said first pulse.
  the closing mechanism comprises a coil which is adapted to be energized so as to cause said movement of the closing mechanism.
  the closing mechanism comprises a coil which is adapted to be energized stepwise with two or more energy pulses so as to cause said movement of the closing mechanism.
  the closing mechanism comprises a plurality of coils which are adapted to be energized stepwise so as to cause said movement of the closing mechanism.

Thus, in the "cupola parts" embodiments, the barrier resistance force can be created by means of a passive mechanism such as, for example, the one shown in FIGS. 11a and 11b, while the cupola parts can be closed either passively (not powered) by a return flow of blood in the "relaxation phase" of the heart, or by a powered movement when a parameter has reached a certain value, in which case, for example coils and cooperating magnets can be used to obtain a closing mechanism, and a sensor is used to sense when the parameter in question has reached the correct level for closing.

Regarding the "flat plate" embodiment, both the opening and closing will suitably have to take place as the result of being powered by a mechanism, such as the one shown in the drawings 43-48 and described in connection to those drawings. Such opening and closing suitably takes place as the result of a sensor sensing that a parameter of the patient's body has reached a threshold level, as a result of which the opening or closing movement is initiated and takes place. As an option to a powered opening mechanism, as has been described above, the artificial valve in the "flat plate" embodiment comprises a biasing mechanism which strives to open the valve.

The invention also discloses methods for implanting a valve of the invention into a mammal patient.

According to one embodiment of such a method, the following steps are carried out:
  inserting a needle or a tube-like instrument into the mammal patient's thoraxial or abdominal or pelvic cavity,
  using the needle or tube-like instrument to fill a part of the patient's body with gas, thereby expanding said cavity,
  placing at least two laparoscopic trocars in said cavity,
  inserting a camera through one of the laparoscopic trocars into said cavity.
  inserting at least one dissecting tool through one of said at least two laparoscopic trocars,
  dissecting an area of a potential position for a valve of a blood vessel,
  placing the inventive device in said position in said blood vessel, and
  suturing in steps.

According to another embodiment of a method of the invention, the following steps are carried out
  cutting the skin of the mammal patient
  dissecting an area of the blood vessel
  placing the inventive device in said blood vessel, and
  suturing in steps.

According to another embodiment of such a method of the invention, the following steps are carried out:
  inserting a needle or a tube-like instrument into the patient's thoraxial cavity,
  using the needle or tube-like instrument to fill a part of the patient's body with gas and thereby expanding said thoraxial cavity,
  placing at least two laparoscopic trocars in said cavity,
  inserting a camera through one of the laparoscopic trocars into said cavity,
  inserting at least one dissecting tool through one of said at least two laparoscopic trocars,
  dissecting an area of a heart valve,
  placing a device of the invention in the patient's heart or a connecting blood vessel, and
  suturing in steps.

Another embodiment of a method of the invention comprises the following steps:
  cutting the skin in the thoraxial wall of the mammal patient,
  dissecting an area of the heart valve,
  placing a device of the invention in the patient's heart or a connecting blood vessel, and
  suturing in steps.

The dissection of the two embodiments described immediately above may also comprise the following steps:
  dissecting a path for a cable into the right atrium of the heart
  cutting the skin and dissecting a subcutaneous place for a control unit, similar to a pacemaker position
  introducing the cable backwards from the right atrium of the heart to the position of the control unit following the venous blood vessels. In one version of this embodiment, the cable can be made to reach vein subclavia or vein cephalica and to exit from said vessel.

The method of the invention may also include the step of placing the control device in the subcutaneous area and connecting it to a cable in order to supply the closing and/or opening signal to the valve.

The method may also comprise connecting a power supply for wireless feeding of energy to the valve, in which case the dissection and placing will suitably include the following steps:

dissecting the area outside the heart valve,
placing a wireless control unit including said power supply to wirelessly, supply the closing signal to the artificial heart valve.

The invention also discloses a system for powering and controlling an artificial device or apparatus such as that disclosed by the invention.

In a preferred embodiment, the system comprises at least one switch implantable in the patient for manually and non-invasively controlling the apparatus In another preferred embodiment, the system comprises a wireless remote control for non-invasively controlling the apparatus.

In a preferred embodiment, the system comprises a hydraulic operation device for operating the apparatus.

In one embodiment, the system comprises comprising a motor or a pump for operating the apparatus.

Figure 15:
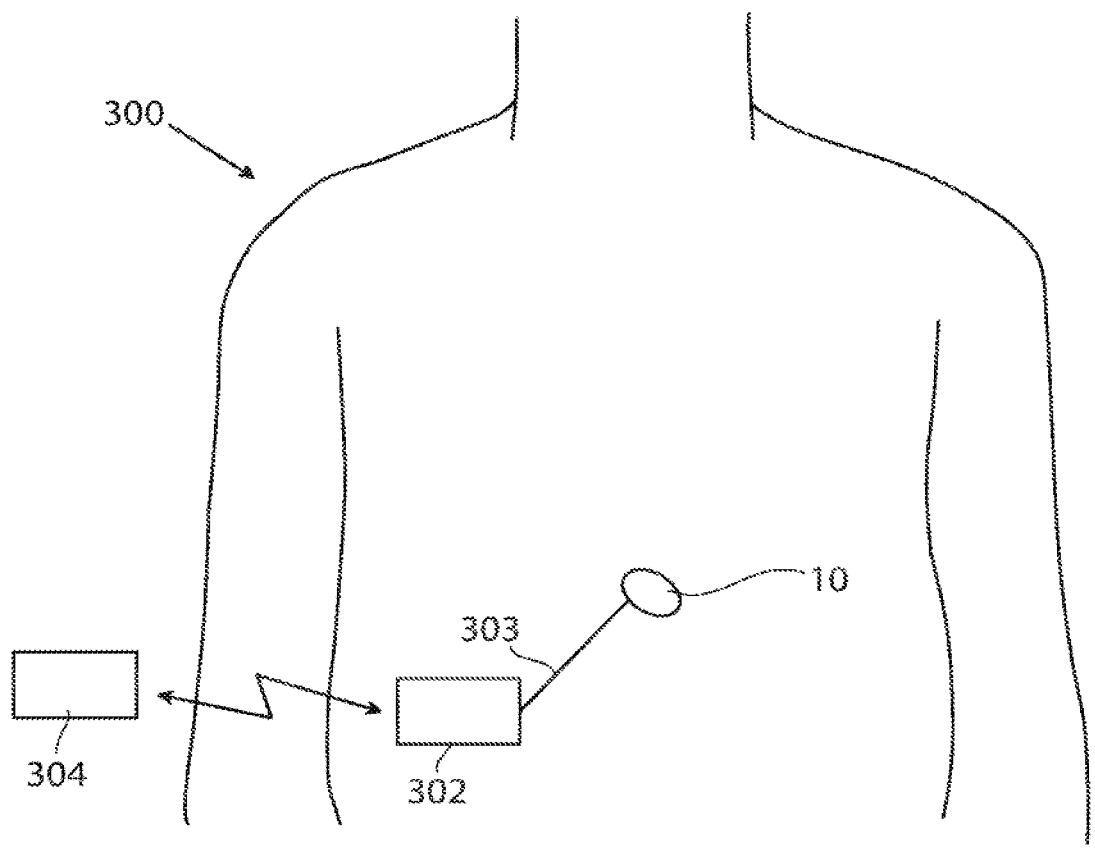
FIG. 15 illustrates a system for treating a disease, wherein the system includes an apparatus of the invention implanted in a patient.

FIG. 15 illustrates a system 300 for treating a disease comprising an apparatus 10 of the present invention placed in the abdomen of a patient. An implanted energy-transforming device 302 is adapted to supply energy consuming components of the apparatus with energy via a power supply line 303. An external energy-transmission device 304 for non-invasively energizing the apparatus 10 transmits energy by at least one wireless energy signal. The implanted energy-transforming device 1002 transforms energy from the wireless energy signal into electric energy which is supplied via the power supply line 303.

The wireless energy signal may include a wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal. Alternatively, the wireless energy signal may include an electric or magnetic field, or a combined electric and magnetic field.

The wireless energy-transmission device 304 may transmit a carrier signal for carrying the wireless energy signal. Such a carrier signal may include digital, analogue or a combination of digital and analogue signals. In this case, the wireless energy signal includes an analogue or a digital signal, or a combination of an analogue and digital signal.

Generally speaking, the energy-transforming device 302 is provided for transforming wireless energy of a first form transmitted by the energy-transmission device 304 into energy of a second form, which typically is different from the energy of the first form. The implanted apparatus 10 is operable in response to the energy of the second form. The energy-transforming device 302 may directly power the apparatus with the second form energy, as the energy-transforming device 302 transforms the first form energy transmitted by the energy-transmission device 304 into the second form energy. The system may further include an implantable accumulator, wherein the second form energy is used at least partly to charge the accumulator.

Alternatively, the wireless energy transmitted by the energy-transmission device 304 may be used to directly power the apparatus, as the wireless energy is being transmitted by the energy-transmission device 304. Where the system comprises an operation device for operating the apparatus, as will be described below, the wireless energy transmitted by the energy-transmission device 304 may be used to directly power the operation device to create kinetic energy for the operation of the apparatus.

The wireless energy of the first form may comprise sound waves and the energy-transforming device 302 may include a piezo-electric element for transforming the sound waves into electric energy. The energy of the second form may comprise electric energy in the form of a direct current or pulsating direct current, or a combination of a direct current and pulsating direct current, or an alternating current or a combination of a direct and alternating current. Normally, the apparatus comprises electric components that are energized with electrical energy. Other implantable electric components of the system may be at least one voltage level guard or at least one constant current guard connected with the electric components of the apparatus. Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transmission device may be controlled from outside the patient's body to release electromagnetic wireless energy, and the released electromagnetic wireless energy is used for operating the apparatus. Alternatively, the energy-transmission device is controlled from outside the patient's body to release non-magnetic wireless energy, and the released non-magnetic wireless energy is used for operating the apparatus.

The external energy-transmission device 304 also includes a wireless remote control having an external signal transmitter for transmitting a wireless control signal for non-invasively controlling the apparatus. The control signal is received by an implanted signal receiver which may be incorporated in the implanted energy-transforming device 302 or be separate from.

The wireless control signal may include a frequency, amplitude, or phase modulated signal or a combination thereof. Alternatively, the wireless control signal includes an analogue or a digital signal, or a combination of an analogue and digital signal. Alternatively, the wireless control signal comprises an electric or magnetic field, or a combined electric and magnetic field.

The wireless remote control may transmit a carrier signal for carrying the wireless control signal. Such a carrier signal may include digital, analogue or a combination of digital and analogue signals. Where the control signal includes an analogue or a digital signal, or a combination of an analogue and digital signal, the wireless remote control preferably transmits an electromagnetic carrier wave signal for carrying the digital or analogue control signals.

FIG. 16 illustrates the system of FIG. 15 in the form of a more generalized block diagram showing the apparatus 10, the energy-transforming device 302 powering the apparatus 100 via power supply line 303, and the external energy-transmission device 304, The patients skin 305, generally shown by a vertical line, separates the interior of the patient to the right of the line from the exterior to the left of the line.

FIG. 17 shows an embodiment of the invention identical to that of FIG. 16, except that a reversing device in the form of an electric switch 306 operable for example by polarized energy also is implanted in the patient for reversing the apparatus 10. When the switch is operated by polarized energy the wireless remote control of the external energy-transmission device 304 transmits a wireless signal that carries polarized energy and the implanted energy-transforming device 302 transforms the wireless polarized energy into a polarized current for operating the electric switch 306. When the polarity of the current is shifted by the implanted energy-transforming device 302 the electric switch 306 reverses the function performed by the apparatus 10.

FIG. 18 shows an embodiment of the invention identical to that of FIG. 16, except that an operation device 307 implanted in the patient for operating the apparatus 100 is provided between the implanted energy-transforming device 302 and the apparatus 10. This operation device can be in the form of a motor 307, such as an electric servomotor. The motor 307 is powered with energy from the implanted energy-transforming device 302, as the remote control of the external energy-transmission device 304 transmits a wireless signal to the receiver of the implanted energy-transforming device 302.

FIG. 19 shows an embodiment of the invention identical to that of FIG. 16, except that it also comprises an operation device is in the form of an assembly 308 including a motor/pump unit 309 and a fluid reservoir 310 is implanted in the patient. In this case the apparatus 10 is hydraulically operated, i.e. hydraulic fluid is pumped by the motor/pump unit 309 from the fluid reservoir 310 through a conduit 311 to the apparatus 10 to operate the apparatus, and hydraulic fluid is pumped by the motor/pump unit 309 back from the apparatus 10 to the fluid reservoir 310 to return the apparatus to a starting position. The implanted energy-transforming device 302 transforms wireless energy into a current, for example a polarized current, for powering the motor/pump unit 309 via an electric power supply line 312.

Instead of a hydraulically operated apparatus 10, it is also envisaged that the operation device comprises a pneumatic operation device. In this case, the hydraulic fluid can be pressurized air to be used for regulation and the fluid reservoir is replaced by an air chamber.

In all of these embodiments the energy-transforming device 302 may include a rechargeable accumulator like a battery or a capacitor to be charged by the wireless energy and supplies energy for any energy consuming part of the system.

As an alternative, the wireless remote control described above may be replaced by manual control of any implanted part to make contact with by the patient's hand most likely indirect, for example a press button placed under the skin.

Figure 20:
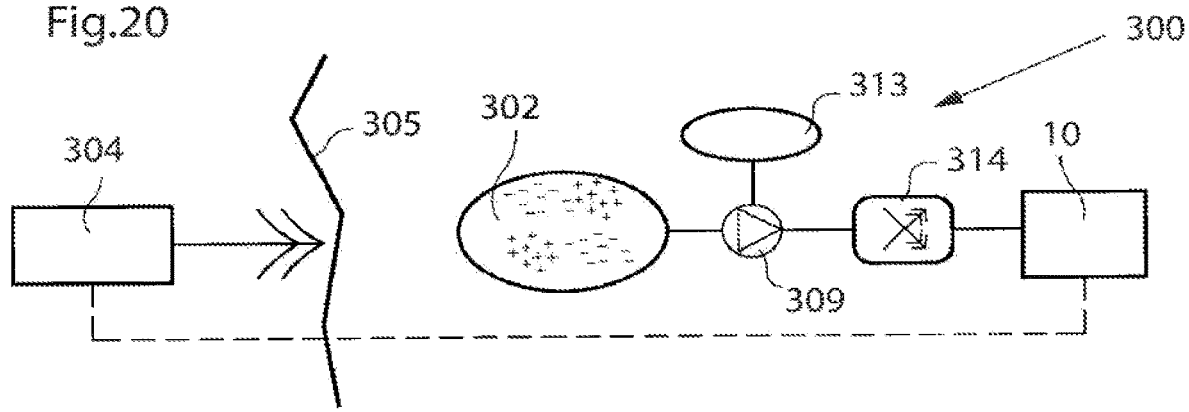

FIG. 20 shows an embodiment of the invention comprising the external energy-transmission device 304 with its wireless remote control, the apparatus 10, in this case hydraulically operated, and the implanted energy-transforming device 302, and further comprising a hydraulic fluid reservoir 313, a motor/pump unit 309 and an reversing device in the form of a hydraulic valve shifting device 314, all implanted in the patient. Of course the hydraulic operation could easily be performed by just changing the pumping direction and the hydraulic valve may therefore be omitted. The remote control may be a device separated from the external energy-transmission device or included in the same.

The motor of the motor/pump unit 309 is an electric motor. In response to a control signal from the wireless remote control of the external energy-transmission device 304, the implanted energy-transforming device 302 powers the motor/pump unit 309 with energy from the energy carried by the control signal, whereby the motor/pump unit 309 distributes hydraulic fluid between the hydraulic fluid reservoir 313 and the apparatus 10. The remote control of the external energy-transmission device 304 controls the hydraulic valve shifting device 314 to shift the hydraulic fluid flow direction between one direction in which the fluid is pumped by the motor/pump unit 309 from the hydraulic fluid reservoir 313 to the apparatus 10 to operate the apparatus, and another opposite direction in which the fluid is pumped by the motor/pump unit 309 back from the apparatus 10 to the hydraulic fluid reservoir 313 to return the apparatus to a starting position.

Figure 21:
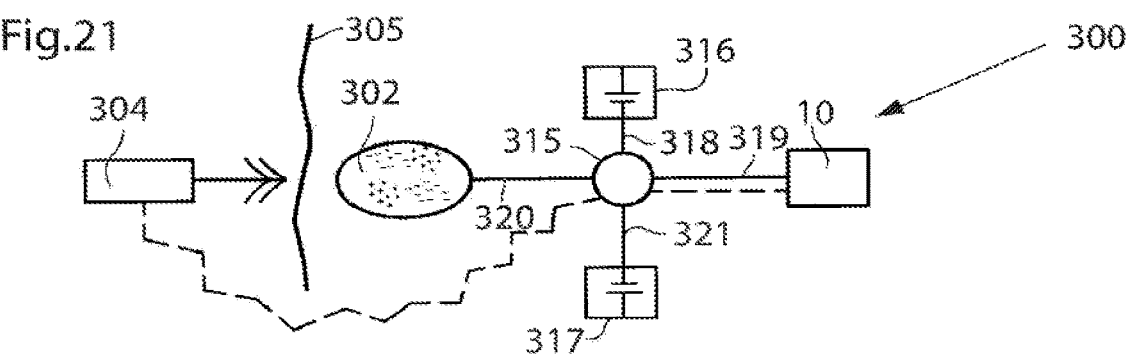

FIG. 21 shows an embodiment of the invention comprising the external energy-transmission device 304 with its wireless remote control, the apparatus 10, the implanted energy-transforming device 302, an implanted internal control unit 315 controlled by the wireless remote control of the external energy-transmission device 304, an implanted accumulator 316 and an implanted capacitor 317. The internal control unit 315 arranges storage of electric energy received from the implanted energy-transforming device 302 in the accumulator 316, which supplies energy to the apparatus 10. In response to a control signal from the wireless remote control of the external energy-transmission device 304, the internal control unit 315 either releases electric energy from the accumulator 316 and transfers the released energy via power lines 318 and 319, or directly transfers electric energy from the implanted energy-transforming device 302 via a power line 320, the capacitor 317, which stabilizes the electric current, a power line 321 and the power line 319, for the operation of the apparatus 10.

The internal control unit is preferably programmable from outside the patient's body. In a preferred embodiment, the internal control unit is programmed to regulate the apparatus 10 according to a pre-programmed time-schedule or to input from any sensor sensing any possible physical parameter of the patient or any functional parameter of the system.

In accordance with an alternative, the capacitor 317 in the embodiment of FIG. 21 may be omitted. In accordance with another alternative, the accumulator 316 in this embodiment may be omitted.

Figure 22:
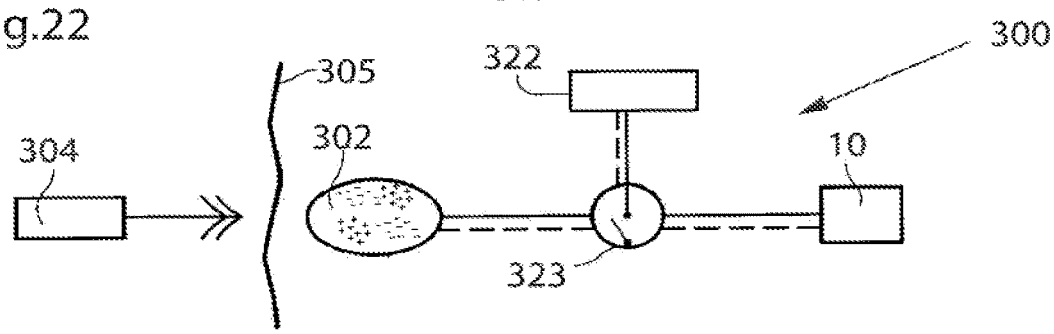

FIG. 22 shows an embodiment of the invention identical to that of FIG. 16, except that a battery 322 for supplying energy for the operation of the apparatus 10 and an electric switch 323 for switching the operation of the apparatus 10 also are implanted in the patient. The electric switch 323 may be controlled by the remote control and may also be operated by the energy supplied by the implanted energy-transforming device 302 to switch from an off mode, in which the battery 322 is not in use, to an on mode, in which the battery 322 supplies energy for the operation of the apparatus 10.

Figure 23:
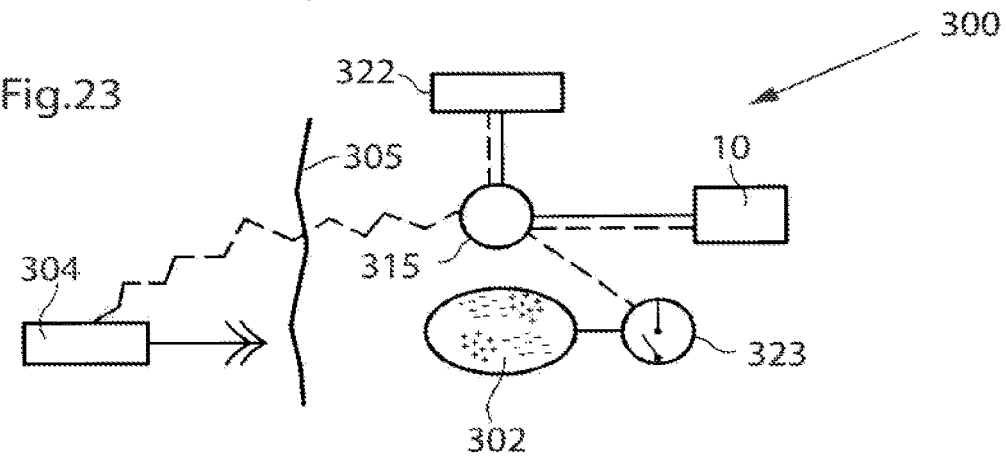

FIG. 23 shows an embodiment of the invention identical to that of FIG. 22, except that an internal control unit 315 controllable by the wireless remote control of the external energy-transmission device 304 also is implanted in the patient. In this case, the electric switch 323 is operated by the energy supplied by the implanted energy-transforming device 302 to switch from an off mode, in which the wireless remote control is prevented from controlling the internal control unit 315 and the battery is not in use, to a standby mode, in which the remote control is permitted to control the internal control unit 315 to release electric energy from the battery 322 for the operation of the apparatus 10.

Figure 24:
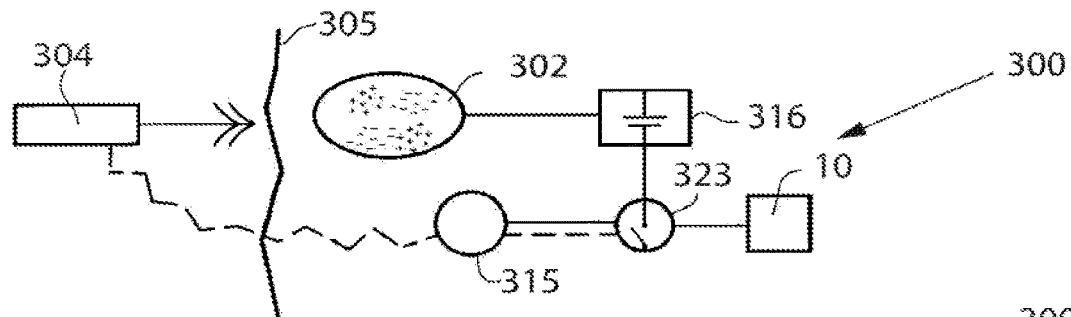

FIG. 24 shows an embodiment of the invention identical to that of FIG. 23, except that an accumulator 316 is substituted for the battery 322 and the implanted components are interconnected differently. In this case, the accumulator 316 stores energy from the implanted energy-transforming device 302. In response to a control signal from the wireless remote control of the external energy-transmission device 304, the internal control unit 315 controls the electric switch 323 to switch from an off mode, in which the accumulator 316 is not in use, to an on mode, in which the accumulator 316 supplies energy for the operation of the apparatus 10. The accumulator may be combined with or replaced by a capacitor.

Figure 25:
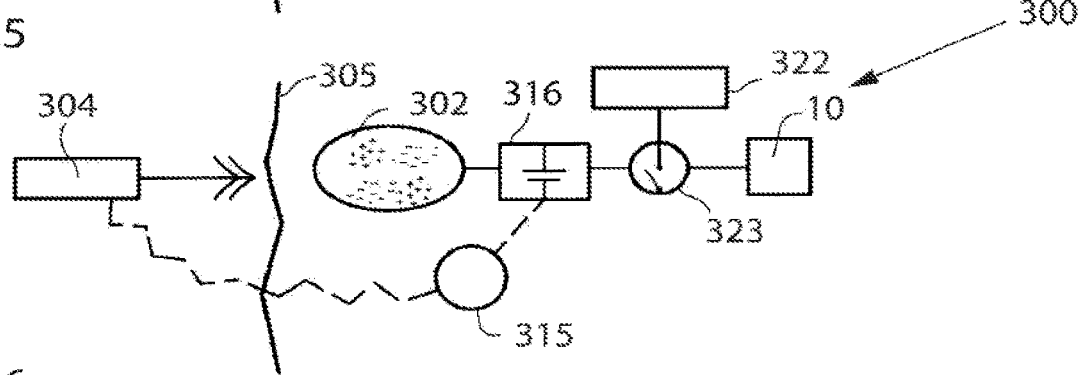

FIG. 25 shows an embodiment of the invention identical to that of FIG. 24, except that a battery 322 also is implanted in the patient and the implanted components are interconnected differently. In response to a control signal from the wireless remote control of the external energy-transmission device 304, the internal control unit 315 controls the accumulator 316 to deliver energy for operating the electric switch 323 to switch from an off mode, in which the battery 322 is not in use, to an on mode, in which the battery 322 supplies electric energy for the operation of the apparatus 10.

Alternatively, the electric switch 323 may be operated by energy supplied by the accumulator 316 to switch from an off mode, in which the wireless remote control is prevented from controlling the battery 322 to supply electric energy and is not in use, to a standby mode, in which the wireless remote control is permitted to control the battery 322 to supply electric energy for the operation of the apparatus 10.

It should be understood that the switch 323 and all other switches in this application should be interpreted in its broadest embodiment. This means a transistor, MCU, MCPU, ASIC, FPGA or a DA converter or any other electronic component or circuit that may switch the power on and off. Preferably the switch is controlled from outside the body, or alternatively by an implanted internal control unit.

Figure 26:
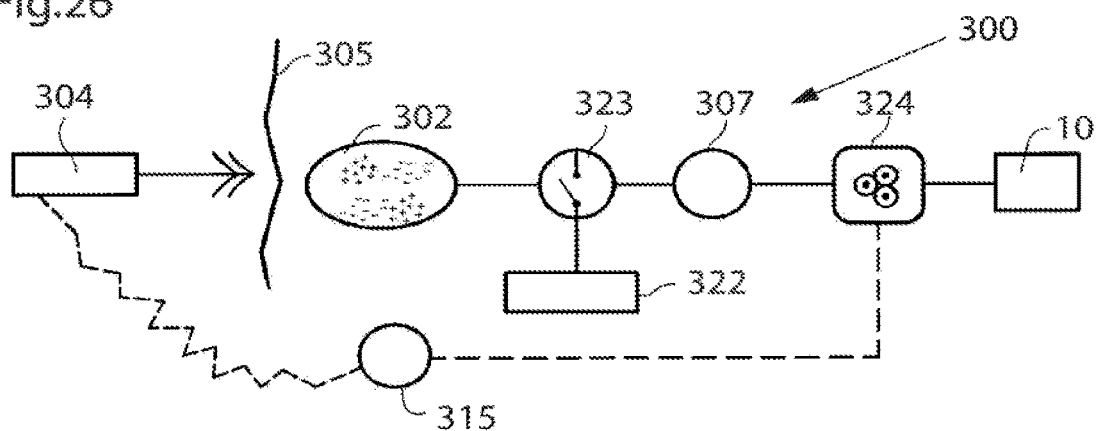

FIG. 26 shows an embodiment of the invention identical to that of FIG. 22, except that a motor 307, a mechanical reversing device in the form of a gear box 324, and an internal control unit 315 for controlling the gear box 324 also are implanted in the patient. The internal control unit 315 controls the gear box 324 to reverse the function performed by the apparatus 10 (mechanically operated). Even simpler is to switch the direction of the motor electronically. The gear box interpreted in its broadest embodiment may stand for a servo arrangement saving force for the operation device in favour of longer stroke to act.

Figure 27:
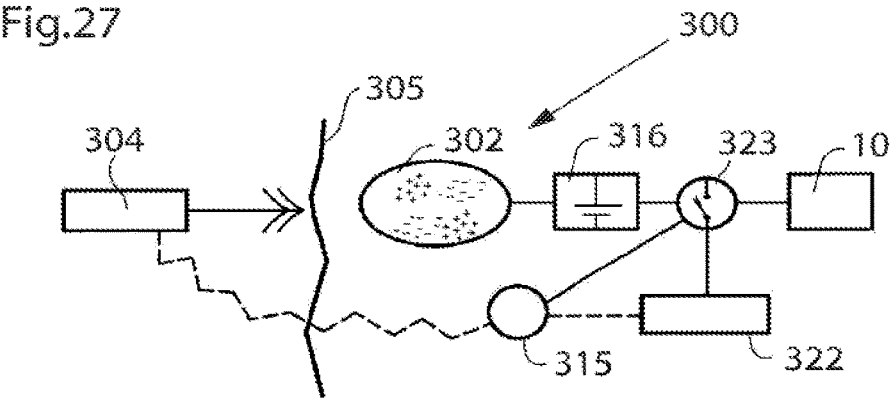

FIG. 27 shows an embodiment of the invention identical to that of FIG. 23 except that the implanted components are interconnected differently. Thus, in this case the internal control unit 315 is powered by the battery 322 when the accumulator 316, suitably a capacitor, activates the electric switch 323 to switch to an on mode. When the electric switch 323 is in its on mode the internal control unit 315 is permitted to control the battery 322 to supply, or not supply, energy for the operation of the apparatus 10.

Figure 28:
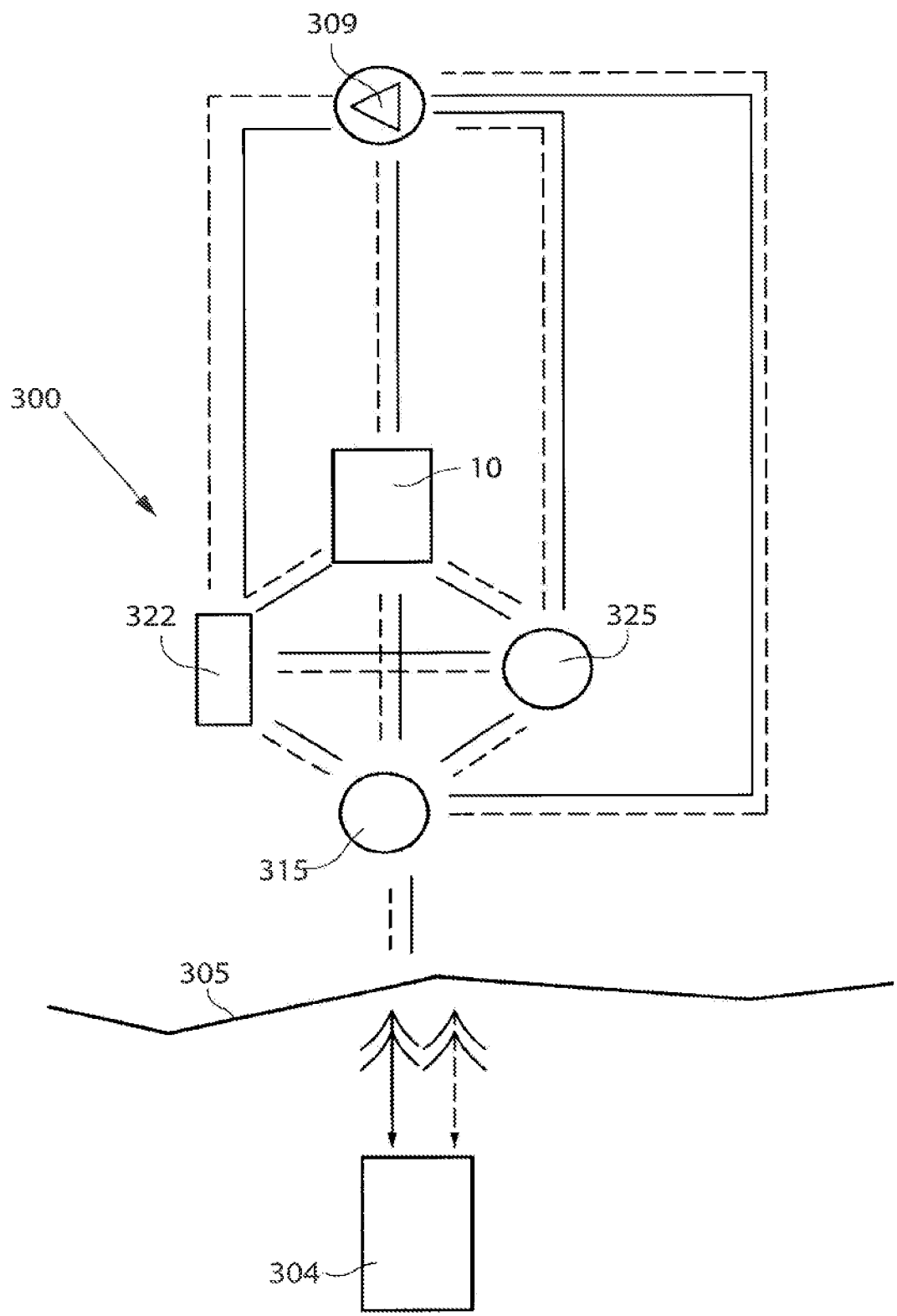

FIG. 28 schematically shows conceivable combinations of implanted components of the apparatus for achieving various communication options. Basically, there are the apparatus 10, the internal control unit 315, motor or pump unit 309, and the external energy-transmission device 304 including the external wireless remote control. As already described above the wireless remote control transmits a control signal which is received by the internal control unit 315, which in turn controls the various implanted components of the apparatus.

A feedback device, preferably comprising a sensor or measuring device 325, may be implanted in the patient for sensing a physical parameter of the patient. The physical parameter may be at least one selected from the group consisting of pressure, volume, diameter, stretching, elongation, extension, movement, bending, elasticity, muscle contraction, nerve impulse, body temperature, blood pressure, blood flow, heartbeats and breathing. The sensor may sense any of the above physical parameters. For example, the sensor may be a pressure or motility sensor. Alternatively, the sensor 325 may be arranged to sense a functional parameter. The functional parameter may be correlated to the transfer of energy for charging an implanted energy source and may further include at least one selected from the group of parameters consisting of; electricity, any electrical parameter, pressure, volume, diameter, stretch, elongation, extension, movement, bending, elasticity, temperature and flow.

The feedback may be sent to the internal control unit or out to an external control unit preferably via the internal control unit. Feedback may be sent out from the body via the energy transfer system or a separate communication system with receiver and transmitters.

The internal control unit 315, or alternatively the external wireless remote control of the external energy-transmission device 304, may control the apparatus 10 in response to signals from the sensor 325. A transceiver may be combined with the sensor 325 for sending information on the sensed physical parameter to the external wireless remote control. The wireless remote control may comprise a signal transmitter or transceiver and the internal control unit 315 may comprise a signal receiver or transceiver. Alternatively, the wireless remote control may comprise a signal receiver or transceiver and the internal control unit 315 may comprise a signal transmitter or transceiver. The above transceivers, transmitters and receivers may be used for sending information or data related to the apparatus 10 from inside the patient's body to the outside thereof.

Where the motor/pump unit 309 and battery 322 for powering the motor/pump unit 309 are implanted, information related to the charging of the battery 322 may be fed back. To be more precise, when charging a battery or accumulator with energy feed back information related to said charging process is sent and the energy supply is changed accordingly.

FIG. 29 shows an alternative embodiment wherein the apparatus 10 is regulated from outside the patient's body. The system 300 comprises a battery 322 connected to the apparatus 10 via a subcutaneous electric switch 326. Thus, the regulation of the apparatus 10 is performed non-invasively by manually pressing the subcutaneous switch, whereby the operation of the apparatus 10 is switched on and off. It will be appreciated that the shown embodiment is a simplification and that additional components, such as an internal control unit or any other part disclosed in the present application can be added to the system. Two subcutaneous switches may also be used. In the preferred embodiment one implanted switch sends information to the internal control unit to perform a certain predetermined performance and when the patient press the switch again the performance is reversed.

FIG. 30 shows an alternative embodiment, wherein the system 300 comprises a hydraulic fluid reservoir 313 hydraulically connected to the apparatus. Non-invasive regulation is performed by manually pressing the hydraulic reservoir connected to the apparatus.

The system may include an external data communicator and an implantable internal data communicator communicating with the external data communicator. The internal communicator feeds data related to the apparatus or the patient to the external data communicator and/or the external data communicator feeds data to the internal data communicator.

FIG. 31 schematically illustrates an arrangement of the system that is capable of sending information from inside the patient's body to the outside thereof to give feedback information related to at least one functional parameter of the apparatus or system, or related to a physical parameter of the patient, in order to supply an accurate amount of energy to an implanted internal energy receiver 302 connected to implanted energy consuming components of the apparatus 10. Such an energy receiver 302 may include an energy source and/or an energy-transforming device. Briefly described, wireless energy is transmitted from an external energy source 304a located outside the patient and is received by the internal energy receiver 302 located inside the patient.

The internal energy receiver is adapted to directly or indirectly supply received energy to the energy consuming components of the apparatus 10 via a switch 326. An energy balance is determined between the energy received by the internal energy receiver 302 and the energy used for the apparatus 10, and the transmission of wireless energy is then controlled based on the determined energy balance. The energy balance thus provides an accurate indication of the correct amount of energy needed, which is sufficient to operate the apparatus 10 properly, but without causing undue temperature rise.

In FIG. 31 the patient's skin is indicated by a vertical line 305. Here, the energy receiver comprises an energy-transforming device 302 located inside the patient, preferably just beneath the patient's skin 305. Generally speaking, the implanted energy-transforming device 302 may be placed in the abdomen, thorax, muscle fascia (e.g. in the abdominal wall), subcutaneously, or at any other suitable location. The implanted energy-transforming device 302 is adapted to receive wireless energy E transmitted from the external energy-source 304a provided in an external energy-transmission device 304 located outside the patient's skin 305 in the vicinity of the implanted energy-transforming device 302.

As is well known in the art, the wireless energy E may generally be transferred by means of any suitable Transcutaneous Energy Transfer (TET) device, such as a device including a primary coil arranged in the external energy source 304a and an adjacent secondary coil arranged in the implanted energy-transforming device 302. When an electric current is fed through the primary coil, energy in the form of a voltage is induced in the secondary coil which can be used to power the implanted energy consuming components of the apparatus, e.g. after storing the incoming energy in an implanted energy source, such as a rechargeable battery or a capacitor. However, the present invention is generally not limited to any particular energy transfer technique, TET devices or energy sources, and any kind of wireless energy may be used. The amount of energy received by the implanted energy receiver may be compared with the energy used by the implanted components of the apparatus. The term "energy used" is then understood to include also energy stored by implanted components of the apparatus. A control device includes an external control unit 304b that controls the external energy source 304a based on the determined energy balance to regulate the amount of transferred energy. In order to transfer the correct amount of energy, the energy balance and the required amount of energy is determined by means of a determination device including an implanted internal control unit 315 connected between the switch 326 and the apparatus 10. The internal control unit 315 may thus be arranged to receive various measurements obtained by suitable sensors or the like, not shown, measuring certain characteristics of the apparatus 10, somehow reflecting the required amount of energy needed for proper operation of the apparatus 10. Moreover, the current condition of the patient may also be detected by means of suitable measuring devices or sensors, in order to provide parameters reflecting the patient's condition. Hence, such characteristics and/or parameters may be related to the current state of the apparatus 10, such as power consumption, operational mode and temperature, as well as the patient's condition reflected by parameters such as; body temperature, blood pressure, heartbeats and breathing. Other kinds of physical parameters of the patient and functional parameters of the device are described elsewhere.

Furthermore, an energy source in the form of an accumulator 316 may optionally be connected to the implanted energy-transforming device 302 via the control unit 315 for accumulating received energy for later use by the apparatus 10. Alternatively or additionally, characteristics of such an accumulator, also reflecting the required amount of energy, may be measured as well. The accumulator may be replaced by a rechargeable battery, and the measured characteristics may be related to the current state of the battery, any electrical parameter such as energy consumption voltage, temperature, etc. In order to provide sufficient voltage and current to the apparatus 10, and also to avoid excessive heating, it is clearly understood that the battery should be charged optimally by receiving a correct amount of energy from the implanted energy-transforming device 302, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit 315. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 315 of the determination device is adapted to determine the energy balance and/or the currently required amount of energy, (either energy per time unit or accumulated energy) based on measurements made by the above-mentioned sensors or measuring devices of the apparatus 10, or the patient, or an implanted energy source if used, or any combination thereof. The internal control unit 315 is further connected to an internal signal transmitter 327, arranged to transmit a control signal reflecting the determined required amount of energy, to an external signal receiver 304c connected to the external control unit 304b. The amount of energy transmitted from the external energy source 304a may then be regulated in response to the received control signal.

Alternatively, the determination device may include the external control unit 304b. In this alternative, sensor measurements can be transmitted directly to the external control unit 304b wherein the energy balance and/or the currently required amount of energy can be determined by the external control unit 304*b*, thus integrating the above-described function of the internal control unit 315 in the external control unit 304*b*. In that case, the internal control unit 315 can be omitted and the sensor measurements are supplied directly to the internal signal transmitter 327 which sends the measurements over to the external signal receiver 304*c* and the external control unit 304*b*. The energy balance and the currently required amount of energy can then be determined by the external control unit 304*b* based on those sensor measurements.

Hence, the present solution according to the arrangement of FIG. 31 employs the feedback of information indicating the required energy, which is more efficient than previous solutions because it is based on the actual use of energy that is compared to the received energy, e.g. with respect to the amount of energy, the energy difference, or the energy receiving rate as compared to the energy rate used by implanted energy consuming components of the apparatus. The apparatus may use the received energy either for consuming or for storing the energy in an implanted energy source or the like. The different parameters discussed above would thus be used if relevant and needed and then as a tool for determining the actual energy balance. However, such parameters may also be needed per se for any actions taken internally to specifically operate the apparatus.

The internal signal transmitter 327 and the external signal receiver 304*c* may be implemented as separate units using suitable signal transfer means, such as radio, IR (Infrared) or ultrasonic signals. Alternatively, the internal signal transmitter 327 and the external signal receiver 304*c* may be integrated in the implanted energy-transforming device 302 and the external energy source 304*a*, respectively, so as to convey control signals in a reverse direction relative to the energy transfer, basically using the same transmission technique. The control signals may be modulated with respect to frequency, phase or amplitude.

Thus, the feedback information may be transferred either by a separate communication system including receivers and transmitters or may be integrated in the energy system. In accordance with the present invention, such an integrated information feedback and energy system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil.

The external second coil of the energy transmitter transmits wireless energy which is received by the first coil of the energy receiver. This system further comprises a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off. In implementing this system in the arrangement of FIG. 31, the switch 326 is either separate and controlled by the internal control unit 315, or integrated in the internal control unit 315. It should be understood that the switch 326 should be interpreted in its broadest embodiment. This means a transistor, MCU, MCPU, ASIC FPGA or a DA converter or any other electronic component or circuit that may switch the power on and off.

To conclude, the energy supply arrangement illustrated in FIG. 31 may operate basically in the following manner. The energy balance is first determined by the internal control unit 315 of the determination device. A control signal reflecting the required amount of energy is also created by the internal control unit 315, and the control signal is transmitted from the internal signal transmitter 327 to the external signal receiver 304*c*. Alternatively, the energy balance can be determined by the external control unit 304*b* instead depending on the implementation, as mentioned above. In that case, the control signal may carry measurement results from various sensors. The amount of energy emitted from the external energy source 304*a* can then be regulated by the external control unit 304*b*, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 304*a*, such as voltage, current, amplitude, wave frequency and pulse characteristics.

This system may also be used to obtain information about the coupling factors between the coils in a TET system even to calibrate the system both to find an optimal place for the external coil in relation to the internal coil and to optimize energy transfer. Simply comparing in this case the amount of energy transferred with the amount of energy received. For example if the external coil is moved the coupling factor may vary and correctly displayed movements could cause the external coil to find the optimal place for energy transfer. Preferably, the external coil is adapted to calibrate the amount of transferred energy to achieve the feedback information in the determination device, before the coupling factor is maximized.

This coupling factor information may also be used as a feedback during energy transfer. In such a case, the energy system of the present invention comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factor between the first and second coils. The energy transmitter may regulate the transmitted energy in response to the obtained coupling factor.

Figure 32:
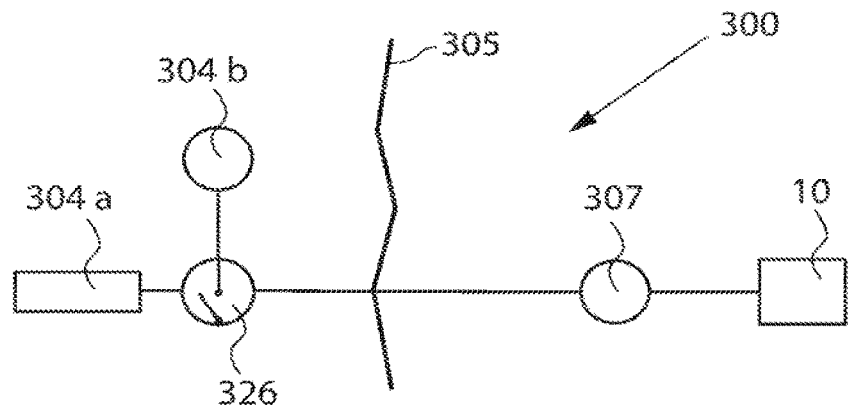
FIG. 32 schematically shows an embodiment of the system, in which the apparatus is operated with wire bound energy.

With reference to FIG. 32, although wireless transfer of energy for operating the apparatus has been described above to enable non-invasive operation, it will be appreciated that the apparatus can be operated with wire bound energy as well. Such an example is shown in FIG. 32, wherein an external switch 326 is interconnected between the external energy source 304*a* and an operation device, such as an electric motor 307 operating the apparatus 10. An external control unit 304*b* controls the operation of the external switch 326 to effect proper operation of the apparatus 10.

Figure 33:
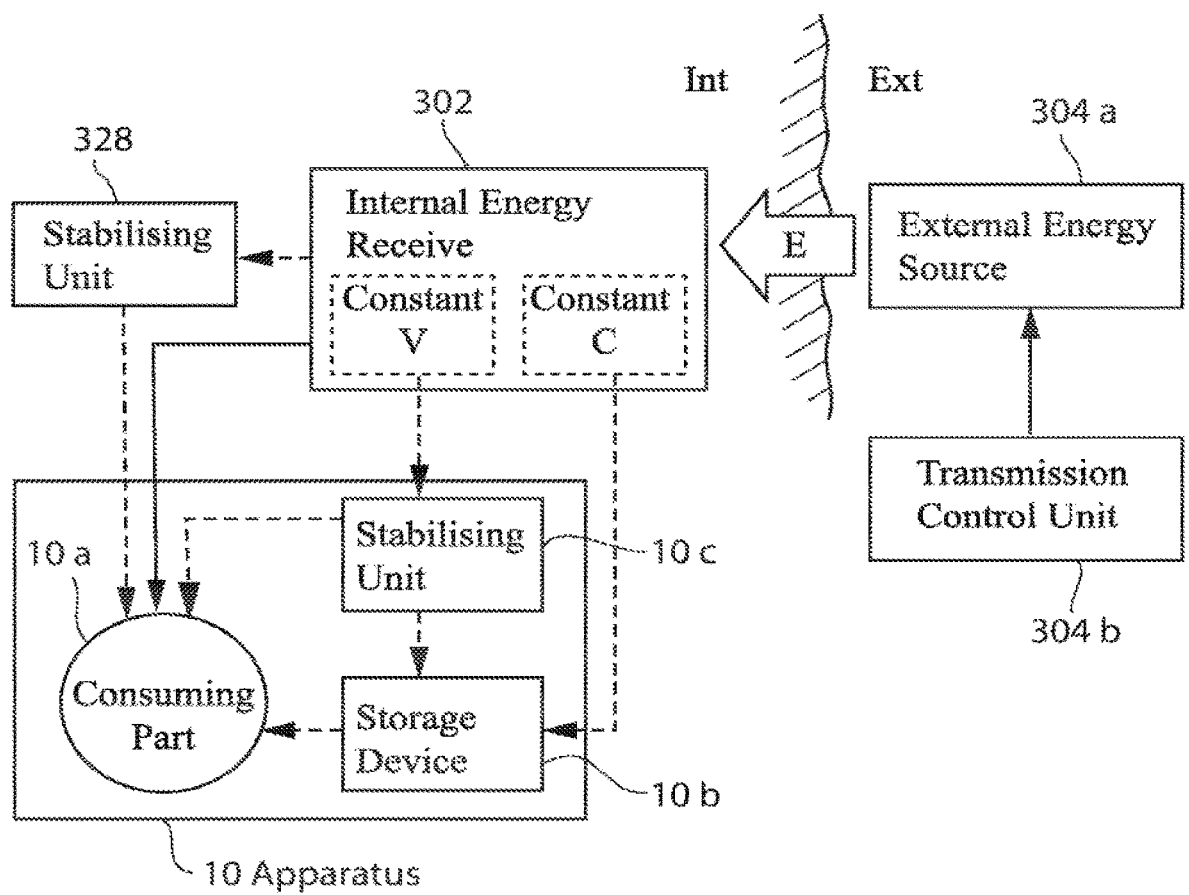
FIG. 33 is a more detailed block diagram of an arrangement for controlling the transmission of wireless energy used for the operation of the apparatus shown in FIG. 15.

FIG. 33 illustrates different embodiments for how received energy can be supplied to and used by the apparatus 10. Similar to the example of FIG. 31, an internal energy receiver 302 receives wireless energy E from an external energy source 304a which is controlled by a transmission control unit 304b.

The internal energy receiver 302 may comprise a constant voltage circuit, indicated as a dashed box "constant V" in the figure, for supplying energy at constant voltage to the apparatus 10. The internal energy receiver 302 may further comprise a constant current circuit, indicated as a dashed box "constant C" in the figure, for supplying energy at constant current to the apparatus 10.

The apparatus 10 comprises an energy consuming part 10a, which may be a motor, pump, restriction device, or any other medical appliance that requires energy for its electrical operation. The apparatus 10 may further comprise an energy storage device 10b for storing energy supplied from the internal energy receiver 302. Thus, the supplied energy may be directly consumed by the energy consuming part 10a, or stored by the energy storage device 10b, or the supplied energy may be partly consumed and partly stored. The apparatus 10 may further comprise an energy stabilizing unit 10c for stabilizing the energy supplied from the internal energy receiver 302. Thus, the energy may be supplied in a fluctuating manner such that it may be necessary to stabilize the energy before consumed or stored.

The energy supplied from the internal energy receiver 302 may further be accumulated and/or stabilized by a separate energy stabilizing unit 328 located outside the apparatus 10, before being consumed and/or stored by the apparatus 10. Alternatively, the energy stabilizing unit 328 may be integrated in the internal energy receiver 302. In either case, the energy stabilizing unit 328 may comprise a constant voltage circuit and/or a constant current circuit.

It should be noted that FIG. 31 and FIG. 33 illustrate some possible but non-limiting implementation options regarding how the various shown functional components and elements can be arranged and connected to each other. However, the skilled person will readily appreciate that many variations and modifications can be made within the scope of the present invention.

Figure 34:
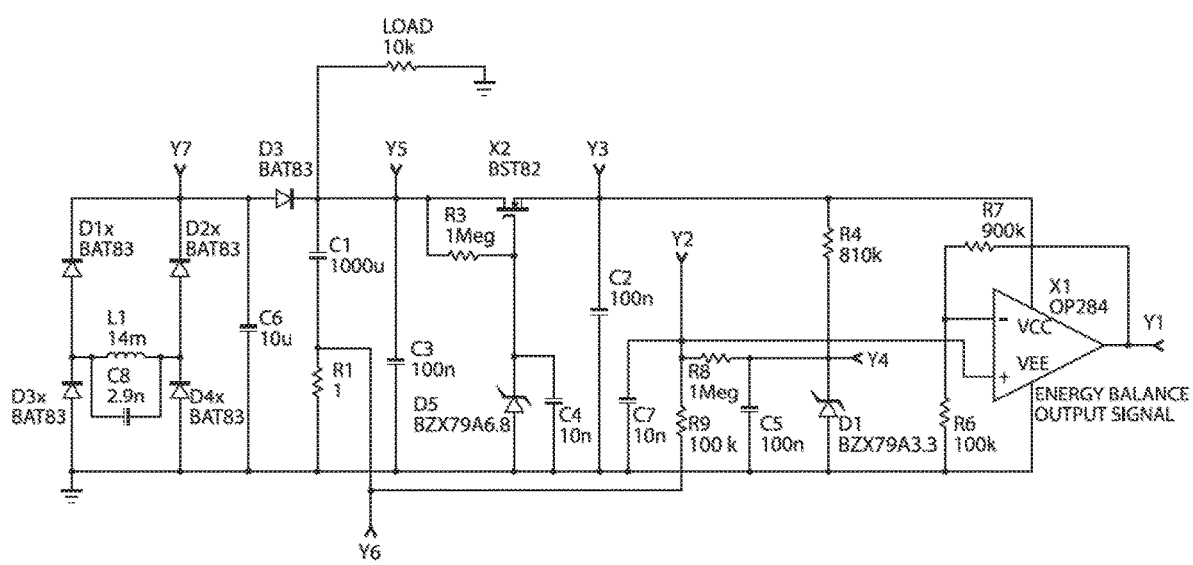
FIG. 34 is a circuit for the arrangement shown in FIG. 33, according to a possible implementation example.

FIG. 34 schematically shows an energy balance measuring circuit of one of the proposed designs of the system for controlling transmission of wireless energy, or energy balance control system. The circuit has an output signal centered on 2.5V and proportionally related to the energy imbalance. The derivative of this signal shows if the value goes up and down and how fast such a change takes place. If the amount of received energy is lower than the energy used by implanted components of the apparatus, more energy is transferred and thus charged into the energy source. The output signal from the circuit is typically feed to an A/D converter and converted into a digital format. The digital information can then be sent to the external energy-transmission device allowing it to adjust the level of the transmitted energy. Another possibility is to have a completely analog system that uses comparators comparing the energy balance level with certain maximum and minimum thresholds sending information to external energy-transmission device if the balance drifts out of the max/min window.

The schematic FIG. 34 shows a circuit implementation for a system that transfers energy to the implanted energy components of the apparatus of the present invention from outside of the patient's body using inductive energy transfer. An inductive energy transfer system typically uses an external transmitting coil and an internal receiving coil. The receiving coil, L1, is included in the schematic FIG. 17; the transmitting parts of the system are excluded.

The implementation of the general concept of energy balance and the way the information is transmitted to the external energy transmitter can of course be implemented in numerous different ways. The schematic FIG. 20 and the above described method of evaluating and transmitting the information should only be regarded as examples of how to implement the control system.

Circuit Details

In FIG. 34 the symbols Y1, Y2, Y3 and so on symbolize test points within the circuit. The components in the diagram and their respective values are values that work in this particular implementation which of course is only one of an infinite number of possible design solutions.

Energy to power the circuit is received by the energy receiving coil L1. Energy to implanted components is transmitted in this particular case at a frequency of 25 kHz. The energy balance output signal is present at test point Y1.

Those skilled in the art will realize that the above various embodiments of the system could be combined in many different ways. For example, the electric switch 306 of FIG. 34 could be incorporated in any of the embodiments of FIGS. 20-36, the hydraulic valve shifting device 314 of FIG. 34 could be incorporated in the embodiment of FIG. 33, and the gear box 324 could be incorporated in the embodiment of FIG. 32. Please observe that the switch simply could mean any electronic circuit or component.

The embodiments described in connection with FIGS. 31, 33 and 34 identify a method and a system for controlling transmission of wireless energy to implanted energy consuming components of an electrically operable apparatus. Such a method and system will be defined in general terms in the following.

A method is thus provided for controlling transmission of wireless energy supplied to implanted energy consuming components of an apparatus as described above. The wireless energy E is transmitted from an external energy source located outside the patient and is received by an internal energy receiver located inside the patient, the internal energy receiver being connected to the implanted energy consuming components of the apparatus for directly or indirectly supplying received energy thereto. An energy balance is determined between the energy received by the internal energy receiver and the energy used for the apparatus. The transmission of wireless energy E from the external energy source is then controlled based on the determined energy balance.

The wireless energy may be transmitted inductively from a primary coil in the external energy source to a secondary coil in the internal energy receiver. A change in the energy balance may be detected to control the transmission of wireless energy based on the detected energy balance change. A difference may also be detected between energy received by the internal energy receiver and energy used for the medical device, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the medical device may be consumed to operate the medical device, and/or stored in at least one energy storage device of the medical device.

When electrical and/or physical parameters of the medical device and/or physical parameters of the patient are determined, the energy may be transmitted for consumption and storage according to a transmission rate per time unit which is determined based on said parameters. The total amount of transmitted energy may also be determined based on said parameters.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or current related to the energy balance.

The transmission of wireless energy from the external energy source may be controlled by applying to the external energy source electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

The circuit formed by the first electric circuit and the external energy source may have a first characteristic time period or first time constant, and when effectively varying the transmitted energy, such frequency time period may be in the range of the first characteristic time period or time constant or shorter.

A system comprising an apparatus as described above is thus also provided for controlling transmission of wireless energy supplied to implanted energy consuming components of the apparatus. In its broadest sense, the system comprises a control device for controlling the transmission of wireless energy from an energy-transmission device, and an implantable internal energy receiver for receiving the transmitted wireless energy, the internal energy receiver being connected to implantable energy consuming components of the apparatus for directly or indirectly supplying received energy thereto. The system further comprises a determination device adapted to determine an energy balance between the energy received by the internal energy receiver and the energy used for the implantable energy consuming components of the apparatus, wherein the control device controls the transmission of wireless energy from the external energy-transmission device, based on the energy balance determined by the determination device.

Further, the system may comprise any of the following:
- A primary coil in the external energy source adapted to transmit the wireless energy inductively to a secondary coil in the internal energy receiver.
- The determination device is adapted to detect a change in the energy balance, and the control device controls the transmission of wireless energy based on the detected energy balance change
- The determination device is adapted to detect a difference between energy received by the internal energy receiver and energy used for the implantable energy consuming components of the apparatus, and the control device controls the transmission of wireless energy based on the detected energy difference.
- The control device controls the external energy-transmission device to decrease the amount of transmitted wireless energy if the detected energy balance change implies that the energy balance is increasing, or vice versa, wherein the decrease/increase of energy transmission corresponds to a detected change rate.
- The control device controls the external energy-transmission device to decrease the amount of transmitted wireless energy if the detected energy difference implies that the received energy is greater than the used energy, or vice versa, wherein the decrease/increase of energy transmission corresponds to the magnitude of said detected energy difference.
- The energy used for the apparatus is consumed to operate the apparatus, and/or stored in at least one energy storage device of the apparatus.
- Where electrical and/or physical parameters of the apparatus and/or physical parameters of the patient are determined, the energy-transmission device transmits the energy for consumption and storage according to a transmission rate per time unit which is determined by the determination device based on said parameters. The determination device also determines the total amount of transmitted energy based on said parameters.
- When a difference is detected between the total amount of energy received by the internal energy receiver and the total amount of consumed and/or stored energy, and the detected difference is related to the integral over time of at least one measured electrical parameter related to the energy balance, the determination device determines the integral for a monitored voltage and/or current related to the energy balance.

When the derivative is determined over time of a measured electrical parameter related to the amount of consumed and/or stored energy, the determination device determines the derivative for a monitored voltage and/or current related to the energy balance.

The energy-transmission device comprises a coil placed externally to the human body, and an electric circuit is provided to power the external coil with electrical pulses to transmit the wireless energy. The electrical pulses have leading and trailing edges, and the electric circuit is adapted to vary first time intervals between successive leading and trailing edges and/or second time intervals between successive trailing and leading edges of the electrical pulses to vary the power of the transmitted wireless energy. As a result, the energy receiver receiving the transmitted wireless energy has a varied power.

The electric circuit is adapted to deliver the electrical pulses to remain unchanged except varying the first and/or second time intervals.

The electric circuit has a time constant and is adapted to vary the first and second time intervals only in the range of the first time constant, so that when the lengths of the first and/or second time intervals are varied, the transmitted power over the coil is varied.

The electric circuit is adapted to deliver the electrical pulses to be varied by only varying the lengths of first time intervals between successive leading and trailing edges of the electrical pulses.

The electric circuit is adapted to supplying a train of two or more electrical pulses in a row, said train having a first electrical pulse at the start of the pulse train and having a second electrical pulse at the end of the pulse train, and the lengths of the second time intervals between successive trailing edge of the second electrical pulse in a first pulse train and leading edge of the first electrical pulse of a second pulse train are varied by the first electronic circuit.

The electric circuit is adapted to provide the electrical pulses as pulses having a substantially constant height and/or amplitude and/or intensity and/or voltage and/or current and/or frequency.

The electric circuit has a time constant, and is adapted to vary the first and second time intervals only in the range of the first time constant, so that when the lengths of the first and/or second time intervals are varied, the transmitted power over the first coil are varied.

The electric circuit is adapted to provide the electrical pulses varying the lengths of the first and/or the second time intervals only within a range that includes the first time constant or that is located relatively close to the first time constant, compared to the magnitude of the first time constant.

FIGS. 35-38 show in more detail block diagrams of four different ways of hydraulically or pneumatically powering an implanted apparatus according to the invention.

Figure 35:
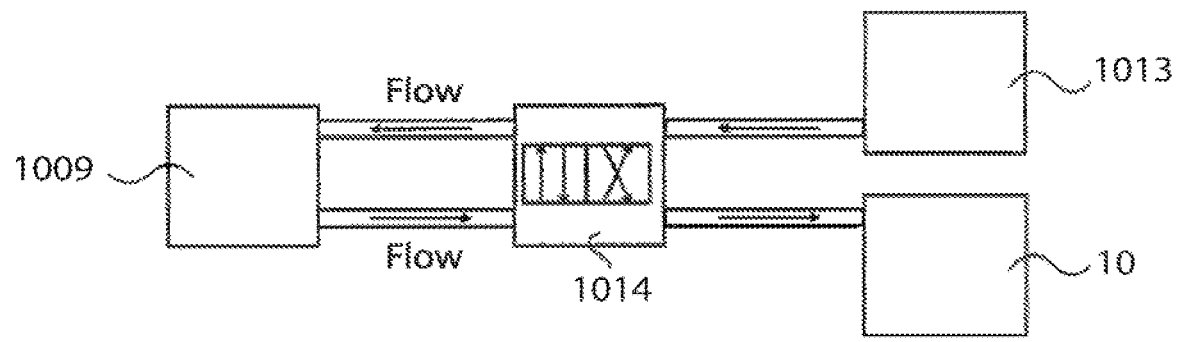
FIGS. 35-42 show various ways of arranging hydraulic or pneumatic powering of an apparatus implanted in a patient.

FIG. 35 shows a system as described above with. The system comprises an implanted apparatus 10 and further a separate regulation reservoir 1013, a one way pump 1009 and an alternate valve 1014.

Figure 36:
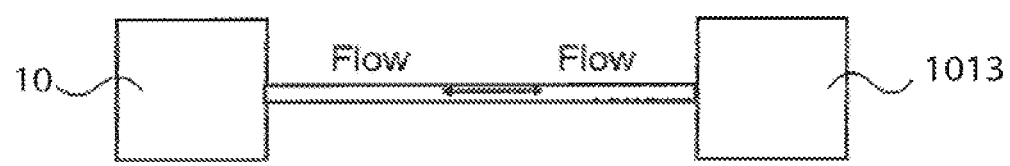

FIG. 36 shows the apparatus 10 and a fluid reservoir 1013. By moving the wall of the regulation reservoir or changing the size of the same in any other different way, the adjustment of the apparatus may be performed without any valve, just free passage of fluid any time by moving the reservoir wall.

Figure 37:
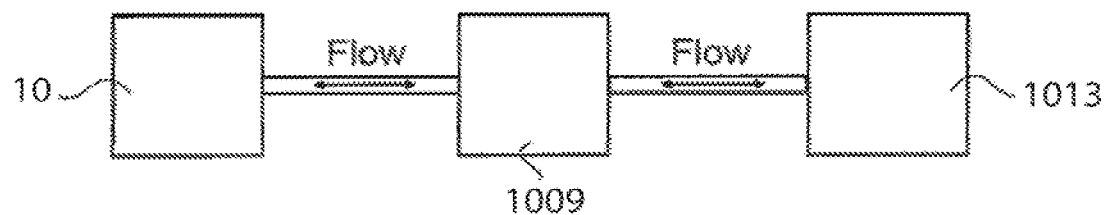

FIG. 37 shows the apparatus 10, a two way pump 1009 and the regulation reservoir 1013.

Figure 38:
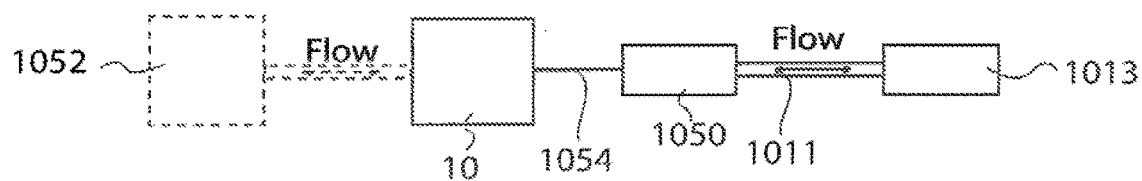

FIG. 38 shows a block diagram of a reversed servo system with a first closed system controlling a second closed system. The servo system comprises a regulation reservoir 1013 and a servo reservoir 1050. The servo reservoir 1050 mechanically controls an implanted apparatus 10 via a mechanical interconnection 1054. The apparatus has an expandable/contactable cavity. This cavity is preferably expanded or contracted by supplying hydraulic fluid from the larger adjustable reservoir 1052 in fluid connection with the apparatus 10. Alternatively, the cavity contains compressible gas, which can be compressed and expanded under the control of the servo reservoir 1050. The servo reservoir 1050 can also be part of the apparatus itself.

Figure 39A:
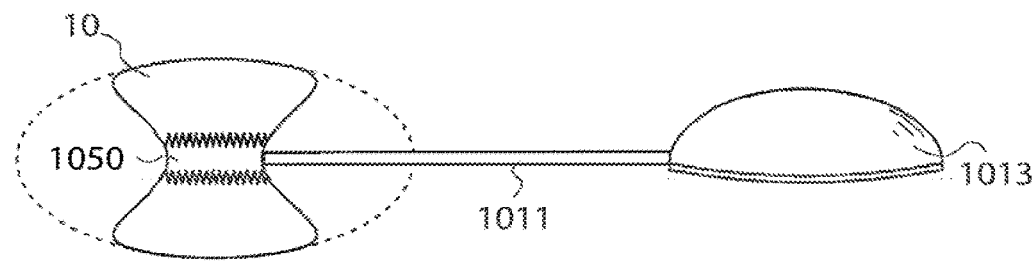
Figure 39B:
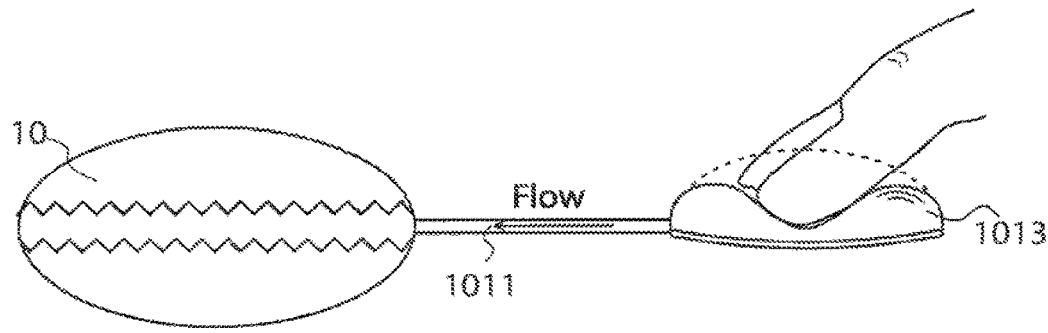
Figure 39C:
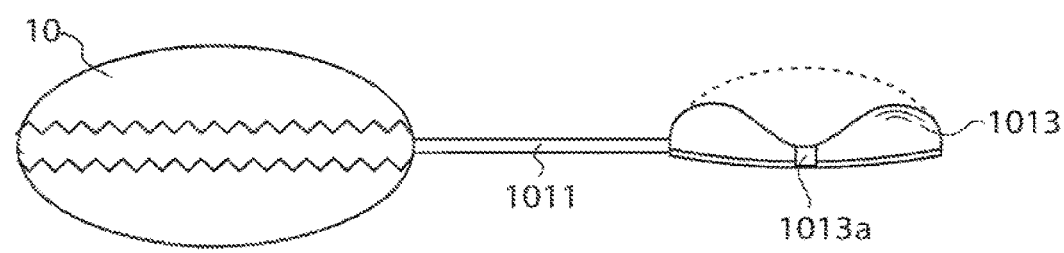
Figure 40:
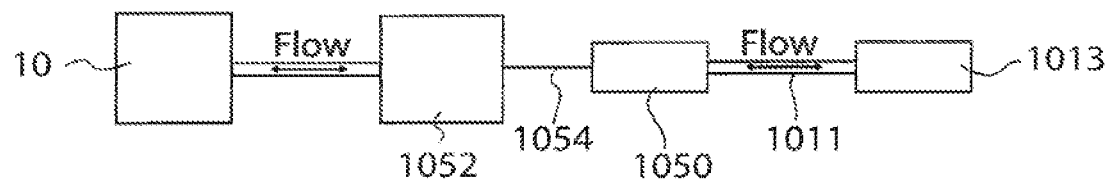

In one embodiment, the regulation reservoir is placed subcutaneous under the patient's skin and is operated by pushing the outer surface thereof by means of a finger. This system is illustrated in FIGS. 39*a-c*. In FIG. 39*a*, a flexible subcutaneous regulation reservoir 1013 is shown connected to a bulge shaped servo reservoir 1050 by means of a conduit 1011. This bellow shaped servo reservoir 1050 is comprised in a flexible apparatus 10. In the state shown in FIG. 39*a*, the servo reservoir 1050 contains a minimum of fluid and most fluid is found in the regulation reservoir 1013. Due to the mechanical interconnection between the servo reservoir 1050 and the apparatus 10, the outer shape of the apparatus 10 is contracted, i.e., it occupies less than its maximum volume. This maximum volume is shown with dashed lines in the figure.

FIG. 39*b* shows a state wherein a user, such as the patient in with the apparatus is implanted, presses the regulation reservoir 1013 so that fluid contained therein is brought to flow through the conduit 1011 and into the servo reservoir 1050, which, thanks to its bellow shape, expands longitudinally. This expansion in turn expands the apparatus 10 so that it occupies its maximum volume, thereby stretching the stomach wall (not shown), which it contacts.

The regulation reservoir 1013 is preferably provided with means 1013*a* for keeping its shape after compression. This means, which is schematically shown in the figure, will thus keep the apparatus 10 in a stretched position also when the user releases the regulation reservoir. In this way, the regulation reservoir essentially operates as an on/off switch for the system.

An alternative embodiment of hydraulic or pneumatic operation will now be described with reference to FIGS. 40 and 41*a-c*. The block diagram shown in FIG. 40 comprises with a first closed system controlling a second closed system. The first system comprises a regulation reservoir 1013 and a servo reservoir 1050. The servo reservoir 1050 mechanically controls a larger adjustable reservoir 1052 via a mechanical interconnection 1054. An implanted apparatus 10 having an expandable/contactable cavity is in turn controlled by the larger adjustable reservoir 1052 by supply of hydraulic fluid from the larger adjustable reservoir 1052 in fluid connection with the apparatus 10.

Figure 41A:
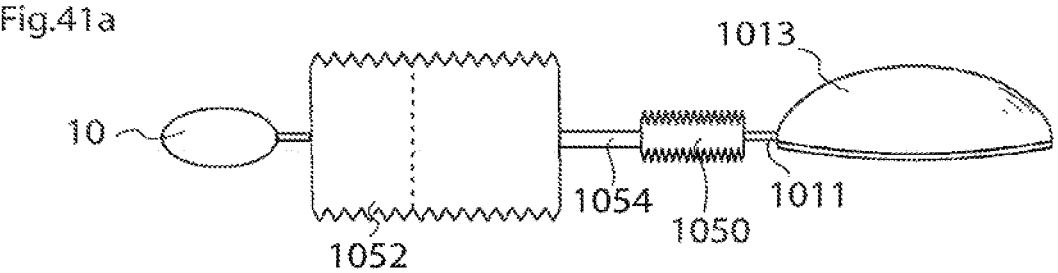
Figure 41B:
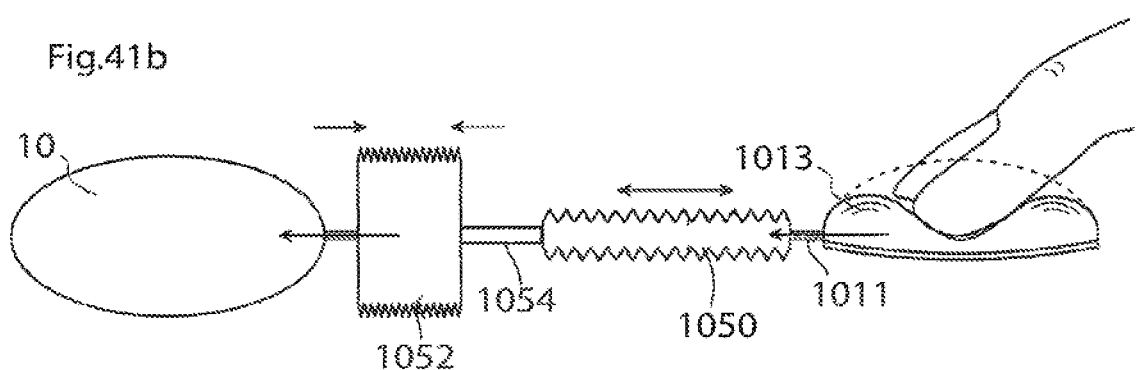
Figure 41C:
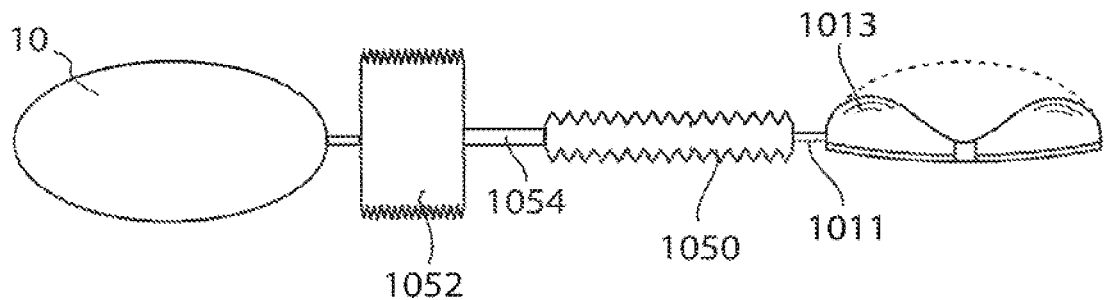

An example of this embodiment will now be described with reference to FIG. 41*a-c*. Like in the previous embodiment, the regulation reservoir is placed subcutaneous under the patient's skin and is operated by pushing the outer surface thereof by means of a finger. The regulation reservoir 1013 is in fluid connection with a bellow shaped servo reservoir 1050 by means of a conduit 1011. In the first closed system 1013, 1011, 1050 shown in FIG. 45*a*, the servo reservoir 1050 contains a minimum of fluid and most fluid is found in the regulation reservoir 1013.

The servo reservoir 1050 is mechanically connected to a larger adjustable reservoir 1052, in this example also having a bellow shape but with a larger diameter than the servo reservoir 1050. The larger adjustable reservoir 1052 is in fluid connection with the apparatus 10. This means that when a user pushes the regulation reservoir 1013, thereby displacing fluid from the regulation reservoir 1013 to the servo reservoir 1050, the expansion of the servo reservoir 1050 will displace a larger volume of fluid from the larger adjustable reservoir 1052 to the apparatus 10. In other words, in this reversed servo, a small volume in the regulation reservoir is compressed with a higher force and this creates a movement of a larger total area with less force per area unit.

Like in the previous embodiment described above with reference to FIGS. 39*a-c*, the regulation reservoir 1013 is preferably provided with means 1013*a* for keeping its shape after compression. This means, which is schematically shown in the figure, will thus keep the apparatus 10 in a stretched position also when the user releases the regulation reservoir. In this way, the regulation reservoir essentially operates as an on/off switch for the system.

Figure 42:
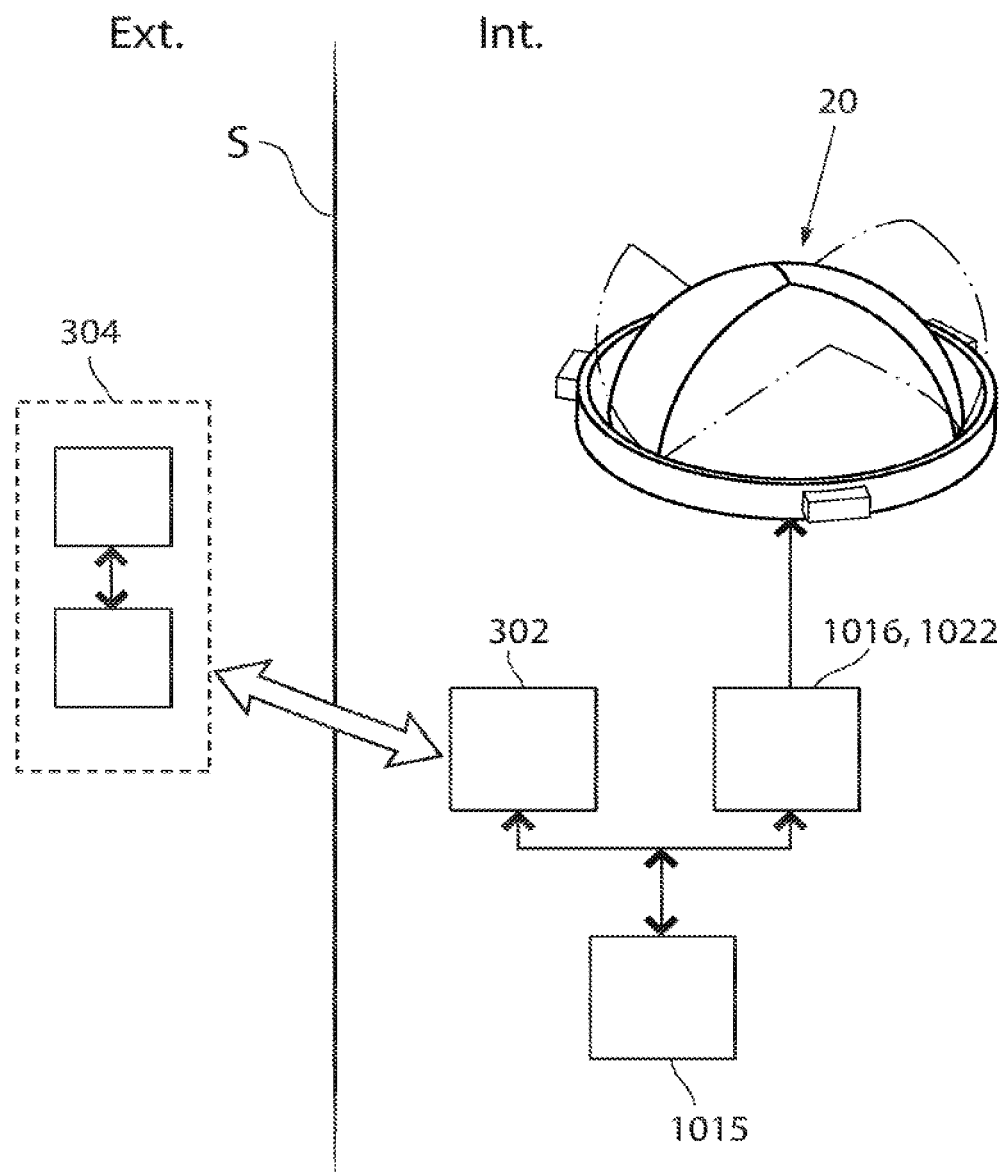

FIG. 42 shows a system of the invention, with the skin of a patient being shown as "S", and with an apparatus 10 of the invention being implanted into a patient, "Int", and with other details on the outside of the patient, "Ext"

Besides the apparatus 30, the implanted equipment comprises an energy transforming device 302 as described above, a battery 1022 and, as an alternative or complement, an accumulator 1016, with both the energy transforming device and the battery/accumulator being controlled by the control device 1015.

The "external equipment" comprises a remote control, which is shown as possibly comprising two parts, i.e. a transmitter or transceiver for transmitting and possibly receiving energy to/from the device 302, and a remote control I, which may be integrated into one physical unit together with the transmitter or transceiver.

The invention also discloses a method as follows:

A. A method of surgically placing a valve of the invention in a patient's heart or blood vessel via a laparoscopic thoracic approach, the method comprising the steps of:
  inserting a needle or a tube like instrument into the thorax of the patient's body,
  using the needle or a tube like instrument to fill the thorax with gas thereby expanding the thoracic cavity,
  placing at least two laparoscopic trocars in the patient's body,
  inserting a camera through one of the laparoscopic trocars into the thorax.
  inserting at least one dissecting tool through one of said at least two laparoscopic trocars and dissecting an intended placement area of the patient,
  placing the valve in any part of the blood stream in the thorax, and
  placing and connecting an implanted energy receiver or source of energy for powering the valve to perform at least one of the following method steps;
  at least partly closing and at least partly opening of the valve.

B. An operation method for surgically placing a valve of the invention in a patient's heart or blood vessel, the method comprising the steps of:
  cutting the patient's skin,
  opening the thoracic cavity,
  dissecting a placement area where to place the valve inside a blood stream in the heart, or the aorta or inside the pulmonary artery of the human patient,
  placing the a valve in the placement area in any part of the blood stream in the thorax, and
  placing and connecting an implanted energy receiver or a source of energy for powering the valve to perform at least one of the following method steps;
  at least partly closing and at least partly opening of the valve.

C. A method of surgically placing a valve of the invention in a patient's heart or blood vessel via a laparoscopic abdominal approach, the method comprising the steps of:
  inserting a needle or a tube like instrument into the abdomen of the patient's body,
  using the needle or a tube like instrument to fill the thorax with gas thereby expanding the abdominal cavity,
  placing at least two laparoscopic trocars in the patient's abdomen
  inserting a camera through one of the laparoscopic trocars into the abdomen,
  inserting at least one dissecting tool through one of said at least two laparoscopic trocars and
  dissecting and creating an opening in the diaphragm muscle,
  dissecting an intended placement area of the patient through said opening,
  placing the valve in any part of the blood stream in the thorax, and
  placing and connecting an implanted energy receiver or source of energy for powering the valve to perform at least one of the following method steps;
  at least partly closing and at least partly opening of the valve.

D. An operation method for surgically placing a valve of the invention in a patient's heart or blood vessel, the method comprising the steps of:
  cutting the patient's skin,
  opening the abdominal cavity,
  dissecting and creating an opening in the diaphragm muscle,
  dissecting a placement area where to place the valve inside a blood stream in the heart, or the aorta or inside the pulmonary artery of the human patient through said opening,
  placing the a valve in the placement area, and
  placing and connecting an implanted energy receiver or a source of energy for powering the valve to perform at least one of the following method steps;
  at least partly closing and at least partly opening of the valve.

E. An operation method for surgically placing a valve of the invention in a patient's heart or blood vessel, via inguinal key-hole surgery approach, the method comprising the steps of:
  cutting the patients skin,
  inserting a needle or a tube like instrument into the inguinal area of the patient's body,
  using the needle or a tube like instrument to fill a cavity with gas thereby expanding the cavity,
  placing at least two laparoscopic trocars in the patient's cavity
  inserting a camera through one of the trocars into the cavity,
  inserting at least one dissecting tool through one of said at least two trocars and
  dissecting the area of the femoral artery, inserting a tube like instrument into the femoral artery of the patient's body,
inserting said valve into the femoral artery,
using said instrument to guide said valve through the femoral artery to the aorta or heart of the patient,
releasing the valve inside of a blood vessel or heart
placing said valve in the blood vessel or heart,
placing and connecting an implanted energy receiver or a source of energy for powering the valve to perform at least one of the following method steps;
at least partly closing and at least partly opening of the valve.

F. An operation method for surgically placing a valve of the invention in a patient's heart or blood vessel, via a inguinal approach, the method comprising the steps of:
cutting the patients skin,
dissecting the inguinal region,
dissecting the area of the femoral artery,
inserting a tube like instrument into the femoral artery of the patient's body,
using said instrument to guide said rotating body through the femoral artery and the aorta to the blood vessel or heart,
releasing the valve inside of the heart or blood vessel,
placing said valve in the blood vessel or heart,
placing and connecting an implanted energy receiver or a source of energy for powering the valve to perform at least one of the following method steps;
at least partly closing and at least partly opening of the valve.

G. In one embodiment of the invention according to any of items A-F, the step of placing the valve additionally comprises the step of:
placing a drive unit for at least partly powering the valve movements in the placement area, inside the blood stream of the blood vessel, inside the heart, or the aorta or inside the pulmonary artery of the patient,
supplying energy from said drive unit to said valve causing movement of said valve.

H. In one embodiment of the invention according to any of items A-F, the step of placing the valve additionally comprises the step of:
placing a drive unit for at least partly powering the valve movements in the placement area, outside the blood stream of the blood vessel, outside the heart, or the aorta or outside the pulmonary artery of the patient,
placing said drive unit on the outside of said valve,
supplying energy from said drive unit to said valve causing movement of said valve.

I. In one embodiment of the invention according to items I or H, the step of supplying energy from said drive unit to said valve, causing movement of said valve, additionally comprises the step of:
supplying wireless or magnetic energy from said drive unit to said valve, causing movement of said valve.

J. In one embodiment of the invention according to any of items G-I, the method additionally comprises the step of:
connecting the drive unit with the energy receiver or source of energy for powering said drive unit.

K. In one embodiment of the invention according to any of items A-D and H, for parts of the valve placed outside the blood stream, combining with the method according to one or more of claims E-G for parts of the valve placed inside the blood stream.

L. In one embodiment of the invention according to item J, said drive unit placed outside the blood stream comprises a stator, and the part of the valve placed inside the blood stream comprises a rotor, wherein said stator supplies wireless energy to said part of the valve placed inside the blood stream, causing rotational movement of at least a part of said drive unit.

M. In one embodiment of the invention according to item L, the drive unit further comprises both said rotor adapted to be placed outside the blood stream, said rotor comprising a magnetic coupling for driving at least a part of the valve placed inside the blood stream with rotational energy, the method further comprising the steps of:
placing said stator and rotor on the outside of said valve including a magnetic coupling in the placement area, wherein said rotor comprises said magnetic coupling, adapted to be magnetically connecting to said valve placed inside the blood stream,
supplying energy to said stator to rotate said rotor and thereby rotating said valve, thereby
causing, through the magnetic coupling, rotating movement of said valve.

N. In one embodiment of the invention according to any of items A-M, an opening is performed from the abdomen through the thoracic diaphragm for placing the energy receiver or energy source in the abdomen.

O. In one embodiment of the invention according to any of items C, D and N, said opening is performed in the thoracic diaphragm at the place where the pericardium is attached to the thoracic diaphragm.

P. In one embodiment of the invention according to any of items A-O, the valve or drive unit uses energy, direct or indirect, from an external energy source, supplying energy non-invasively, without any penetration through the patient's skin to power the valve or drive unit.

Q. In one embodiment of the invention according to any of items A-H, said valve or drive unit is connected to an internal energy source via a cable, the method of placement further comprising:
dissecting and placing a wire connected to the valve or drive unit into the right atrium of the heart and further up in the venous blood vessel system,
exiting the system in or closer to the subcutaneous area, such as in the vena subclavia, vena jugularis or vena brachialis
placing an internal energy source in the subcutaneous area or close thereto or in the thorax or abdomen,
supplying from an external energy source energy non-invasively, without any penetration through the patient's skin to power the internal energy source for indirect or direct power the valve or drive unit.

R. In one embodiment of the invention according to any of items A-H, the method of placement further comprises;
placing an electrode in the right atrium or ventricle of the heart
placing the wire to the electrode via the right atrium of the heart and further up in the venous blood vessel system,
exiting the blood vessel system in or closer to the subcutaneous area, such as in the vena subclavia, vena jugularis or vena brachialis,
placing an internal control unit in the subcutaneous area or close thereto or in the thorax or abdomen, the method further comprising at least one of the following steps;
receiving sensor input relating to electrical pulses or muscle contractions of the heart or
transmitting energy pulses from said electrode for controlling heart contractions,
coordinating the valve or drive unit.

In various embodiments, the artificial valve of the invention also exhibits the following features:

A. The artificial valve is adapted to pass through a laparoscopic trocar in the patient's body.

B. The artificial valve of item A is adapted to pass through an opening in the diaphragm muscle from the abdominal side.

C. The artificial valve of item A is adapted to be inserted into the femoral artery and further adapted to be released inside of the heart or blood vessel.

D. The artificial valve of item A comprises a drive unit for at least partly powering the valve movements, adapted to be placed inside the blood stream including a blood vessel or heart.

E. The artificial valve of item A comprises a drive unit for at least partly powering the valve movements, adapted to be placed outside the blood stream including a blood vessel or heart.

F. The artificial valve of item D or E, wherein said drive unit is adapted to supply wireless or magnetic energy, said valve being adapted to receive said wireless or magnetic energy to cause movements of said valve.

G. The artificial valve of item D or E, wherein said drive unit comprises a stator, adapted to be placed outside the blood stream, the blood vessel or heart, and further comprising a rotor adapted to be placed inside the blood stream, wherein said stator is adapted to supply wireless or magnetic energy to the rotor placed inside the blood stream, causing movements of at least a part of said valve placed inside the blood stream.

H. The artificial valve of item D or E, wherein said drive unit comprises a stator and a rotor, adapted to be placed outside the blood stream, the blood vessel or heart, said rotor comprising a magnetic coupling for driving at least a part of the valve placed inside the blood stream with kinetic energy.

I. The artificial valve of item A, wherein an energy receiver or energy source is adapted to be placed in the abdomen.

J. The artificial valve of item D or E, comprising an electric wire adapted to connect said valve or drive unit to an internal energy source, said wire adapted to pass into the right atrium of the heart and further up in the venous blood vessel system, exiting the blood vessel system in or closer to the subcutaneous area, wherein said internal energy source is adapted to be connected to said wire via the subcutaneous area.

K. The artificial valve of item A, comprising:
an internal control unit,
a sensor sensing physiological electrical pulses or muscle contractions of the heart,
wherein said control unit controls said valve according to the sensed information.

L. The artificial valve of item J:
in which said internal energy source comprises an internal control unit adapted to transmit energy pulses to said electrode for achieving and controlling heart contractions, wherein said control unit is adapted to coordinate the valve or drive unit.

The invention is not limited to the examples of embodiments described above and shown in the drawings, but may be freely varied within the scope of the appended claims.

The invention claimed is:

1. A method of surgically placing an auxiliary artificial valve in a blood vessel of a patient, the method comprising the steps of:
making an incision in the skin of the patient,
introducing the auxiliary artificial valve into the body of the patient, wherein the auxiliary artificial valve comprises at least one moving part which is adapted to be able to move to assume an open and a closed position for opening and closing, respectively, of the blood flow through the blood vessel; and an initial moving resistance mechanism adapted to let the at least one moving part initiate its movement to said open position at a blood pressure difference over the valve corresponding to a barrier force of said initial movement resistance, such that the artificial valve in the beginning of the systole will remain closed slightly longer than a normal heart-valve, thereby causing an increased amount of blood flow into the coronary arteries, and
placing the auxiliary artificial valve in the aorta between and at a distance from the exit to the coronary arteries and the exit to the carotid arteries.

2. The method according to claim 1, wherein the method is a vascular approach, and wherein the method comprises the steps of making an incision in a blood vessel of the patient and introducing the valve in the blood vessel.

3. The method according to claim 1, wherein the method is an inguinal vascular approach.

4. The method according to claim 1, wherein the method is a thoracic approach.

5. The method according to claim 4, wherein the thoracic approach comprises at least one of the steps of:
opening the thoracic cavity,
dissecting a placement area of the aorta,
introducing the auxiliary artificial valve into the thorax of the patient, and
placing the valve in the placement area.

6. The method according to claim 4, wherein the method is a thoracic laparoscopic approach.

7. The method according to claim 6, wherein the thoracic laparoscopic approach comprises at least one of the steps of:
inserting a needle or a tube like instrument into the thorax of the patient's body,
using the needle or a tube like instrument to fill the thorax with gas thereby expanding the thoracic cavity,
inserting a at least one laparoscopic trocar,
inserting a camera through the laparoscopic trocar into the thorax,
inserting at least one dissecting tool through at least one laparoscopic trocar and dissecting a placement area,
placing the valve in the placement area using laparoscopic tools.

8. The method according to claim 1, wherein the method is an abdominal approach.

9. The method according to claim 8, wherein the abdominal approach comprises at least one of the steps of:
opening the abdomen of the patient,
making an incision in the diaphragm of the patient, for reaching the thorax of the patient,
dissecting a placement area of the aorta,
introducing the auxiliary artificial valve into the abdomen of the patient,
introducing the auxiliary artificial valve into the thorax of the patient, and
placing the valve in the placement area.

10. The method according to claim 8, wherein the method is an abdominal laparoscopic approach.

11. The method according to claim 10, wherein the abdominal laparoscopic approach comprises at least one of the steps of:
inserting a needle or a tube like instrument into the abdomen of the patient, using the needle or a tube like instrument to fill the abdomen with gas thereby expanding the abdominal cavity, inserting a at least one laparoscopic trocar, inserting a camera through the laparoscopic trocar, into the abdomen, inserting at least one dissecting tool through at least one laparoscopic trocar, making an incision in the diaphragm of the patient, for reaching the thorax of the patient, dissecting a placement area of the aorta, introducing the auxiliary artificial valve into the abdomen of the patient, introducing the auxiliary artificial valve into the thorax of the patient, and placing the valve in the placement area using laparoscopic tools.

12. The method according to claim 1, wherein the method further comprises implanting a source of energy for powering the auxiliary artificial valve.

13. The method according to claim 1, wherein the method further comprises implanting a wireless energy receiver for receiving wireless energy after said wireless energy receiver has been implanted.

14. The method according to claim 13, wherein the step of implanting a wireless energy receiver comprises implanting the wireless energy receiver in the abdomen.

15. The method according to claim 1, wherein the method further comprises implanting at least one pressure sensor for sensing the blood pressure on at least one side of the auxiliary artificial valve.

16. The method according to claim 1, wherein the method further comprises implanting at least one control unit for controlling the opening and closing of said auxiliary artificial valve.

17. The method according to claim 1, wherein the method further comprises placing a drive unit for at least partly powering the auxiliary artificial valve, on the outside of the blood vessel.

18. The method according to claim 1, wherein the method further comprises implanting at least one sensor for sensing the electrical pulses or muscle contractions of the heart.

19. The method according to claim 1, wherein the method further comprises implanting an internal wireless signal transceiver for communicating with an external wireless signal transceiver located outside of the patient's body.

20. The method according to claim 1, wherein the method further comprises operating the auxiliary artificial valve to move an open position at a level of blood pressure on a blood supplying side of the auxiliary artificial valve which is at least 5 mm Hg higher than the diastolic aortic blood pressure of the patient on the other side of the valve.

21. A method of surgically placing an auxiliary artificial valve in a blood vessel of a patient, the method comprising the steps of:

making an incision in the skin of the patient, introducing the auxiliary artificial valve into the body of the patient, placing the auxiliary artificial valve in the aorta between and at a distance from the exit to the coronary arteries and the exit to the carotid arteries, and implanting at least one pressure sensor for sensing the blood pressure on at least one side of the auxiliary artificial valve.

* * * * *